US009566321B2

(12) United States Patent
Giacalone

(10) Patent No.: US 9,566,321 B2
(45) Date of Patent: Feb. 14, 2017

(54) IMMUNOMODULATORY MINICELLS AND METHODS OF USE

(71) Applicant: Vaxiion Therapeutics, LLC, San Diego, CA (US)

(72) Inventor: Matthew J. Giacalone, San Diego, CA (US)

(73) Assignee: VAXIION THERAPEUTICS, LLC, San Diego, CA (US)

( * ) Notice: Subject to any disclaimer, the term of this patent is extended or adjusted under 35 U.S.C. 154(b) by 0 days.

(21) Appl. No.: 15/044,403

(22) Filed: Feb. 16, 2016

(65) Prior Publication Data

US 2016/0158334 A1 Jun. 9, 2016

Related U.S. Application Data

(63) Continuation of application No. 14/044,525, filed on Oct. 2, 2013, now Pat. No. 9,267,108.

(60) Provisional application No. 61/709,102, filed on Oct. 2, 2013.

(51) Int. Cl.

| | |
|---|---|
| ***A61K 39/02*** | (2006.01) |
| ***A61K 39/08*** | (2006.01) |
| ***A61K 39/00*** | (2006.01) |
| ***C12N 1/20*** | (2006.01) |
| ***C07K 14/33*** | (2006.01) |
| *A61K 38/00* | (2006.01) |

(52) U.S. Cl.

CPC ........... *A61K 39/0291* (2013.01); *C07K 14/33* (2013.01); *C12N 1/20* (2013.01); *A61K 38/00* (2013.01); *A61K 39/02* (2013.01); *A61K 2039/52* (2013.01); *A61K 2039/585* (2013.01)

(58) Field of Classification Search

CPC ........ A61K 38/00; A61K 39/02; C07K 14/33; C12N 1/20

USPC ..................... 424/184.1, 234.1, 239.1, 278.1

See application file for complete search history.

(56) References Cited

U.S. PATENT DOCUMENTS

| | | | |
|---|---|---|---|
| 4,895,724 | A | 1/1990 | Cardinal et al. |
| 5,314,695 | A | 5/1994 | Brown |
| 5,348,867 | A | 9/1994 | Georgiou et al. |
| 7,183,105 | B2 | 2/2007 | Sabbadini et al. |
| 9,267,108 | B2 | 2/2016 | Giacalone |
| 2003/0166099 | A1 | 9/2003 | Sabbadini et al. |
| 2003/0207833 | A1 | 11/2003 | Berkley et al. |
| 2005/0147590 | A1 | 7/2005 | Sabbadini et al. |
| 2007/0237744 | A1 | 10/2007 | Brahmbhatt et al. |
| 2007/0298056 | A1 | 12/2007 | Brahmbhatt et al. |
| 2008/0051469 | A1 | 2/2008 | Brahmbhatt et al. |
| 2010/0112670 | A1 | 5/2010 | Giacalone et al. |
| 2010/0189691 | A1 | 7/2010 | Fruehauf et al. |
| 2012/0207754 | A1 | 8/2012 | Giacalone et al. |

FOREIGN PATENT DOCUMENTS

| | | |
|---|---|---|
| WO | WO 93/10214 | 5/1993 |
| WO | WO 98/52547 | 11/1998 |
| WO | WO 99/59643 | 11/1999 |
| WO | WO 2005/056749 | 6/2005 |
| WO | WO 2005/079854 | 9/2005 |
| WO | WO 2006/021894 | 3/2006 |
| WO | WO 2006/055024 | 5/2006 |
| WO | WO 2009/012493 | 1/2009 |
| WO | WO 2009/158364 | 12/2009 |

OTHER PUBLICATIONS

Chang et al., "Cloning and Sequence Analysis of a Novel Hemolysin Gene (*vllY*) *Vibrio vulnificus*", Applied and Environmental Microbiology, vol. 63, No. 10, pp. 3851-3857 (1997).

Wintermeyer et al., "Characterization of legiolysin (*lly*), responsible for haemolytic activity, colour production, and fluorescence of *Legionella pneumophila*", Molecular Microbiology, vol. 5, issue 5, pp. 1135-1143 (1991).

International Search Report dated Dec. 20, 2013 in International Patent Application No. PCT/US2013/063117 filed Oct. 2, 2013.

Han et al., "Ligand-directed retroviral targeting of human breast cancer cells" Proc. Natl. Acad. Sci. USA, 92:9747-9751, 1995 (1995).

Iijima et al., "Nanocapsules incorporating IgG Fc-binding domain derived from *Staphylococcus aureus* protein a for displaying IgGs on immunosensor chips," *Biomaterials*, 32: 1453-1464, (2011).

Klier et al., Combining bacterial-immunotherapy with therapeutic antibodies: a novel therapeutic concept, Vaccine, 30:2786-2794 (2012), published ahead of print Feb. 13, 2012 (online).

MacDiarmid et al., "Bacterially Derived 400 nm Particles for Encapsulation and Cancer Cell Targeting of Chemotherapeutics," *Cancer Cell*, 11: 431-445, (May 2007).

Moks et al., "*Staphylococcal* protein a consists of five IgG-binding domains", European Journal of Biochemistry, vol. 156, issue 3, pp. 637-643 (1986).

Patyar et al., "Bacteria in cancer therapy: a novel experimental strategy," Journal of Biomedical Science, 17:21 (2010).

Stone et al., "The Fc binding site for *streptococcal* protein G is in the C gamma 2-C gamma 3 interface region of IgG and is related to the sites that bind *staphylococcal* protein A and human rheumatoid factors." The Journal of Immunology, vol. 143, No. 2, pp. 565-570 (1989).

Tai et al., "Antibody-medicated targeting of replication-competent retroviral vectors", Human Gene Therapy, 14:789-802 (2003).

Extended European Search Report dated Apr. 22, 2014 in European Application No. 12747781.8.

International Search Report and Written Opinion dated Mar. 23, 2012 of International Patent Application PCT/US2012/025272, filed Feb. 15, 2012.

(Continued)

*Primary Examiner* — Rodney P Swartz

(74) *Attorney, Agent, or Firm* — Knobbe Martens Olson & Bear LLP

(57) ABSTRACT

The present disclosure is related to immunomodulatory bacterial minicells and methods of using the minicells.

12 Claims, 12 Drawing Sheets

(56) References Cited

OTHER PUBLICATIONS

Office Action dated May 23, 2013 of U.S. Appl. No. 13/397,313, filed Feb. 15, 2012.

Office Action dated Jan. 14, 2014 of U.S. Appl. No. 13/397,313, filed Feb. 15, 2012.

Advisory Action dated Jun. 4, 2014 of U.S. Appl. No. 13/397,313, filed Feb. 15, 2012.

Tsuji, et al., Mar. 2016, "Preclinical evaluation of VAX-IP, a novel bacterial minicell-based biopharmaceutical for nonmuscle invasive bladder cancer", Molecular Therapy, Oncolytics 3:16004.

Newman et al., Apr. 15, 2012 "Efficient targeted delivery of protein toxins using self-manufacturing nanoparticles (minicells) derived from bacteria" Cancer Research, vol. 72, No. 8 supplement, p. 5703.

Extended Search Report dated Apr. 19, 2016 issued in EP 13844430.2.

Final Office Action dated Mar. 8, 2016 issued in the U.S. Appl. No. 13/397,313, filed on Feb. 15, 2012.

Office Action dated Sep. 21, 2015 issued in the U.S. Appl. No. 13/397,313, filed on Feb. 15, 2012.

IMMUNOMODULATORY MINICELLS AND METHODS OF USE

RELATED APPLICATIONS

The present application is a continuation application of U.S. patent application Ser. No. 14/044,525, filed on Oct. 2, 2013, which claims priority under 35 U.S.C. §119(e) to U.S. Provisional Application No. 61/709,102, filed on Oct. 2, 2012. All of the aforementioned priority applications are herein expressly incorporated by reference in their entireties.

REFERENCE TO SEQUENCE LISTING

The present application is being filed along with a Sequence Listing in electronic format. The Sequence Listing is provided as a file entitled SEQLISTING.TXT, created Feb. 5, 2016, which is 20 Kb in size. The information in the electronic format of the Sequence Listing is incorporated herein by reference in its entirety.

BACKGROUND

Field

The present application is drawn to compositions and methods for the production, purification, formulation, and use of immunomodulatory eubacterial minicells for use in treatment of diseases, such as bladder cancer and other malignancies.

Description of the Related Art

The following description of the background of the invention is provided to aid in understanding the invention, but is not admitted to describe or constitute prior art to the invention. The contents of the articles, patents, and patent applications, and all other documents and electronically available information mentioned or cited in this application, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

It is well known that the immune system plays an important role in the prevention of cancer. It is becoming increasingly clear that immune modulation may be an attractive therapeutic approach in the treatment of cancer. The longest standing marketed anticancer immunomodulatory therapy is a live attenuated strain of *Mycobacterium bovis*, Bacille Calmette-Guerin (BCG), which is used as a postoperative adjuvant therapy for the treatment of non-muscle invasive bladder cancer. Other non-marketed experimental anticancer immunomodulatory approaches include the use of other live attenuated species of bacteria such as *Salmonella typhimurium, Bifidobacteria, Listeria monocytogenes, Streptococcus pyrogenes, Serratia marcescens, Clostridium novyi, Salmonella choleraesius*, and *Vibrio cholera*. While somewhat effective, each strain used is limited by the risk of infection, fear of genetic reversion of live attenuated strains to pathogenicity, and sepsis. All of these approaches have been met with extreme toxicity reminiscent of the living bacterial infection with toxicity occurring at or near the most efficacious dose. This results in narrow therapeutic indices for each strain type.

To address toxicity issues with living bacteria as immunomodulatory therapy, others have attempted to use different bacterial components (as opposed to the whole living organism) to generate the same immunological effect. Experimental therapeutics of this type include purified bacterial toxins, purified pro-inflammatory lipopolysaccharides (LPS), purified teichoic acid (TCA), and other bacterial cell wall preparations and other bacterial sub-cellular fractions. These approaches have improved toxicity profiles but are with a concomitant loss of efficacy in some cases. Additionally, many only stimulate a polarizing immune response (either Th1 or Th2) with the majority stimulating Th2 (antibody generating) responses. It is reasonably well documented that a Th1 (cellular immune response) response seems to be preferential with respect to having an anti-tumor immunomodulatory effect. Last, these preparations can be difficult to manufacture at a scale and quality to support market demand and may only ultimately generate a subset of immune responses incapable of generating anti-tumor effects. In the case of protein toxins used in the treatment of most cancers, efficacy of the protein toxin is significantly limited by toxicity to normal tissues. In addition, drug pharmacokinetic (PK) parameters contributing to systemic exposure levels frequently are not and cannot be fully optimized to simultaneously maximize anti-tumor activity and minimize side-effects, particularly when the same cellular targets or mechanisms are responsible for anti-tumor activity and normal tissue toxicity. Again, this results in a very narrow therapeutic index, common for most protein toxins.

In addition to live bacterial vectors and bacterial components as immunomodulatory "generalists", other investigators have attempted to develop different, specific Th1 immunomodulatory cytokines and chemokines as anticancer therapeutics. Examples include but are not limited to interferon gamma (IFN-γ), interferon alpha (IFN-α), granulocyte macrophage colony-stimulating factor (GMCSF), tumor necrosis factor alpha (TNF-α), interleukin-2 (IL-2), interleukin-12 (IL-12), and interleukin-18 (IL-18). Each of these approaches has been limited by unanticipated and severe toxicity with little or no immunological therapeutic benefit when administered alone. It is becoming somewhat clear that single cytokine or chemokine agents does not invoke the full spectrum of Th1 immune response needed to have an anticancer effect and that these factors are likely working in concert at varying levels that are dynamic over time. This is a nearly impossible cascade of immunological signaling events to recapitulate and orchestrate with a multiplex product formulation. Most single agent cytokines have failed clinically, the exception being pegylated interferon for the treatment of chronic hepatitis C viral infections.

Based on the observed limitations of these approaches to the development of immunomodulatory anticancer therapeutics, there is a need for an immunomodulatory therapy that could mimic a live bacterial infection without introducing the risk of infection and infection-associated toxicity while still invoking a potent and diverse enough immune response to impart anticancer activity.

SUMMARY

Some embodiments disclose a bacterial minicell, comprising a cholesterol-dependent cytolysin protein, wherein said minicell does not display an antibody or other molecule comprising an Fc region of an antibody.

In some embodiments, the cholesterol-dependent cytolysin protein is selected from listeriolysin O, listeriolysin O L461T, listeriolysin O E247M, listeriolysin O D320K, listeriolysin O E247M, listeriolysin O D320K, listeriolysin O L461T, streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin. In some embodiments, the cholesterol-dependent cytolysin protein is perfringolysin O. In some embodiments, the cholesterol-dependent cytolysin protein comprises the amino acid sequence of SEQ ID NO: 1.

In some embodiments, the minicell further comprises invasin. In some embodiments, the minicell does not comprise invasin.

In some embodiments, the minicell further comprises a Th1 cytokine. In some embodiments, the Th1 cytokine is selected from IL-2, GMCSF, IL-12p40, IL-12p70, IL-18, TNF-α, and IFN-γ.

In some embodiments, the minicell further comprises a Th2 cytokine. In some embodiments, the Th2 cytokine is selected from IL-1α, IL-1β, IL-4, IL-5, IL-6, IL-10, and IL-13.

In some embodiments, the minicell further comprises a phospholipase. In some embodiments, the phospholipase is PC-PLC or PI-PLC.

In some embodiments, the minicell comprises a protein toxin selected from fragments A/B of diphtheria toxin, fragment A of diphtheria toxin, anthrax toxins LF and EF, adenylate cyclase toxin, gelonin, botulinolysin B, botulinolysin E3, botulinolysin C, botulinum toxin, cholera toxin, *Clostridium* toxins A, B and alpha, ricin, shiga A toxin, shiga-like A toxin, cholera A toxin, pertussis S1 toxin, *Pseudomonas* exotoxin A, *E. coli* heat labile toxin (LTB), melittin, activated caspases, pro-caspases, cytokines, chemokines, cell-penetrating peptides, and combinations thereof.

In some embodiments, the minicell does not comprise any other therapeutically-active moiety. In some embodiments, the minicell does not comprise a therapeutic small molecule, any other therapeutic protein, or a therapeutic nucleic acid. In some embodiments, the minicell does not display the Fc binding portion of Protein G or Protein A. In some embodiments, the minicell does not comprise any therapeutic nucleic acid, for example an siRNA.

Some embodiments disclosed herein provide a minicell-producing bacterium, comprising: an expressible gene encoding a minicell-producing gene product that modulates one or more of septum formation, binary fission, and chromosome segregation; and a recombinant expression cassette capable of the functional expression of a cholesterol-dependent cytolysin protein, wherein the bacterium does not display an antibody or other molecule comprising an Fc region of an antibody and does not display the Fc binding portion of Protein G or Protein A.

In some embodiments, the minicell-producing bacterium further comprises: an expressible "genetic suicide" gene encoding a heterologous endonuclease, wherein the chromosome of the minicell-producing bacteria comprises one or more recognition sites of the endonuclease; a defined auxotrophy; and a deletion or mutation in the lpxM/msbB gene.

In some embodiments, the endonuclease is selected from I-CeuI, PI-SceI, I-ChuI, I-CpaI, I-SceIII, I-CreI, I-MsoI, I-SceII, I-SceIV, I-CsmI, I-DmoI, I-PorI, PI-TliI, PI-TliII, and PI-ScpI. In some embodiments, the auxotrophy is due to a deletion or inactivating mutation in an essential metabolic gene. In some embodiments, the expressible gene encoding the minicell-producing gene product is selected from ftsZ, sulA, ccdB, and sfiC.

In some embodiments, the cholesterol-dependent cytolysin protein is selected from listeriolysin O, listeriolysin O L461T, listeriolysin O E247M, listeriolysin O D320K, listeriolysin O E247M, listeriolysin O D320K, listeriolysin O L461T, streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin. In some embodiments, the cholesterol-dependent cytolysin protein is perfringolysin O. In some embodiments, the cholesterol-dependent cytolysin protein comprises SEQ ID NO: 1.

In some embodiments, the minicell further comprises a recombinant expression cassette capable of the functional expression of invasin.

Some embodiments provide a method of treating cancer, comprising administering to a patient in need thereof a bacterial minicell comprising a cholesterol-dependent cytolysin protein, wherein said administration induces a non-immunogenic anti-tumor immunomodulatory effect.

In some embodiments, the minicell does not display an antibody or other molecule comprising an Fc region of an antibody.

In some embodiments, the cholesterol-dependent cytolysin protein is selected from listeriolysin O, listeriolysin O L461T, listeriolysin O E247M, listeriolysin O D320K, listeriolysin O E247M, listeriolysin O D320K, listeriolysin O L461T, streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin. In some embodiments, the cholesterol-dependent cytolysin protein is perfringolysin O. In some embodiments, the cholesterol-dependent cytolysin protein comprises SEQ ID NO: 1.

In some embodiments, the minicell further comprises invasin. In some embodiments, the minicell does not comprise invasin.

In some embodiments, the minicell further comprises a Th1 cytokine. In some embodiments, the Th1 cytokine is selected from IL-2, GMCSF, IL-12p40, IL-12p70, IL-18, TNF-α, and IFN-γ.

In some embodiments, the minicell further comprises a Th2 cytokine. In some embodiments, the Th2 cytokine is selected from IL-1α, IL-1β, IL-4, IL-5, IL-6, IL-10, and IL-13.

In some embodiments, the minicell further comprises a phospholipase. In some embodiments, the phospholipase is PC-PLC or PI-PLC.

In some embodiments, the method further comprises a protein toxin selected from fragments A/B of diphtheria toxin, fragment A of diphtheria toxin, anthrax toxins LF and EF, adenylate cyclase toxin, gelonin, botulinolysin B, botulinolysin E3, botulinolysin C, botulinum toxin, cholera toxin, *Clostridium* toxins A, B and alpha, ricin, shiga A toxin, shiga-like A toxin, cholera A toxin, pertussis S1 toxin, *Pseudomonas* exotoxin A, *E. coli* heat labile toxin (LTB), melittin, activated caspases, pro-caspases, cytokines, chemokines, cell-penetrating peptides, and combinations thereof.

In some embodiments, the minicell does not comprise any other therapeutically-active moiety. In some embodiments, the minicell does not comprise a therapeutic small molecule, any other therapeutic protein, or a therapeutic nucleic acid.

In some embodiments, the minicell does not display the Fc binding portion of Protein G or Protein A.

In some embodiments, the cancer comprises a solid tumor, metastatic tumor, or liquid tumor. In some embodiments, the cancer is of epithelial, fibroblast, muscle or bone origin. In some embodiments, the cancer is selected from breast, lung, pancreatic, prostatic, testicular, ovarian, gastric, intestinal, mouth, tongue, pharynx, hepatic, anal, rectal, colonic, esophageal, gall bladder, skin, uterine, vaginal, penal, and renal cancers. In some embodiments, the cancer is urinary bladder cancer. In some embodiments, the cancer is selected from adenocarcinomas, sarcomas, fibrosarcomas, and cancers of the eye, brain, and bone. In some embodiments, the cancer is selected from non-Hodgkin's lymphoma, myeloma, Hodgkin's lymphoma, acute lymphocytic leukemia, chronic lymphocytic leukemia, acute myeloid leukemia, and chronic myeloid leukemia.

In some embodiments, the administration generates a Th1-dominated immune response. In some embodiments, the administration generates a Th2-dominated immune response

DETAILED DESCRIPTION

Definitions

Figure 1:
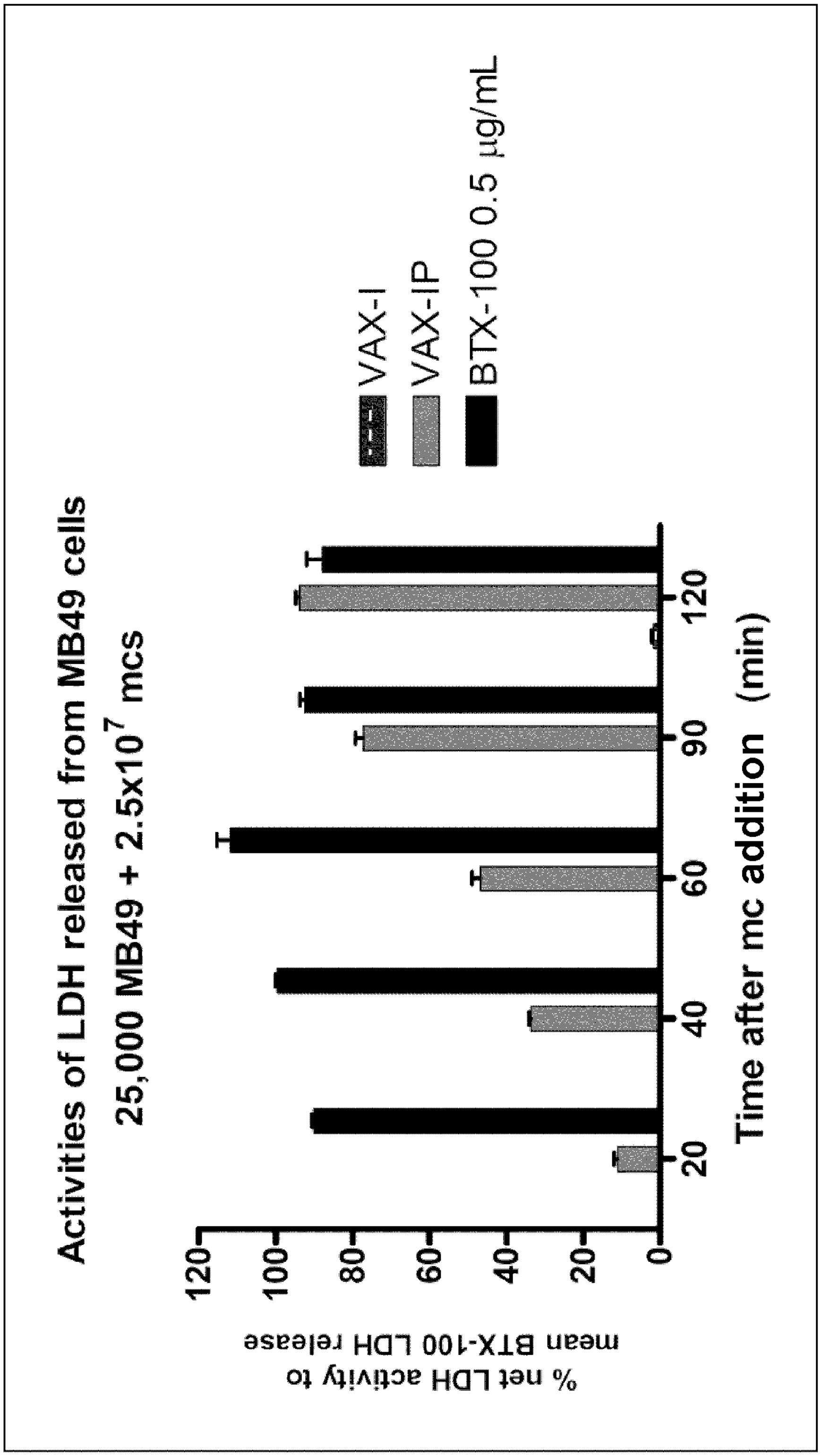
FIG. 1 is a histogram showing the results of a lactate dehydrogenase (LDH) release assay indicates PFO-mediated mammalian cell membrane permeabilization.

As used herein, the term "Th1 immunomodulatory minicells" refers to minicells that are capable of stimulating a Th1 immune response.

As used herein, the term "Th2 immunomodulatory minicells" refers to minicells that are capable of stimulating a Th2 immune response.

As used herein, the term "Th1/Th2 immunomodulatory minicells" refers to minicells that are capable of stimulating both a Th1 and Th2 immune response.

As used herein, the term "recombinant invasive immunomodulatory minicell" refers to a minicell that has been genetically engineered to express and display heterologous minicell surface proteins capable of stimulating internalization into eukaryotic cells.

As used herein, the term "naturally invasive immunomodulatory minicell" refers to a minicell produced from a normally invasive bacterium such that said minicells express and display naturally occurring minicell surface proteins capable of stimulating internalization into eukaryotic cells.

As used herein, the term "immunogenic" refers to an antigen-specific humoral or cellular immune response, mediated by adaptive immune mechanisms. An immunogenic minicell directs the immune response to respond to a particular and specific antigen and is useful in the context of using immunogenic minicells as a vaccine specific for a pathogen, for example.

As used herein, the term "immunomodulatory" refers to the generic modulation (i.e. not immunogenic per se) of the immune response in a desired fashion including but not limited the production of Th1 and Th2 immune responses.

As used herein, the term "immunotherapy" refers to the use of an immunomodulatory compound, for example an immunomodulatory minicell, to generate a generic (i.e. not immunogenic per se) immune response that has beneficial effect with respect to the elimination or slowing the progression of disease, especially cancer.

As used herein, the term "adherent minicell" refers to a minicell that is capable of binding and adhering to the surface of a non-constitutively phagocytic As used eukaryotic cell without stimulating appreciable endocytosis of said minicells. herein, the term "mucoadherent minicell" refers to a minicell that is capable of binding and adhering to a mucosal surface.

As used herein, the term "VAX-P minicells" refers to minicells that express and comprise perfringolysin O (PFO).

As used herein, the term "VAX-IP minicells" refers to minicells that express and display the pan-Betal-integrin-targeting cell surface molecule invasin from *Yersinia pseudotuberculosis* and any functional equivalents thereof, wherein the minicells further comprise perfringolysin O (PFO).

As used herein, the term "VAX-IPT minicells" refers to minicells that express and display the pan-Betal-integrin-targeting cell surface molecule invasin from *Yersinia pseudotuberculosis* and any functional equivalents thereof, wherein the minicells further comprise perfringolysin O (PFO) and a protein toxin.

As used herein, the term "VAX-IPP minicells" refers to minicells that express and display the pan-Betal-integrin-targeting cell surface molecule invasin from *Yersinia pseudotuberculosis* and any functional equivalents thereof, wherein the minicells comprise perfringolysin O (PFO) and an exogenous polypeptide other than a protein toxin.

As used herein, the term "VAX-IPD minicells" refers to minicells that express and display the pan-Betal-integrin-targeting cell surface molecule invasin from *Yersinia pseudotuberculosis* and any functional equivalents thereof, wherein the minicells comprise perfringolysin O (PFO) and the catalytic fragment of diphtheria toxin.

As used herein, the term "VAX-IPG minicells" refers to minicells that express and display the pan-Betal-integrin-targeting cell surface molecule invasin from *Yersinia*

*pseudotuberculosis* and any functional equivalents thereof, wherein the minicells comprise perfringolysin O (PFO) and gelonin.

As used herein, the term "VAX-IPPA minicells" refers to minicells that express and display the pan-Betal-integrin-targeting cell surface molecule invasin from *Yersinia pseudotuberculosis* and any functional equivalents thereof, wherein the minicells comprise perfringolysin O(PFO) and Pseudomonas exotoxin A.

As used herein, the term "VAX-IPR minicells" refers to minicells that express and display the pan-Betal-integrin-targeting cell surface molecule invasin from *Yersinia pseudotuberculosis* and any functional equivalents thereof, wherein the minicells comprise perfringolysin O (PFO) and ricin A.

As used herein, the term "pore-forming cytolysin protein" and the term "cholesterol-dependent cytolysin protein" are used interchangeably and refer to a protein that can attack cell membranes that comprise cholesterol to form pore(s) on the cell membrane. For some cholesterol-dependent cytolysin proteins, the presence of cholesterol in the cell membrane is not required for the cholesterol-dependent cytolysin protein to bind to the cell membrane. For example, the cholesterol-dependent cytolysin protein can be a member of the family of β-barrel pore-forming exotoxins secreted by Gram-positive bacteria. Non-limiting examples of cholesterol-dependent cytolysin proteins include listeriolysin O, listeriolysin O L461T, listeriolysin O E247M, listeriolysin O D320K, listeriolysin O E247M, listeriolysin O D320K, listeriolysin O L461T, streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, pyolysin, and perfringolysin O. In some embodiments, the cholesterol-dependent cytolysin protein comprises an amino acid sequence of ECTGLAWEWWR (SEQ ID NO: 1). In some embodiments, the cholesterol-dependent cytolysin protein comprises an amino acid sequence of WEWWRT (SEQ ID NO: 2).

As used herein, the term "therapeutic nucleic acid" refers to a nucleic acid molecule that has a therapeutic effect when introduced into a eukaryotic organism (e.g., a mammal such as human). A therapeutic nucleic acid can be, for example, a ssDNA, a dsDNA, a ssRNA (including a shRNA), a dsRNA (including siRNA), a tRNA (including a rare codon usage tRNA), a mRNA, a micro RNA (miRNA), a ribosomal RNA (rRNA), a peptide nucleic acid (PNA), a DNA:RNA hybrid, an antisense oligonucleotide, a ribozyme, an aptamer, or any combination thereof.

As used herein, the term "therapeutic protein" refers to a protein that has a therapeutic effect when introduced into a eukaryotic organism (e.g., a mammal such as human). A therapeutic polypeptide can be, for example, a protein toxin, a cholesterol-dependent cytolysin, a functional enzyme, an activated caspase, a pro-caspase, a cytokine, a chemokine, a cell-penetrating peptide, or any combination and/or plurality of the proceeding.

As used herein, the term "therapeutic" means having a biological effect or combination of biological effects that prevents, inhibits, eliminates, or prevents progression of a disease or other aberrant biological processes in an animal. A therapeutically-active moiety can include, for example, a therapeutically active small molecule, a therapeutically active protein, and/or a therapeutically active nucleic acid, As used herein, the term "small molecule" refers to a molecule that has a biological effect and that has a molecular weight of less than 5000 Daltons. In some embodiments, small molecules have a molecular weight of less than 2500 Daltons. In some embodiments, small molecules have a molecular weight of less than 1000 Daltons. In some embodiments, small molecules have a molecular weight of less than 800 Daltons. In some embodiments, small molecules have a molecular weight of less than 500 Daltons.

As used herein, the term "therapeutic small molecule drug" or "small molecule drug" refers to a small molecule that has a therapeutic effect when introduced into a eukaryotic organism (e.g., a mammal such as human).

As used herein, the term "beta1 integrin invasin target" refers to a mammalian beta1 integrin heterodimer capable of being bound by invasin.

As used herein, the term "prokaryotic cell division gene" refers to a gene that encodes a gene product that participates in the prokaryotic cell division process. Many cell division genes have been discovered and characterized in the art. Examples of cell division genes include, but are not limited to, zipA, sulA, secA, dicA, dicB, dicC, dicF, ftsA, ftsI, ftsN, ftsK, ftsL, ftsQ, ftsW, ftsZ, minC, minD, minE, seqA, ccdB, sfiC, and ddlB.

As used herein, the term "transgene" refers to a gene or genetic material that has been transferred naturally or by any of a number of genetic engineering techniques from one organism to another. In some embodiments, the transgene is a segment of DNA containing a gene sequence that has been isolated from one organism and is introduced into a different organism. This non-native segment of DNA may retain the ability to produce RNA or protein in the transgenic organism, or it may alter the normal function of the transgenic organism's genetic code. In some embodiments, the transgene is an artificially constructed DNA sequence, regardless of whether it contains a gene coding sequence, which is introduced into an organism in which the transgene was previously not found.

As used herein, an agent is said to have been "purified" if its concentration is increased, and/or the concentration of one or more undesirable contaminants is decreased, in a composition relative to the composition from which the agent has been purified. In some embodiments, purification includes enrichment of an agent in a composition and/or isolation of an agent therefrom.

The term "sufficiently devoid of parental cells", synonymous with "sufficiently devoid", as used herein refers to a composition of purified minicells that have a parental cell contamination level that has little or no effect on the toxicity profile and/or therapeutic effect of targeted therapeutic minicells.

The term "domain" or "protein domain" used herein refers to a region of a molecule or structure that shares common physical and/or chemical features. Non-limiting examples of protein domains include hydrophobic transmembrane or peripheral membrane binding regions, globular enzymatic or receptor regions, protein-protein interaction domains, and/or nucleic acid binding domains.

The terms "Eubacteria" and "prokaryote" are used herein as these terms are used by those in the art. The terms "eubacterial" and "prokaryotic" used herein encompass Eubacteria, including both Gram-negative and Gram-positive bacteria, prokaryotic viruses (e.g., bacteriophage), and obligate intracellular parasites (e.g., *Richettsia, Chlamydia*, etc.).

The term "immunopotentiating polypeptide" is synonomous with "immunostimulatory polypeptide" and "immunomodulatory polypeptide" and the terms are used interchangeably herein to refer to any collection of diverse protein molecule types that have an immunomodulatory effect when introduced into a eukaryotic organism or cell (e.g., a mammal such as human). An immunomodulatory polypeptide can be a cytokine, a chemokine, a cholesterol-dependent cytolysin, a functional enzyme, an antibody or antibody mimetic, an activated caspase, a pro-caspase, a cytokine, a chemokine, a cell-penetrating peptide, or any combination and/or plurality of the proceeding.

The terms "immunogen" and "antigen" are interchangeable and used herein to refer to polypeptides, carbohydrates, lipids, nucleic acids, and other molecules to which an antigen-specific antibody, cellular, and/or allergenic response may be mounted against. In the context of the present invention, "immunogenicity", synonomous with "antigenicity" of the minicell is not responsible for the immunotherapeutic effect. Antigen-specific immune responses rely on the presence of the antigen/immunogen, and are not be included in the definition of Th1 or Th2 immunomodulatory responses as used herein.

The term "overexpression" used herein refers to the expression of a functional nucleic acid, polypeptide or protein encoded by DNA in a host cell, wherein the nucleic acid, polypeptide or protein is either not normally present in the host cell, or wherein the nucleic acid, polypeptide or protein is present in the host cell at a higher level than that normally expressed from the endogenous gene encoding the nucleic acid, polypeptide or protein.

The term "modulate" as used herein means to interact with a target either directly or indirectly so as to alter the activity of the target to regulate a biological process. The mode of "modulate" includes, but is not limited to, enhancing the activity of the target, inhibiting the activity of the target, limiting the activity of the target, and extending the activity of the target.

The term "heterologous" as used herein refers to a protein, gene, nucleic acid, imaging agent, buffer component, or any other biologically active or inactive material that is not naturally found in a minicell or minicell-producing bacterial strain that is expressed, transcribed, translated, amplified or otherwise generated by minicell-producing bacterial strains that harbor recombinant genetic material coding for said heterologous material or coding for genes that are capable of producing said heterologous material (e.g., a bioactive metabolite not native to the parent cell).

The term "exogenous" as used herein refers to a protein (including antibodies), gene, nucleic acid, small molecule drug, imaging agent, buffer, radionuclide, or any other biologically active or inactive material that is not native to a cell, or in the case of a minicell, not native to the parent cell of the minicell. Exogenous material differs from heterologous material by virtue of the fact that it is generated, purified, and added separately.

The term "therapeutic" as used herein means having a biological effect or combination of biological effects that prevents, inhibits, eliminates, or prevents progression of a disease or other aberrant biological processes in an animal.

The term "diagnostic" as used herein means having the ability to detect, monitor, follow, and/or identify a disease or condition in an animal (including humans) or from a biological sample including but not limited to blood, urine, saliva, sweat and fecal matters.

The term "theranostic" as used herein means having the combined effects of a therapeutic and a diagnostic composition.

The term "recombinantly expressed" as used herein means the expression of one or more nucleic acid(s) and/or protein(s) from a nucleic acid molecule that is constructed using modern genetic engineering techniques wherein the constructed nucleic acid molecule does not occur naturally in minicells and/or minicell-producing bacterial strains wherein the artificial nucleic acid molecule is present as an episomal nucleic acid molecule or as part of the minicell-producing bacterial chromosome.

The term "episomal" as used herein means a nucleic acid molecule that is independent of the chromosome(s) of a given organism or cell.

The term "detoxified" as used herein refers to a modification made to a composition or component thereof that results in a significant reduction in acute toxicity to the modified composition or component thereof, regardless of what the causative biological basis for toxicity to the composition or component thereof happens to be.

As used herein, the term "bioactive molecule" refers to a molecule having a biological effect on a eukaryotic organism or cell (e.g., a mammal such as human) when introduced into the human organism or cell. Bioactive molecules include, but are not limited to, therapeutic nucleic acids, therapeutic polypeptides (including protein toxins), and therapeutic small molecule drugs.

Description

The present application relates to the use of bacterial minicells in vitro and in vivo to stimulate the immune system in such a way as to have an indirect anticancer effect mediated by said immune response. Eubacterial minicells have distinct advantage as immunomodulators, in that they mimic live bacteria but are not alive and are not infectious and therefore have reduced toxicity when compared to live bacterial immunomodulatory therapies. In addition, bacterial minicells may be genetically engineered such that contain different molecular constituents, each of which may preferentially enhance, invoke, or otherwise incite a certain type of immune response (i.e. Th1 versus Th2). Bacterial minicells disclosed herein are designed to generate immune responses that have indirect anticancer activity in addition to any direct anti-tumor activity. The minicells may also specifically target cell types or tissues known to be involved in the initiation, promotion, support, and maintenance of an immunological response in an animal. The present application provides use of bacterial minicells as non-living immunomodulatory therapies for cancer and other diseases.

Bacterial minicells are achromosomal, membrane-encapsulated biological nanoparticles (approximately 250-500 nm in diameter) that are formed by bacteria following a disruption in the normal division apparatus of bacterial cells. In essence, minicells are small, metabolically active replicas of normal bacterial cells with the exception that they contain no chromosomal DNA and as such, are non-dividing, non-viable, and non-infectious. Although minicells do not contain bacterial chromosomes, plasmid DNA molecules (smaller than chromosomes), RNA molecules (of all subtypes and structures), native and/or recombinantly expressed proteins, and other metabolites have all been shown to segregate into minicells. Minicells are uniquely suited as in vivo immunomodulators because they can be engineered to combine one or more different naturally occurring, heterologous, or exogenous immunomodulatory molecular components into a single particle where each component is present in discreet amounts. This is in stark contrast to live bacterial based immunotherapies where live bacteria are capable of continuing to divide, persist, and generate unknown quantities of immunomodulatory components de novo after administration in vivo. Persistence and propagation of living bacterial immunotherapies can lead to many different complications including infection, organ failure, sepsis, and death. In short, minicells can be "engineered" to preferentially encapsulate, be coupled to, or absorb biologically active molecules, including various nucleic acids, proteins, small molecule drugs, and any combination thereof for subsequent generation of immunomodulatory responses in both prophylactic and therapeutic medicinal applications where the prevention, maintenance, and/or inhibition of disease by way of said immunomodulatory response is desirable.

Genetically engineered bacterial minicells have been used directly as anti-cancer agents as described in U.S. Pat. No. 7,183,105, which is incorporated herein by reference in its entirety. For example, it has been taught within U.S. Pat. No. 7,183,105 that minicells can be engineered to use minicell surface-localized antibodies to target and deliver small molecule drugs, peptides, proteins, and various nucleic acids, together or in concert directly to cancer cells to exert a direct targeted anticancer effect. Other investigators have also reported the same findings as those taught in U.S. Pat. No. 7,183,105, with respect to the use of minicells as targeted delivery vehicles, as illustrated in U.S. Patent Publication Nos. 20070298056, 20080051469, and 20070237744, each of which is incorporated herein by reference. None of these references teach that minicells can be engineered and utilized as anti-cancer immunotherapies, capable of exerting indirect anti-tumor effects. Rather, each reference teaches the same approach of using minicells to specifically target and deliver anti-cancer agents only directly to tumor cells in vivo. The references included above collectively teach away from the use of bacterial minicells to cause non-immunogenic immunomodulatory effects when used as cancer therapeutics in vivo. For example, U.S. Pat. No. 7,183,105 describes several approaches that may be taken to lessen or evade immune responses including the use of minicells from L-form bacteria (containing no outer membrane) as well generating protoplasts (contain no outer membrane and no cell wall). Examples provided in U.S. Patent Publication Nos. 20070298056, 20080051469, and 20070237744 indicate that targeting, using an antibody selective for a known tumor selective cell surface receptor coupled to the surface of the minicell vehicle is required for anti-tumor activity. Further, these references also indicate that when non-targeted minicells are used, that no significant anti-tumor response is observed. In other related work, MacDiarmid and colleagues demonstrate that both non-targeted minicells and tumor-targeted minicells containing no cytotoxic drug payload, are equally incapable of generating an anti-tumor response and that both a targeting antibody and the cytotoxic payload are required (MacDiarmid, et al. *Cancer Cell,* 2007, Volume 11, p. 431-445). Additionally, MacDiarmid et al. discuss the benefits of evading the immune system, describe such evasion as part of their rationale for design, and therefore explicitly teach away from using minicells as immunomodulatory therapeutics. In contrast, the present disclosure provides, for example, the use of bacterial minicells as immunomodulatory therapeutics capable of eliciting potent, indirect, anti-tumor activity. For example, the minicells disclosed herein can be used to induce a non-immunogenic anti-tumor immunomodulatory effect in a subject.

In some embodiments, the present disclosure provides the use of bacterial minicells as immunomodulatory therapeutics capable of eliciting potent anti-tumor effects by simultaneous direct and indirect mechanisms mediated by direct tumor targeting and concomitant anti-tumor immunomodulatory effects, respectively. For example, the minicells can be designed to stimulate, non-specifically, an anti-cancer immune response while also working specifically, and in concert with said immune response, by also delivering a toxic payload directly to cancer cells. Thus, some embodiments of the present disclosure relates to direct killing of tumor cells and/or tumor endothelial cells by targeted drug delivery using minicells and by the indirect non-specific adjuvant effect involving activation of NK and other immune cell activities including but not limited to the release of cytokines typical of a Th1 response.

As disclosed herein, other live bacterial therapies have been employed as anti-cancer agents in the past but have been limited by toxicity due to their viable nature. The purveyors of these technologies claim that living bacterial therapies work by preferentially colonizing the hypoxic regions of tumors, invading tumor cells in the process, and causing further necrosis. Importantly, each of these technologies stresses the importance of having a live bacterial formulation to achieve efficacy and some go so far as to demonstrate the inactivity of killed bacterial therapies. These examples would not lead a skilled practitioner to utilize minicells, yet, rather to avoid doing so by teaching that bacterial viability, colonization of, and persistence within tumor tissue is paramount to efficacy. Minicells are not viable, do not persist and therefore, would not be expected to have an effect, given the teachings of those utilizing live bacterial therapies. In contrast to these teachings, the present disclosure makes use of self-limiting, non-living minicells, incapable of persisting in vivo, as an immunotherapy against cancer.

The immunomodulatory therapy disclosed herein may be used with any tumor type. One of ordinary skill in the art will appreciate that certain tumor types may be more susceptible and therefore potentially more amenable to this approach to therapy. For example, immunomodulatory therapy and minicells disclosed herein can be used to treat invasive bladder cancer. Over 300,000 new cases of bladder cancer are reported worldwide every year, 70% of which are detected early at the non-muscle invasive stage. This population is typically broken down into three stages of disease termed Ta, T1, and T is whereby the tumor is papillary (formerly referred to as superficial), has invaded the lamnia propria but not yet the muscle, and carcinoma in situ (flat non-invasive tumor), respectively. Each tumor type is then further broken down by grading (grades 1-3) based on different factors including proliferative index and the like. The standard of care for low risk disease, based on stage and grading, is transuretheral resection of bladder tumor (TURBT) followed by immediate post-operative administration of a chemotherapeutic agent. The recommended standard of care for intermediate risk patients is TURBT, followed by immediate postoperative installation of chemotherapy, followed by a 6 week induction treatment with chemotherapy. In the event the patient fails chemotherapy, a second cystoscopic resection is performed and the patient given a live attenuated strain of *Mycobacterium bovis*, Bacille Calmette-Guerin (BCG), 14 days later. The chemotherapeutic of choice for immediate postoperative installation is mytomycin C, although doxorubicin, epirubicin, valrubicin, paclitaxel, and gemcitabine have all been utilized with similar effect. In high risk disease, including those patients presenting with carcinoma in situ, BCG is the only effective agent. BCG immunomodulatory treatment is far superior to that of any of the chemotherapeutics employed to date in the intermediate and high risk population but it is limited in that it cannot be administered immediate postoperatively. The risk associated with systemic absorption of live BCG should the bladder be perforated during the TURBT procedure is too great to justify its use in the immediate postoperative setting, even though BCG-mediated immunomodulation is a far superior approach to chemotherapy with respect to observed recurrence rates. Therefore, most urologists tend to wait the 14 days to administer BCG, while foregoing the recommended immediate postoperative installation. On the other hand, outcomes, also in terms of recurrence, are much better if treatment is initiated using the immediate postoperative clinical treatment guidelines. Taken together, there is a clear need for a non-living immunomodulatory therapy that can be administered immediately postoperatively, unlike BCG, to patients having received TURBT for non-muscle invasive bladder cancer. Moreover, an estimated 30% of patients who receive BCG voluntarily halt therapy because of the toxic side effects. Toxicity has been demonstrated to be a function of BCG viability. Therefore, great need exists for a therapeutic agent that can impart the same immunomodulatory benefit of BCG, but without the risk of infection or the viability-associated toxicities.

In some embodiments, immunomodulatory minicells can be utilized as an intravesically administered immunotherapy in (i) the immediate postoperative setting in non-muscle invasive bladder cancer, (ii) in lieu of BCG therapy for induction and maintenance therapies of the same and (iii) as a salvage therapy for BCG-intolerant and BCG-refractory patients. In no way is this method of use meant to limit the present disclosure but rather to exemplify the need for effective, non-living, immunotherapies for use in cancer. In addition, the use of multi-effect integrin-targeted immunomodulatory minicells, which contain the integrin targeting moiety invasin on the minicell surface in conjunction with one or more combinations of encapsulated cytotoxic polypeptides, endosomal disrupting polypeptides, small molecule drugs, or nucleic acids, are of benefit in bladder cancer because they are capable of causing both direct tumor cell killing effects and tumor endothelial cell killing effects by way of integrin targeting and delivery, while still exerting additional indirect anti-tumor immunomodulatory effects commissioned by the immune system. One non-limiting application of multi-effect integrin-targeted cytotoxic immunomodulatory minicells in bladder cancer, is the use of VAX-IP, which is the minicell comprising surface-localized integrin targeting moiety invasin, and perfringolysin O. VAX-IP can be used as an immunomodulatory therapy and/or as a direct anti-tumor/tumor endothelial cell therapy. Another non-limiting application of multi-effect integrin-targeted cytotoxic immunomodulatory minicells in bladder cancer, is the use of VAX-IPD, which is the minicell comprising surface-localized integrin targeting moiety invasin, the catalytic fragment of diphtheria toxin, and perfringolysin O. VAX-IPD can be used as an immunomodulatory therapy and/or as a direct anti-tumor/tumor endothelial cell therapy.

In some embodiments, minicells are engineered and utilized to generate Th1-dominated immune responses. The Th1 immunomodulatory minicells are capable of generating the production of Th1 cytokines and chemokines including but not limited to IFN-γ, IFN-α, IL-12, IL-2, GMCSF, IL-18, TGF-β, and TNF-α.

The minicell disclosed herein, in some embodiments, comprises a cholesterol-dependent cytolysin protein. In some embodiments, the minicell does not display a molecule comprising an Fc region of an antibody. The molecule comprising an Fc region of an antibody can, for example, be an antibody or an antibody derivative. In some embodiments, the minicell does not comprise invasin. In some embodiments, the minicell does not comprise a therapeutic small molecule and/or a therapeutic nucleic acid. In some embodiments, the minicell also does not comprise any therapeutic protein other than a protein toxin, a Th1 cytokin, a Th2 cytokine, a phospholipase, and/or a cholesterol-dependent cytolysin protein. In some embodiments, the minicell does not comprise any therapeutically-active moiety other than a protein toxin, a Th1 cytokin, a Th2 cytokine, a phospholipase, and/or a cholesterol-dependent cytolysin protein. In some embodiments, the amount of cholesterol-dependent cytolysin protein on the minicell is at a level toxic to a mammalian cell when the minicell contacts said mammalian cell.

In some embodiments, Th1 immunomodulatory minicells include but are not limited to those produced from naturally invasive strains of bacteria, including but not limited, to invasive strains of *Salmonella* spp., *Listeria* spp., *Mycobacterium* spp., *Shigella* spp., *Yersinia* spp., and *Escherichia coli*. These naturally invasive Th1 immunomodulatory minicells will display naturally occurring minicell surface-localized ligands that are capable of stimulating internalization of minicells into eukaryotic cells, to aid in generating Th1-dominant immunotherapeutic responses. One of ordinary skill in the art will appreciate that naturally-invasive minicells do not exist in nature per se but rather are engineered from non-minicell producing invasive strains of bacteria using one or more of the genetic approaches to generating minicells as described herein.

In some embodiments, naturally invasive Th1 immunomodulatory minicells further comprise one or more recombinantly expressed proteins and nucleic acids designed to further enhance, modulate, or stabilize Th1-dominant immune responses. The recombinantly expressed proteins include, but are not limited to, Th1 cytokines such as IL-2, GMCSF, IL-12p40, IL-12p70, IL-18, TNF-α, and IFN-γ. In addition, naturally invasive Th1 immunomodulatory minicells may express one or more pore-forming cytolysin proteins, such as such as listeriolysin O (LLO) and any functional variants or equivalents thereof to facilitate endosomal escape of minicell constituents into the cytosol of cells that have internalized said minicells to enhance, modulate, or stabilize Th1-dominant immune responses mediated by said minicells. Phospholipases, such as PC-PLC or PI-PLC, can also be used as endosomal disrupting agents utilized to enhance, modulate, or stabilize Th1-dominant immune responses by enhancing minicell constituent release from the endosome into the cytosol of eukaryotic cells that have internalized said minicells. Naturally invasive Th1 immunomodulatory minicells can express a combination of one or more of a Th1 cytokine and one or more endosomal disrupting cytolysins. Naturally invasive Th1 immunomodulatory minicells may also contain recombinantly expressed protein toxins to promote necrosis and/or apoptosis which in turn can also further enhance, modulate, and/or stabilize Th1 immune responses. The preferred recombinantly expressed/produced protein toxin is perfringolysin O. Other recombinantly expressed/produced protein toxins to be utilized using naturally invasive Th1 immunomodulatory minicells include but are not limited to fragments A/B of diphtheria toxin, fragment A of diphtheria toxin, anthrax toxins LF and EF, adenylate cyclase toxin, gelonin, botulinolysin B, botulinolysin E3, botulinolysin C, botulinum toxin, cholera toxin, *Clostridium* toxins A, B and alpha, ricin, shiga A toxin, shiga-like A toxin, cholera A toxin, pertussis S1 toxin, *Pseudomonas* exotoxin A, *E. coli* heat labile toxin (LTB), melittin, pH stable variants of listeriolysin O (pH-independent; amino acid substitution L461T), thermostable variants of listeriolysin O (amino acid substitutions E247M, D320K), pH and thermostable variants of listeriolysin O (amino acid substitutions E247M, D320K, and L461T), streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin, activated caspases, pro-caspases, cytokines, chemokines, cell-penetrating peptides, and any combination of the preceding examples. Recombinant expression of polypeptides(s) can be the result of expression from any of the various episomal recombinant prokaryotic expression vectors known in the art including but not limited to plasmids, cosmids, phagemids, and bacterial artificial chromosomes (BACs), and any combination of the preceding examples. In similar fashion, recombinant expression can be achieved by a chromosomally located prokaryotic expression cassette present in one or more copies of the minicell-producing parent cell chromosome. Naturally invasive Th1 immunomodulatory minicells can also be engineered to express or contain one or more immunomodulatory nucleic acids known to stimulate endosome-localized Toll-like receptors 3, 7, 8, and/or 9 to enhance Th1 immunomodulatory effects. Such nucleic acids include but are not limited to single stranded DNA, single stranded RNA, double stranded DNA, double stranded RNA, DNA hairpins, and RNA hairpins, each of which can be recombinantly expressed as will be readily recognized by those skilled in the art. In some embodiments, naturally invasive Th1 immunomodulatory minicells are derived from a minicell-producing strain that harbors the homing endonuclease genetic suicide system of U.S. Patent Publication No. 20100112670, incorporated herein by reference. The I-ceuI homing endonuclease described therein selectively digests the chromosomes of most bacterial species at discreet conserved sites, serving on one hand to selectively kill parental cells and on the other to generate double stranded DNA fragments in the process.

Some embodiments provide a naturally invasive Th1 immunomodulatory minicell-producing bacterium comprising: (i) an expressible gene encoding a minicell-producing gene product that modulates one or more of septum formation, binary fission, and chromosome segregation; and (ii) a protein toxin capable of stimulating an immunotherapeutic effect, including but not limited to perfringolysin O. In some embodiments, the bacterium does not display an antibody or other molecule comprising an Fc region of an antibody and does not display the Fc binding portion of Protein G or Protein A. In some embodiments, the naturally invasive Th1 immunomodulatory minicell-producing bacterium further comprises one or more of (iii) an expressible "genetic suicide" gene encoding a heterologous endonuclease, where the chromosome of the naturally invasive Th1 immunomodulatory minicell-producing bacteria comprises one or more recognition sites of the endonuclease; (iv) a defined auxotrophy; and (v) a deletion or mutation in the lpxM/msbB gene (or other functional equivalent). In some embodiments, the minicell-producing gene is a cell division gene. Examples of the cell division gene include, but are not limited to ftsZ, sulA, ccdB, and sfiC. In some embodiments, the minicell-producing gene is expressed under the control of an inducible promoter. In some embodiments, the endonuclease suicide gene is located on the chromosome of the minicell-producing bacteria. In some embodiments, the endonuclease is a homing endonuclease. The homing endonuclease includes, but is not limited to, I-CeuI, PI-SceI, I-ChuI, I-CpaI, I-SceIII, I-CreI, I-MsoI, I-SceII, I-SceIV, I-CsmI, I-DmoI, I-PorI, PI-TliI, PI-TliII, and PI-ScpI. In some embodiments, the endonuclease is expressed under the control of an inducible promoter. In some embodiments, the auxotrophy is due to a deletion or inactivating mutation in an essential metabolic gene. In some embodiments, the deletion or inactivating mutation is in the dapA gene or its functional homolog. In some embodiments, the minicell-producing bacteria further comprises a deletion or an inactivating mutation in a gene encoding a gene product that is involved in lipopolysaccharide synthesis, wherein the gene is genetically modified compared to a corresponding wild-type gene. In some embodiments, the inactivated gene is lpxM/msbB which encodes a gene product that causes the bacteria to produce an altered lipid A molecule compared to lipid A molecules in a corresponding wild-type bacterium. In some embodiments, the altered lipid A molecule is deficient with respect to the addition of myristolic acid to the lipid A portion of the lipopolysaccharide molecule compared to lipid A molecules in a corresponding wild-type bacterium. In some embodiments, the minicell-producing bacteria further comprise a deletion or inactivating mutation in a gene that is involved in homologous recombination, where the gene is genetically modified compared to a corresponding wild-type gene, where the minicell-producing bacteria are deficient in DNA damage repair, reducing the risk of recovery from the genetic suicide mechanism. In some embodiments the naturally invasive Th1 immunomodulatory minicell-producing bacterium is a Gram-negative bacterium including but not limited to invasive strains of *Yersinia* spp., *Campylobacter* spp., *Pseudomonas* spp., *Salmonella* spp., *Shigella* spp., *Rickettsia* spp., and *Escherichia coli*. In some embodiments, the naturally invasive Th1 immunomodulatory minicell-producing bacterium is a Gram-positive bacterium including but not limited to *Mycobacterium* spp., *Streptococcus* spp., *Listeria monocytogenes, Chlamydia* spp., and *Brucella* spp.

Th1 immunomodulatory minicells include but are not limited to those produced from non-invasive strains of bacteria that have been genetically engineered to become invasive. Many non-invasive strains of bacteria are known to the skilled artisan and include but are not limited to non-invasive strains of *Escherichia coli, Salmonella* spp., *Shigella* spp., *Lactobacillus* spp., *Pseudomonas* spp., and the like. These normally non-invasive strains are genetically modified to display heterologous minicell surface-localized ligands capable of stimulating internalization of minicells into eukaryotic cells. The resulting recombinant invasive Th1 immunomodulatory minicells can be internalized by immune and other eukaryotic cells to generate Th1-dominant immunotherapeutic responses. In some embodiments, recombinant invasive Th1 immunomodulatory minicells further comprise one or more recombinantly expressed immunomodulatory proteins and nucleic acids designed to further enhance, modulate, or stabilize Th1-dominant immune responses. Examples of the immunomodulatory protein include but are not limited to Th1 cytokines such as IL-2, GMCSF, IL-12p40, IL-12p70, IL-18, TNF-α, and IFN-γ. Recombinant invasive Th1 immunomodulatory minicells may express one or more pore-forming cytolysin proteins, such as listeriolysin O (LLO) and any functional variants or equivalents thereof to facilitate endosomal escape of minicell constituents into the cytosol of cells that have internalized the minicells to enhance, modulate, or stabilize Th1-dominant immune responses mediated by the minicells. Phospholipases, such as PC-PLC or PI-PLC, can also be used as endosomal disrupting agents utilized to enhance, modulate, or stabilize Th1-dominant immune responses by enhancing minicell constituent release from the endosome into the cytosol of eukaryotic cells that have internalized the minicells. Recombinant invasive Th1 immunomodulatory minicells can express a combination of one or more of a Th1 cytokine and one or more endosomal disrupting cytolysins. Naturally invasive Th1 immunomodulatory minicells can also contain recombinantly expressed protein toxins to promote necrosis and/or apoptosis which in turn can also further enhance, modulate, and/or stabilize Th1 immune responses. The preferred recombinantly expressed/produced protein toxin is perfringolysin O. Other examples of recombinantly expressed/produced protein toxins that can be utilized using recombinant invasive Th1 immunomodulatory minicells include but are not limited to fragments A/B of diphtheria toxin, fragment A of diphtheria toxin, anthrax toxins LF and EF, adenylate cyclase toxin, gelonin, botulinolysin B, botulinolysin E3, botulinolysin C, botulinum toxin, cholera toxin, *Clostridium* toxins A, B and alpha, ricin, shiga A toxin, shiga-like A toxin, cholera A toxin, pertussis S1 toxin, *Pseudomonas* exotoxin A, *E. coli* heat labile toxin (LTB), melittin, pH stable variants of listeriolysin O (pH-independent; amino acid substitution L461T), thermostable variants of listeriolysin O (amino acid substitutions E247M, D320K), pH and thermostable variants of listeriolysin O (amino acid substitutions E247M, D320K, and L461T), streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin, activated caspases, pro-caspases, cytokines, chemokines, cell-penetrating peptides, and any combination of the preceding examples. Recombinant expression of polypeptides(s) can be the result of expression from any of the various episomal recombinant prokaryotic expression vectors known in the art including but not limited to plasmids, cosmids, phagemids, and bacterial artificial chromosomes (BACs), and any combination of the preceding examples. In similar fashion, recombinant expression can be achieved by a chromosomally located prokaryotic expression cassette present in one or more copies of the minicell-producing parent cell chromosome. Recombinant invasive Th1 immunomodulatory minicells can also be engineered to express or contain one or more immunomodulatory nucleic acids known to stimulate endosome-localized Toll-like receptors 3, 7, 8, and/or 9 to enhance Th1 immunomodulatory effects. Such nucleic acids include but are not limited to single stranded DNA, single stranded RNA, double stranded DNA, linear double stranded DNA, double stranded RNA, DNA hairpins, and RNA hairpins, each of which can be recombinantly expressed as will be readily recognized by those skilled in the art. In some embodiments, recombinant invasive Th1 immunomodulatory minicells are derived from a minicell-producing strain that harbors the homing endonuclease genetic suicide system of U.S. Patent Publication No. 2010-0112670, which is incorporated herein by reference. The I-CeuI homing endonuclease described therein selectively digests the chromosomes of most bacterial species at discreet, conserved sites, serving on one hand to selectively kill parental cells, and on the other, to generate double stranded linear DNA fragments in the process.

Some embodiments provide a recombinant invasive Th1 immunomodulatory minicell-producing bacterium comprising: (i) an expressible gene encoding a minicell-producing gene product that modulates one or more of septum formation, binary fission, and chromosome segregation; (ii) a recombinant expression cassette capable of the functional expression and surface display of one or more heterologous minicell surface-localized targeting moieties capable of stimulating internalization into eukaryotic cells, and (iii) a protein toxin capable of stimulating an immunotherapeutic effect, including but not limited to perfringolysin O. The recombinant invasive Th1 immunomodulatory minicell-producing bacterium can also include, in some embodiments, one or more of (iv) an expressible "genetic suicide" gene encoding a heterologous endonuclease, where the chromosome of the minicell-producing bacteria comprises one or more recognition sites of the endonuclease; (v) a defined auxotrophy; and (vi) a deletion or mutation in the lpxM/msbB gene (or other functional equivalent). In some embodiments, the minicell-producing gene is a cell division gene. The cell division gene includes, but is not limited to ftsZ, sulA, ccdB, and sfiC. In some embodiments, the minicell-producing gene is expressed under the control of an inducible promoter. In some embodiments, the endonuclease suicide gene is located on the chromosome of the minicell-producing bacteria. In some embodiments, the endonuclease is a homing endonuclease. The homing endonuclease includes, but is not limited to, I-CeuI, PI-SceI, I-ChuI, I-CpaI, I-SceIII, I-CreI, I-MsoI, I-SceII, I-SceIV, I-CsmI, I-DmoI, I-PorI, PI-TliI, PI-TliII, and PI-ScpI. In some embodiments, the endonuclease is expressed under the control of an inducible promoter. In some embodiments, the auxotrophy is due to a deletion or inactivating mutation in an essential metabolic gene. In some embodiments, the deletion or inactivating mutation is in the dapA gene or its functional homolog. In some embodiments, the minicell-producing bacteria further comprises a deletion or an inactivating mutation in a gene encoding a gene product that is involved in lipopolysaccharide synthesis, wherein the gene is genetically modified compared to a corresponding wild-type gene. In some embodiments, the inactivated gene is lpxM/msbB which encodes a gene product that causes the bacteria to produce an altered lipid A molecule compared to lipid A molecules in a corresponding wild-type bacterium. In some embodiments, the altered lipid A molecule is deficient with respect to the addition of myristolic acid to the lipid A portion of the lipopolysaccharide molecule compared to lipid A molecules in a corresponding wild-type bacterium. In some embodiments, the minicell-producing bacteria further comprise a deletion or inactivating mutation in a gene that is involved in homologous recombination, where the gene is genetically modified compared to a corresponding wild-type gene, where the minicell-producing bacteria are deficient in DNA damage repair. In some embodiments, the recombinant invasive Th1 immunomodulatory minicell-producing bacterium is a Gram-negative bacterium including but not limited to *Campylobacter jejuni, Haemophilus influenzae, Bordetella pertussis, Brucella* spp., *Franciscella tularemia, Legionella pneumophilia, Neisseria meningitidis, Kliebsella, Yersinia* spp., *Helicobacter pylori, Neisseria gonorrhoeae, Legionella pneumophila, Salmonella* spp., *Shigella* spp., *Pseudomonas* spp., and *Escherichia coli*. In some embodiments, the recombinant invasive Th1 immunomodulatory minicell-producing bacterium is a Gram-positive bacterium including but not limited to *Staphylococcus* spp., *Lactobacillus* spp., *Streptococcus* spp., *Bacillus subtilis, Clostridium difficile*, and *Bacillus cereus*.

In some embodiments, Th1 immunomodulatory minicells are produced from non-invasive strains of bacteria. Many non-invasive strains of bacteria are known to the skilled artisan and include but are not limited to non-invasive strains of *Escherichia coli, Salmonella* spp., *Shigella* spp., *Lactobacillus* spp., *Pseudomonas* spp., and the like. These non-invasive Th1 immunomodulatory minicells can be internalized by immune and other eukaryotic cells to generate Th1-dominant immunotherapeutic responses. In some embodiments, recombinant non-invasive Th1 immunomodulatory minicells further comprise one or more recombinantly expressed immunomodulatory proteins and nucleic acids designed to further enhance, modulate, or stabilize Th1-dominant immune responses. Examples of the immunomodulatory protein include but are not limited to Th1 cytokines such as IL-2, GMCSF, IL-12p40, IL-12p70, IL-18, TNF-α, and IFN-γ. Recombinant non-invasive Th1 immunomodulatory minicells may express one or more pore forming cytolysin proteins, such as such as listeriolysin O (LLO) and any functional variants or equivalents thereof to facilitate endosomal escape of minicell constituents into the cytosol of cells that have internalized said minicells to enhance, modulate, or stabilize Th1-dominant immune responses mediated by said minicells. Phospholipases, such as PC-PLC or PI-PLC, can also be used as endosomal disrupting agents utilized to enhance, modulate, or stabilize Th1-dominant immune responses by enhancing minicell constituent release from the endosome into the cytosol of eukaryotic cells that have internalized said minicells. Recombinant non-invasive Th1 immunomodulatory minicells can express a combination of one or more of a Th1 cytokine and one or more endosomal disrupting cytolysins. Recombinant non-invasive Th1 immunomodulatory minicells can also contain recombinantly expressed protein toxins to promote necrosis and/or apoptosis which in turn can also further enhance, modulate, and/or stabilize Th1 immune responses. The preferred recombinantly expressed/produced protein toxin is perfringolysin O. Other recombinantly expressed/produced protein toxins to be utilized using recombinant non-invasive Th1 immunomodulatory minicells include but are not limited to fragments A/B of diphtheria toxin, fragment A of diphtheria toxin, anthrax toxins LF and EF, adenylate cyclase toxin, gelonin, botulinolysin B, botulinolysin E3, botulinolysin C, botulinum toxin, cholera toxin, *Clostridium* toxins A, B and alpha, ricin, shiga A toxin, shiga-like A toxin, cholera A toxin, pertussis S1 toxin, *Pseudomonas* exotoxin A, *E. coli* heat labile toxin (LTB), melittin, pH stable variants of listeriolysin O (pH-independent; amino acid substitution L461T), thermostable variants of listeriolysin O (amino acid substitutions E247M, D320K), pH and thermostable variants of listeriolysin O (amino acid substitutions E247M, D320K, and L461T), streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin, activated caspases, pro-caspases, cytokines, chemokines, cell-penetrating peptides, and any combination of the preceding examples. Recombinant expression of polypeptides(s) can be the result of expression from any of the various episomal recombinant prokaryotic expression vectors known in the art including but not limited to plasmids, cosmids, phagemids, and bacterial artificial chromosomes (BACs), and any combination of the preceding examples. In similar fashion, recombinant expression can be achieved by a chromosomally located prokaryotic expression cassette present in one or more copies of the minicell-producing parent cell chromosome. Recombinant non-invasive Th1 immunomodulatory minicells can also be engineered to express or contain one or more immunomodulatory nucleic acids known to stimulate endosome-localized Toll-like receptors 3, 7, 8, and/or 9 to enhance Th1 immunomodulatory effects. Such nucleic acids include but are not limited to single stranded DNA, single stranded RNA, double stranded DNA, linear double stranded DNA, double stranded RNA, DNA hairpins, and RNA hairpins, each of which can be recombinantly expressed as will be readily recognized by those skilled in the art. In some embodiments, recombinant non-invasive Th1 immunomodulatory minicells are derived from a minicell-producing strain that harbors the homing endonuclease genetic suicide system described in U.S. Patent Publication No. 2010-0112670, incorporated herein by way of reference. The I-CeuI homing endonuclease described therein selectively digests the chromosomes of most bacterial species at discreet, conserved sites, serving on one hand to selectively kill parental cells, and on the other, to generate double stranded linear DNA fragments in the process.

Some embodiments provide a recombinant non-invasive Th1 immunomodulatory minicell-producing bacterium comprising: (i) an expressible gene encoding a minicell-producing gene product that modulates one or more of septum formation, binary fission, and chromosome segregation; and (ii) a protein toxin capable of stimulating an immunotherapeutic effect, including but not limited to perfringolysin O. In some embodiments, the recombinant non-invasive Th1 immunomodulatory minicell-producing bacterium further comprises one or more of (iii) an expressible "genetic suicide" gene encoding a heterologous endonuclease, where the chromosome of the recombinant non-invasive Th1 immunomodulatory minicell-producing bacteria comprises one or more recognition sites of the endonuclease; (iv) a defined auxotrophy; and and (v) a deletion or mutation in the lpxM/msbB gene (or other functional equivalent). In some embodiments, the minicell-producing gene is a cell division gene. The cell division gene includes, but is not limited to ftsZ, sulA, ccdB, and sfiC. In some embodiments, the minicell-producing gene is expressed under the control of an inducible promoter. In some embodiments, the endonuclease suicide gene is located on the chromosome of the minicell-producing bacteria. In some embodiments, the endonuclease is a homing endonuclease. Examples of the homing endonuclease include, but are not limited to, I-CeuI, PI-SceI, I-ChuI, I-CpaI, I-SceIII, I-CreI, I-MsoI, I-SceII, I-SceIV, I-CsmI, I-DmoI, I-PorI, PI-TliI, PI-TliII, and PI-ScpI. In some embodiments, the endonuclease is expressed under the control of an inducible promoter. In some embodiments, the auxotrophy is due to a deletion or inactivating mutation in an essential metabolic gene. In some embodiments the deletion or inactivating mutation is in the dapA gene or its functional homolog. In some embodiments, the minicell-producing bacteria further comprises a deletion or an inactivating mutation in a gene encoding a gene product that is involved in lipopolysaccharide synthesis, wherein the gene is genetically modified compared to a corresponding wild-type gene. In some embodiments, the inactivated gene is lpxM/msbB which encodes a gene product that causes the bacteria to produce an altered lipid A molecule compared to lipid A molecules in a corresponding wild-type bacterium. In some embodiments, the altered lipid A molecule is deficient with respect to the addition of myristolic acid to the lipid A portion of the lipopolysaccharide molecule compared to lipid A molecules in a corresponding wild-type bacterium. In some embodiments, the minicell-producing bacteria further comprise a deletion or inactivating mutation in a gene that is involved in homologous recombination, where the gene is genetically modified compared to a corresponding wild-type gene, where the minicell-producing bacteria are deficient in DNA damage repair, reducing the risk of recovery from the genetic suicide mechanism. In some embodiments, the recombinant non-invasive Th1 immunomodulatory minicell-producing bacterium is a Gram-negative bacterium including but not limited to invasive strains of *Yersinia* spp., *Campylobacter* spp., *Pseudomonas* spp., *Salmonella* spp., *Shigella* spp., *Rickettsia* spp., and *Escherichia coli*. In some embodiments the recombinant non-invasive Th1 immunomodulatory minicell-producing bacterium is a Gram-positive bacterium including but not limited to *Mycobacterium* spp., *Streptococcus* spp., *Listeria monocytogenes, Chlamydia* spp., and *Brucella* spp.

In some embodiments, minicells are engineered and utilized to generate Th2-dominated immune responses. Examples of the Th2 immunomodulatory minicell capable of generating the production of Th2 cytokines and chemokines include, but are not limited to, IL-1α, IL-1β, IL-4, IL-5, IL-6, IL-10, and IL-13.

In some embodiments, Th2 immunomodulatory minicells include but are not limited to those produced from naturally occurring non-invasive, adherent, or muco-adhesive strains of bacteria including but not limited to non-invasive, adherent, and muco-adhesive strains of *Streptococcus* spp., *Staphylococcus* spp., *Salmonella* spp., *Shigella* spp., *Lactobacillus* spp., *Pseudomonas* spp., *Klebsiella* spp., and *Escherichia coli*. These naturally non-invasive Th2 immunomodulatory minicells do not display naturally occurring minicell surface-localized ligands that are capable of stimulating internalization of minicells into eukaryotic cells, though they may be engulfed by constitutively phagocytic immune cells such as macrophages, dendritic cells, and neutrophils. Adherent and muco-adherent Th2 immunomodulatory minicells express minicell surface localized proteins that can stimulate adherence to the surfaces of eukaryotic cells and mucosal surfaces, respectively, yet do not cause appreciable internalization, the exception being for normally constitutively phagocytic cells such as macrophages, neutrophils, and dendritic cells. One of ordinary skill in the art will appreciate that naturally-noninvasive Th2 immunomodulatory minicells, adherent Th2 immunomodulatory minicells, and muco-adherent Th2 immunomodulatory minicells do not exist in nature per se but rather are engineered from non-minicell producing non-invasive, adherent, and muco-adherent species of bacteria using one or more of the genetic approaches to generating minicells as described herein. Non-adherent strains of *Streptococcus* spp., *Staphylococcus* spp., *Salmonella* spp., *Shigella* spp., *Lactobacillus* spp., *Pseudomonas* spp., *Klebsiella* spp., and *Escherichia coli* are easily engineered by those skilled in the art of molecular biology and/or microbial genetics to become adherent by cloning and recombinant expression of bacterial cell surface adherence factors such that expression of said heterologous adherence factors results in recombinant adherent Th2 immunomodulatory minicells.

Some embodiments provide a naturally non-invasive, adherent, or muco-adherent Th2 immunomodulatory minicell-producing bacterium comprising: (i) an expressible gene encoding a minicell-producing gene product that modulates one or more of septum formation, binary fission, and chromosome segregation. In some embodiments, the naturally non-invasive, adherent, or muco-adherent Th2 immunomodulatory minicell-producing bacterium further comprises one or more of (ii) an expressible "genetic suicide" gene encoding a heterologous endonuclease, where the chromosome of the naturally non-invasive, adherent, and/or muco-adherent Th2 immunomodulatory minicell-producing bacteria comprises one or more recognition sites of the endonuclease; (iii) a defined auxotrophy; and (iv) a deletion or mutation in the lpxM/msbB gene (or other functional equivalent. In some embodiments, the minicell-producing gene is a cell division gene. The cell division gene includes, but is not limited to ftsZ, sulA, ccdB, and sfiC. In some embodiments, the minicell-producing gene is expressed under the control of an inducible promoter. In some embodiments, the endonuclease suicide gene is located on the chromosome of the minicell-producing bacteria. In some embodiments, the endonuclease is a homing endonuclease. Examples of the homing endonuclease include, but are not limited to, I-CeuI, PI-SceI, I-ChuI, I-CpaI, I-SceIII, I-CreI, I-MsoI, I-SceII, I-SceIV, I-CsmI, I-DmoI, I-PorI, PI-TliI, PI-TliII, and PI-ScpI. In some embodiments, the endonuclease is expressed under the control of an inducible promoter. In some embodiments, the auxotrophy is due to a deletion or inactivating mutation in an essential metabolic gene. In some embodiments, the deletion or inactivating mutation is in the dapA gene or its functional homolog. In some embodiments, the minicell-producing bacteria further comprises a deletion or an inactivating mutation in a gene encoding a gene product that is involved in lipopolysaccharide synthesis, wherein the gene is genetically modified compared to a corresponding wild-type gene. In some embodiments, the inactivated gene is lpxM/msbB which encodes a gene product that causes the bacteria to produce an altered lipid A molecule compared to lipid A molecules in a corresponding wild-type bacterium. In some embodiments, the altered lipid A molecule is deficient with respect to the addition of myristolic acid to the lipid A portion of the lipopolysaccharide molecule compared to lipid A molecules in a corresponding wild-type bacterium. In some embodiments, the minicell-producing bacteria further comprise a deletion or inactivating mutation in a gene that is involved in homologous recombination, where the gene is genetically modified compared to a corresponding wild-type gene, where the minicell-producing bacteria are deficient in DNA damage repair, reducing the risk of recovery from the genetic suicide mechanism. In some embodiments the naturally non-invasive, adherent, and/or muco-adherent Th2 immunomodulatory minicell-producing bacterium is a Gram-negative bacterium including but not limited to invasive strains of *Yersinia* spp., *Campylobacter* spp., *Pseudomonas* spp., *Salmonella* spp., *Shigella* spp., *Rickettsia* spp., and *Escherichia coli*. In some embodiments, the naturally non-invasive, adherent, or muco-adherent Th2 immunomodulatory minicell-producing bacterium is a Gram-positive bacterium including but not limited to *Mycobacterium* spp., *Streptococcus* spp., *Listeria monocytogenes, Chlamydia* spp., and *Brucella* spp.

Some embodiments provide multi-effect targeted cytotoxic immunomodulatory minicells. Multi-effect targeted cytotoxic immunomodulatory minicells contain a minicell surface localized targeting moiety, a cytotoxic payload, and/or endosomal escape protein. Multi-effect targeted cytotoxic immunomodulatory minicells are capable of eliciting direct anti-tumor effects by way of targeting and delivering a cytotoxic payload directly to tumor cells in addition to being able to evoke a Th1 immunomodulatory effect that results in further anti-tumor activity.

As described herein, VAX-IP minicells encompass all multi-effect cytotoxic immunomodulatory minicells that express and display invasin and perfringolysin O in concert. It is preferred that the final preparation of minicells is comprised of detoxified LPS and is sufficiently devoid of any in vivo viable contaminating parent cells by virtue of the novel, inducible genetic suicide mechanism and DAP auxotrophy.

As described herein, VAX-IPT minicells encompass all multi-effect cytotoxic immunomodulatory minicells that express and display invasin, perfringolysin O, and a protein toxin in concert. It is preferred that the final preparation of minicells is comprised of detoxified LPS and is sufficiently devoid of any in vivo viable contaminating parent cells by virtue of the novel, inducible genetic suicide mechanism and DAP auxotrophy.

As described herein, one non-limiting preferred sub-class of VAX-IPT minicell is VAX-IPD minicell, which is a multi-effect cytotoxic immunomodulatory minicell expressing and displaying invasin, perfringolysin O, and the catalytic fragment (fragment A) of diphtheria toxin in concert. It is preferred that the final preparation of minicells is comprised of detoxified LPS and is sufficiently devoid of any in vivo viable contaminating parent cells by virtue of a novel, inducible genetic suicide mechanism and DAP auxotrophy. In some embodiments, VAX-IPD bacterial minicells are used to target and more efficiently deliver the catalytic fragment of diphtheria toxin in vitro and in vivo. For example, optimal killing activity is observed in the presence of all three of invasin, PFO, and the catalytic fragment (fragment A) of diphtheria toxin. And, VAX-IPD has similar requirements for all three components in order to exert broad spectrum potency across a panel of murine and human endothelial and tumor cell types known to express activated beta1 integrins. Surprisingly, HL60 cells which are also known to express beta1 integrins, are not affected by VAX-IPD. This result is unexpected and upon further review of the literature, it was discovered that HL60 cells express beta1 integrins but in an unactivated form. However, invasin activity, which has been thoroughly characterized, has never been reported to be dependent on beta1 activation status per se. This unexpected result is likely also contributing to the lack of expected toxicity demonstrated in vivo as beta1 integrins are expressed in many tissue types, albeit in most instances at very low levels, and are also found in ligand bound or unactivated form. Importantly, it is observed that VAX-IPD minicells are capable of preventing or eliminating metastases as well as exerting primary anti-tumor effects in vivo. Similar results, with respect to activity and toxicity, albeit in a different model, are also observed.

Protein G is a cell-surface protein expressed by the Gram-positive bacterium Group G *Streptococcus*. Its natural biological function is to prevent opsonization of Group G *Streptococcus* during the infection process by binding the Fc region of antibodies such that the Fc region is masked from the immune system. Protein G contains two Fc binding domains. In some embodiments, the minicells does not have the Fc binding portion of protein G. In some embodiments, the minicells does not display the Fc binding portion of protein G.

Protein A is a cell-surface protein expressed by the Gram-positive bacterium *Staphylococcus aureus*. Like Protein G, its natural biological function is also to prevent opsonization of *Staphylococcus aureus* during the infection process. *Staphylococcus aureus* use Protein A to bind to the Fc region of antibodies. Protein A contains four discreet Fc binding domains. In some embodiments, the minicells does not have the Fc binding portion of protein A. In some embodiments, the minicells does not display the Fc binding portion of protein A.

The minicells disclosed herein, in some embodiments, do not comprise an antibody or other molecule comprising an Fc region of an antibody. The minicells disclosed herein, in some embodiments, do not display an antibody or other molecule comprising an Fc region of an antibody.

Some embodiments provide a VAX-P minicell-producing bacterium comprising: (i) an expressible gene encoding a minicell-producing gene product that modulates one or more of septum formation, binary fission, and chromosome segregation; and (ii) a recombinant expression cassette capable of the functional expression of perfringolysin O. In some embodiments, the bacterium does not display an antibody or other molecule comprising an Fc region of an antibody and does not display the Fc binding portion of Protein G or Protein A. In some embodiments, the VAX-P minicell-producing bacterium further comprises one or more of (iii) an expressible "genetic suicide" gene encoding a heterologous endonuclease, where the chromosome of the minicell-producing bacteria comprises one or more recognition sites of the endonuclease; (iv) a defined auxotrophy; and (v) a deletion or mutation in the lpxM/msbB gene (or other functional equivalent). In some embodiments, the minicell-producing gene is a cell division gene. Examples of the cell division gene include, but are not limited to ftsZ, sulA, ccdB, and sfiC. In some embodiments, the minicell-producing gene is expressed under the control of an inducible promoter. In some embodiments, the endonuclease suicide gene is located on the chromosome of the minicell-producing bacteria. In some embodiments, the endonuclease is a homing endonuclease. Examples of the homing endonuclease include, but are not limited to, I-CeuI, PI-SceI, I-ChuI, I-CpaI, I-SceIII, I-CreI, I-MsoI, I-SceII, I-SceIV, I-CsmI, I-DmoI, I-PorI, PI-TliI, PI-TliII, and PI-ScpI. In some embodiments, the endonuclease is expressed under the control of an inducible promoter. In some embodiments, the auxotrophy is due to a deletion or inactivating mutation in an essential metabolic gene. In some embodiments, the deletion or inactivating mutation is in the dapA gene or its functional homolog. In some embodiments, the minicell-producing bacteria further comprises a deletion or an inactivating mutation in a gene encoding a gene product that is involved in lipopolysaccharide synthesis, wherein the gene is genetically modified compared to a corresponding wild-type gene. In some embodiments, the inactivated gene is lpxM/msbB which encodes a gene product that causes the bacteria to produce an altered lipid A molecule compared to lipid A molecules in a corresponding wild-type bacterium. In some embodiments, the altered lipid A molecule is deficient with respect to the addition of myristolic acid to the lipid A portion of the lipopolysaccharide molecule compared to lipid A molecules in a corresponding wild-type bacterium. In some embodiments, the minicell-producing bacteria further comprise a deletion or inactivating mutation in a gene that is involved in homologous recombination, where the gene is genetically modified compared to a corresponding wild-type gene, where the minicell-producing bacteria are deficient in DNA damage repair. In some embodiments the VAX-P minicell-producing bacterium is a Gram-negative bacterium including but not limited to *Campylobacter jejuni, Haemophilus influenzae, Bordetella pertussis, Brucella* spp., *Franciscella tularemia, Legionella pneumophilia, Neisseria meningitidis, Kliebsella, Yersinia* spp., *Helicobacter pylori, Neisseria gonorrhoeae, Legionella pneumophila, Salmonella* spp., *Shigella* spp., *Pseudomonas aeruginosa*, and

*Escherichia coli*. In some embodiments, the VAX-P minicell-producing bacterium is a Gram-positive bacterium including but not limited to *Staphylococcus* spp., *Lactobacillus* spp., *Streptococcus* spp., *Bacillus subtilis, Clostridium difficile*, and *Bacillus cereus*.

Some embodiments provide a VAX-IP minicell-producing bacterium comprising: (i) an expressible gene encoding a minicell-producing gene product that modulates one or more of septum formation, binary fission, and chromosome segregation; and (ii) a recombinant expression cassette capable of the functional expression and surface display of invasin in addition to expression of perfringolysin O. In some embodiments, the bacterium does not display an antibody or other molecule comprising an Fc region of an antibody and does not display the Fc binding portion of Protein G or Protein A. In some embodiments, the VAX-IP minicell-producing bacterium further comprises one or more of (iii) an expressible "genetic suicide" gene encoding a heterologous endonuclease, where the chromosome of the minicell-producing bacteria comprises one or more recognition sites of the endonuclease; (iv) a defined auxotrophy; and (v) a deletion or mutation in the lpxM/msbB gene (or other functional equivalent). In some embodiments, the minicell-producing gene is a cell division gene. Examples of the cell division gene include, but are not limited to ftsZ, sulA, ccdB, and sfiC. In some embodiments, the minicell-producing gene is expressed under the control of an inducible promoter. In some embodiments, the endonuclease suicide gene is located on the chromosome of the minicell-producing bacteria. In some embodiments, the endonuclease is a homing endonuclease. Examples of the homing endonuclease include, but are not limited to, I-CeuI, PI-SceI, I-ChuI, I-CpaI, I-SceIII, I-CreI, I-MsoI, I-SceII, I-SceIV, I-CsmI, I-DmoI, I-PorI, PI-TliI, PI-TliII, and PI-ScpI. In some embodiments, the endonuclease is expressed under the control of an inducible promoter. In some embodiments, the auxotrophy is due to a deletion or inactivating mutation in an essential metabolic gene. In some embodiments, the deletion or inactivating mutation is in the dapA gene or its functional homolog. In some embodiments, the minicell-producing bacteria further comprises a deletion or an inactivating mutation in a gene encoding a gene product that is involved in lipopolysaccharide synthesis, wherein the gene is genetically modified compared to a corresponding wild-type gene. In some embodiments, the inactivated gene is lpxM/msbB which encodes a gene product that causes the bacteria to produce an altered lipid A molecule compared to lipid A molecules in a corresponding wild-type bacterium. In some embodiments, the altered lipid A molecule is deficient with respect to the addition of myristolic acid to the lipid A portion of the lipopolysaccharide molecule compared to lipid A molecules in a corresponding wild-type bacterium. In some embodiments, the minicell-producing bacteria further comprise a deletion or inactivating mutation in a gene that is involved in homologous recombination, where the gene is genetically modified compared to a corresponding wild-type gene, where the minicell-producing bacteria are deficient in DNA damage repair. In some embodiments the VAX-IP minicell-producing bacterium is a Gram-negative bacterium including but not limited to *Campylobacter jejuni, Haemophilus influenzae, Bordetella pertussis, Brucella* spp., *Franciscella tularemia, Legionella pneumophilia, Neisseria meningitidis, Kliebsella, Yersinia* spp., *Helicobacter pylori, Neisseria gonorrhoeae, Legionella pneumophila, Salmonella* spp., *Shigella* spp., *Pseudomonas aeruginosa*, and *Escherichia coli*. In some embodiments, the VAX-IP minicell-producing bacterium is a Gram-positive bacterium including but not limited to *Staphylococcus* spp., *Lactobacillus* spp., *Streptococcus* spp., *Bacillus subtilis, Clostridium difficile*, and *Bacillus cereus*.

Some embodiments provide a VAX-IPD minicell-producing bacterium comprising: (i) an expressible gene encoding a minicell-producing gene product that modulates one or more of septum formation, binary fission, and chromosome segregation; and (ii) a recombinant expression cassette capable of the functional expression and surface display of invasin in addition to expression of perfringolysin O and the catalytic fragment (fragment A) of diphtheria toxin. In some embodiments, the bacterium does not display an antibody or other molecule comprising an Fc region of an antibody and does not display the Fc binding portion of Protein G or Protein A. In some embodiments, the VAX-IPD minicell-producing bacterium further comprises one or more of (iii) an expressible "genetic suicide" gene encoding a heterologous endonuclease, where the chromosome of the minicell-producing bacteria comprises one or more recognition sites of the endonuclease; (iv) a defined auxotrophy; and (v) a deletion or mutation in the lpxM/msbB gene (or other functional equivalent). In some embodiments, the minicell-producing gene is a cell division gene. Examples of the cell division gene include, but are not limited to ftsZ, sulA, ccdB, and sfiC. In some embodiments, the minicell-producing gene is expressed under the control of an inducible promoter. In some embodiments, the endonuclease suicide gene is located on the chromosome of the minicell-producing bacteria. In some embodiments, the endonuclease is a homing endonuclease. Examples of the homing endonuclease include, but are not limited to, I-CeuI, PI-SceI, I-ChuI, I-CpaI, I-SceIII, I-CreI, I-MsoI, I-SceII, I-SceIV, I-CsmI, I-DmoI, I-PorI, PI-TliI, PI-TliII, and PI-ScpI. In some embodiments, the endonuclease is expressed under the control of an inducible promoter. In some embodiments, the auxotrophy is due to a deletion or inactivating mutation in an essential metabolic gene. In some embodiments, the deletion or inactivating mutation is in the dapA gene or its functional homolog. In some embodiments, the minicell-producing bacteria further comprises a deletion or an inactivating mutation in a gene encoding a gene product that is involved in lipopolysaccharide synthesis, wherein the gene is genetically modified compared to a corresponding wild-type gene. In some embodiments, the inactivated gene is lpxM/msbB which encodes a gene product that causes the bacteria to produce an altered lipid A molecule compared to lipid A molecules in a corresponding wild-type bacterium. In some embodiments, the altered lipid A molecule is deficient with respect to the addition of myristolic acid to the lipid A portion of the lipopolysaccharide molecule compared to lipid A molecules in a corresponding wild-type bacterium. In some embodiments, the minicell-producing bacteria further comprise a deletion or inactivating mutation in a gene that is involved in homologous recombination, where the gene is genetically modified compared to a corresponding wild-type gene, where the minicell-producing bacteria are deficient in DNA damage repair. In some embodiments the VAX-IPD minicell-producing bacterium is a Gram-negative bacterium including but not limited to *Campylobacter jejuni, Haemophilus influenzae, Bordetella pertussis, Brucella* spp., *Franciscella tularemia, Legionella pneumophilia, Neisseria meningitidis, Kliebsella, Yersinia* spp., *Helicobacter pylori, Neisseria gonorrhoeae, Legionella pneumophila, Salmonella* spp., *Shigella* spp., *Pseudomonas aeruginosa*, and *Escherichia coli*. In some embodiments, the VAX-IPD minicell-producing bacterium is a Gram-positive bacterium including but not limited to *Staphylococcus* spp., *Lactobacillus* spp., *Streptococcus* spp., *Bacillus subtilis, Clostridium difficile*, and *Bacillus cereus.*

Figure 8:
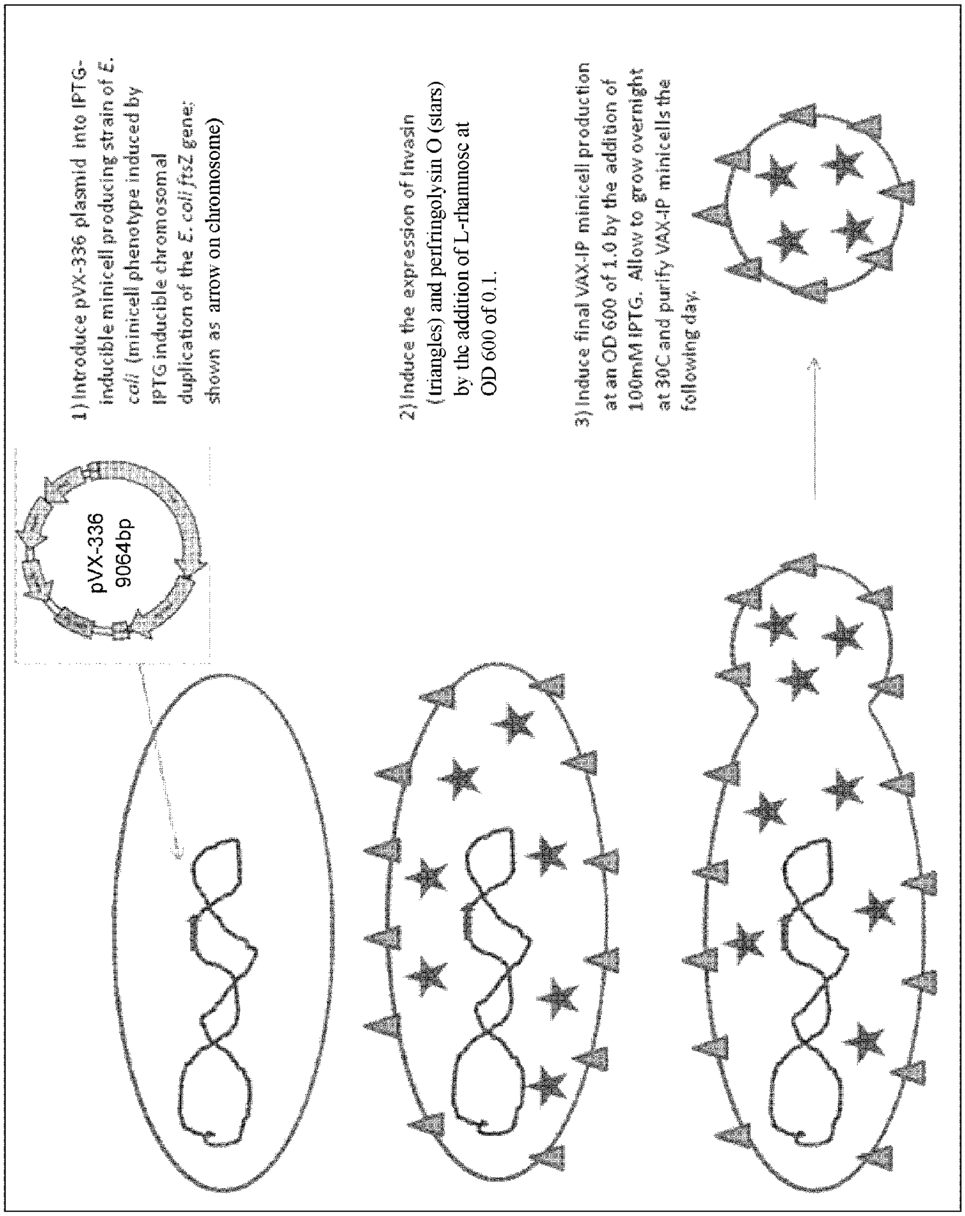
FIG. 8 is a schematic illustration for a general scheme of construction of VAX-IP minicell-producing strains and VAX-IP minicells therefrom.

Minicells have distinct mechanisms and advantages with respect to loading of immunomodulatory polypeptides (e.g. cytokines, protein toxins, and cytolysins) and nucleic acids (e.g. double stranded RNA, hairpin RNA, double stranded linear DNA). For example, immunomodulatory minicell-producing parental bacterial cells can be used to recombinantly express/produce one or more cytokines, protein toxins, and cytolysins prior to or at the same time that minicells are being produced. Recombinant polypeptides are expressed, segregate into, and are encapsulated by minicells, and then utilized to enhance, modulate, and/or stabilize Th1 or Th2 immune responses elicited by immunomodulatory minicells in vivo. The recombinant production of various immunomodulatory minicell protein components, can include but is not limited to, perfringolysin O and invasin, can be facilitated by any combination of recombinant expression methods known to the skilled artisan. By way of non-limiting example, recombinant expression can be facilitated from a chromosomally located operably linked open reading frame coding for a particular protein component, such as invasin. Recombinant expression of protein components of immunomodulatory minicells can be facilitated by the use of one or more episomal prokaryotic expression constructs such as plasmids, cosmids, phagemids, and bacterial artificial chromosomes (BACs). Operably linked prokaryotic open reading frames coding for the individual desired protein components of the final immunomodulatory minicell product can be present on the same episomal expression construct or on separate and distinct episomal expression constructs. The production of the desired protein components can be placed under inducible prokaryotic promoter control or alternatively can be placed under the control of a constitutively active prokaryotic promoter system. One of ordinary skill in the art will readily recognize the prokaryotic promoter systems available for use with the present invention. Examples of promoter system include but are not limited to the IPTG inducible Lac system and its myriad derivatives, the L-rhamnose inducible pRHA system, the L-arabinose inducible pBAD system, the T7 polymerase system, the CI857ts system, and the like. One non-limiting embodiment of generating VAX-IP minicell-producing strains and VAX-IP minicells there from, is illustrated in Example 6 and FIG. 8.

In cases where polypeptide(s) are pre-formed by the parental cell by way of recombinant expression from a prokaryotic expression cassette (either chromosomal or episomal in location) and then packaged inside of the minicells as an immunopotentiator, the half-life of the polypeptide(s) within the minicell can be increased by use of immunomodulatory minicell producing bacterial strains harboring one or more deletions or other non-functional mutations in protease genes (e.g., the lon protease of *E. coli*) responsible for proteolysis. In the absence of the protease(s), the protein toxin molecules accumulate to a higher level, increasing the potency of targeted minicells delivering the therapeutic polypeptide molecules. In the case of *Escherichia coli* minicell producing strains, mutation or deletions can be introduced into one or more of the lon, tonB, abgA, ampA, ampM, pepP, clpP, dcp, ddpX/vanX, elaD, frvX, gcp/b3064, hslV, hchA/b1967, hyaD, hybD, hycH, hycI, iadA, ldcA, ycbZ, pepD, pepE, pepQ, pepT, pmbA, pqqL, prlG, ptrB, sgcX, sprT, tldD, ycaL, yeaZ, yegQ, ygeY, yggG, yhbO, yibG, ydpF, degS, ftsH/hflB, glpG, hofD/hopD, lepB, lspA, pppA, sohB, spa, yaeL, yfbL, dacA, dacB, dacC, degP/htrA, degQ, iap, mepA, nlpC, pbpG, tsp, ptrA, teas, umuD, ydcP, ydgD, ydhO, yebA, yhbU, yhjJ, and nlpD genes.

In cases where immunomodulatory nucleic acid(s) are pre-formed by the parental cell by way of recombinant expression from a prokaryotic expression cassette (either chromosomal or episomal in location) and then packaged inside of the minicells as an immunopotentiator, the half-life of the nucleic acid(s) within the minicell is increased by use of immunomodulatory minicell producing bacterial strains harboring one or more deletions or other non-functional mutations in nuclease genes (e.g., the mc nuclease of *E. coli*) responsible for double stranded RNA degradation. In the absence of the nuclease(s), immunomodulatory nucleic acid molecules accumulate to a higher level, increasing the potency of immunomodulatory minicells harboring said immunomodulatory nucleic acid molecules.

In order for immunomodulatory minicells to be used as immunotherapeutic agents in humans, said minicells should contain few or no contaminants, such as viable parental bacterial cells. Levels of viable contaminating cells and other contaminants must be low enough not to cause adverse side effects in patients or to interfere with minicell activity. The inducible expression of a homing endonuclease gene, referred to as a genetic suicide mechanism, is a preferred mechanism by which to eliminate live contaminating parental cells, especially when used in combination with conventional filtration methods. Because minicells are derived from some bacteria that are pathogenic or opportunistically pathogenic, it is desirable that the contaminating parental cells be functionally eliminated from a given population before systemic, and particularly intravenous, administration. The same holds true for intravesical administration to non-muscle invasive bladder cancer patients having received TURBT surgery, especially where a perforation in the bladder has occurred or is suspected. Consequently, the desired minicell formulation would be one in which the residual live parental cell count would be as low as possible so as not cause adverse side effects or interfere with intended minicell activity. To maximize safety and limit toxicity due to viability of any contaminating parental cells, the minicells disclosed herein are derived from minicell-producing strains that comprise safety features, for example, one or more of the three safety features disclosed below. In some embodiments, the minicell-producing strains comprise at least these three synergistic safety features. The first is a genetic suicide mechanism that kills residual live parental cells without lysing them (and expelling free lipopolysaccharide) after the minicell formation step has been completed. The present application incorporates the use of a regulated genetic suicide mechanism that upon exposure to the appropriate inducer, introduces irreparable damage to the chromosomes of minicell-producing parental cells as described in U.S. Patent Publication No. 20100112670. The suicide mechanism operates to introduce irreparable double-stranded breaks to the chromosome of the parental cells and can be used as an adjunct to conventional separation techniques to improve minicell purification. The second safety feature is a defined auxotrophy, preferably but not necessarily in the diaminopimelic acid (DAP) biosynthesis pathway, and most preferably in the dapA gene of an *E. coli* minicell-producing strain. Minicell-producing strains of *E. coli* that exhibit DAP auxotrophy (dapA-) cannot survive outside of the laboratory without supplementation of DAP. Further, DAP is not found in mammals, including humans, and as such any minicell-producing parental cell that is present in the minicell product will not be able to survive in the environment or in vivo. Many variations on this theme exist for different Gram-negative and Gram-positive bacteria. For example in *Salmonella*, spp., auxotrophies in the aromatic amino acid biosynthesis pathways (the aro genes) produce in effect, the same result. In the case of *Shigella* spp. auxotrophies in the guanine biosynthesis pathway will produce, in effect, the same result. The third safety feature is optional and entails a deletion of the lpxM gene in *E. coli* minicell-producing strains. Deletion of the lpxM gene can result in the production of de-toxified lipopolysaccharide (LPS) molecules. The lpxM gene (also referred to as the msbB gene) functions to add a terminal myristolic acid group to the lipid A portion of the LPS molecule and removal of this group (by way of elimination of the lpxM gene) results in marked detoxification of LPS. Specifically, detoxification is characterized by a decrease in the production of pro-inflammatory cytokines in response to exposure to LPS. One of ordinary skill in the art will appreciate that cytokines are still made using the detoxified form of LPS. The detoxification controls only the levels of cytokines produced, making it possible to dampen the acute sepsis-like pro-inflammatory response while allowing more robust Th1 and/or Th2 immune responses, to be achieved without overt toxicity. This deletion can be introduced into any functionally equivalent gene of any Gram-negative or Gram-positive minicell-producing strain to achieve the same effect. The enhanced safety profile can reduce the risk of infection and potential for developing sepsis, decrease the possibility of genetic reversion through recombination events with other bacteria, and minimize the risk of insertion events in the host. From a regulatory and manufacturing perspective, it is also preferred that antibiotic resistance markers be eliminated from the bacterial chromosome of the minicell-producing parental cell strain. The use of most antibiotic resistance gene markers in minicell-producing strains of bacteria is undesirable in order to comply with regulatory requirements imposed by the U.S. Food and Drug Administration (FDA) for use in humans. The FDA will only tolerate the use of the kanamycin resistance gene marker for selection purposes for bacteria or bacterial production strains wherein the final product is intended for use in humans.

Some embodiments provide a method of making immunomodulatory minicells, comprising culturing the appropriate immunomodulatory minicell-producing bacteria disclosed herein and substantially separating immunomodulatory minicells from the minicell-producing parent cells, thereby generating a composition comprising immunotherapeutic minicells. In some embodiments, the method further comprises inducing immunomodulatory minicell formation from a culture of minicell-producing parent cells. In some embodiments, the method further comprises inducing expression of the gene encoding the genetic suicide endonuclease. In some embodiments, minicell formation is induced by the presence of one or more chemical compounds selected from isopropyl β-D-1-thiogalactopyranoside (IPTG), rhamnose, arabinose, xylose, fructose, melibiose, and tetracycline. In some embodiments, the expression of the gene encoding the genetic suicide endonuclease is induced by a change in temperature. In some embodiments, the method further comprises purifying the immunomodulatory minicells from the composition. In some embodiments, the immunomodulatory minicells are substantially separated from the parent cells by a process selected from the group including but not limited to centrifugation, filtration, ultrafiltration, ultracentrifugation, density gradation, immunoaffinity, immunoprecipitation, and any combination of the preceding purification methods.

Some embodiments provide a eubacterial minicell comprising an outer membrane, where the lipopolysaccharide constituents of the outer membrane comprises Lipid A molecules having no myristolic acid moiety ("detoxified lipopolysaccharide" or "detoxified LPS"). Detoxified LPS results in the reduction of pro-inflammatory immune responses in a mammalian host compared to the inflammatory response induced by the outer membrane of eubacterial minicells that are derived from a corresponding wild-type bacterium.

The present disclosure describes the novel use of immunomodulatory eubacterial minicells for purposes of stimulating the immune system in such a way as to have potent indirect anti-tumor effects mediated, in full or in part, by the immune response in addition to any direct anti-tumor effects. For example, the immunomodulatory minicells disclosed herein can be used as an intravesical therapy for non-muscle invasive bladder cancer.

1. Minicell Production

Minicells are achromosomal, membrane-encapsulated biological nano-particles (approximately 250-500 nm in diameter depending on the strain type and growth conditions used) that are formed by bacteria following a disruption in the normal cell division apparatus. In essence, minicells are small, metabolically active replicas of normal bacterial cells with the exception that they contain no chromosomal DNA and as such, are non-dividing and non-viable. Although minicells do not contain chromosomal DNA, plasmid DNA, RNA, native and/or recombinantly expressed proteins, and other metabolites have all been shown to segregate into minicells.

Disruptions in the coordination between chromosome replication and cell division lead to minicell formation from the polar region of most rod-shaped prokaryotes. Disruption of the coordination between chromosome replication and cell division can be facilitated through the over-expression of some of the genes involved in septum formation and binary fission. Alternatively, minicells can be produced in strains that harbor mutations in genes involved in septum formation and binary fission. Impaired chromosome segregation mechanisms can also lead to minicell formation as has been shown in many different prokaryotes.

Similarly, minicell production can be achieved by the over-expression or mutation of genes involved in the segregation of nascent chromosomes into daughter cells. For example, mutations in the parC or mukB loci of *E. coli* have been demonstrated to produce minicells. Both affect separate requisite steps in the chromosome segregation process in Enterobacteriacea. It can be assumed that like the cell division genes described above, manipulation of wild type levels of any given gene involved in the chromosome segregation process that result in minicell production will have similar effects in other family members.

Because the cell division and chromosome replication processes are so critical to survival, there exists a high level of genetic and functional conservation amongst prokaryotic family members with respect to genes responsible for these processes. As a result, the over-expression or mutation of a cell division gene capable of driving minicell production in one family member can be used to produce minicells in another. For example, it has been shown that the over-expression of the *E. coli* ftsZ gene in other Enterobacteriacea family members such as *Salmonella* spp. and *Shigella* spp as well as other class members such as *Pseudomonas* spp. will result in similar levels of minicell production.

The same can be demonstrated in the mutation-based minicell producing strains of the family Enterobacteriacea.

For example, deletion of the min locus in any of Enterobacteriacea family members results in minicell production. Cell division genes from the Enterobacteriacea in which mutation can lead to minicell formation include but are not limited to the min genes (MinCDE). While minicell production from the min mutant strains is possible, these strains have limited commercial value in terms of being production strains. The reason for this is that strains with deletions or mutations within the min genes make minicells at constitutively low levels. This presents two problems in terms of commercialization and economies of scale. The first is that minicell yields from these strains are low, which increases production cost. The second is that minicell yields are highly variable with the mutant strains and lot-to-lot variability has an enormous impact on production cost, manufacturing quality control and regulatory compliance. Using cell division mutant strains to produce minicells that encapsulate biologically active molecules such as proteins, RNA, DNA, and other catabolites for diagnostic or therapeutic delivery is problematic. The onset of minicell production in the mutant strains cannot be controlled and occurs at a low level so that the end result is that some minicells will contain no biologically active molecules while others will contain widely variable amounts of biologically active molecules. These shortcomings when taken together or separately greatly restrict the utility of these mutant strains for commercial purposes.

Minicell-producing strains that overexpress cell division genes ("overexpressers") are preferred over mutation-based strains because the minicell-production phenotype is controllable as long as the cell division genes to be overexpressed are placed under the control of an inducible or other conditionally active eubacterial promoter system. Minicell production from strains overexpressing the cell division gene ftsZ were discovered by researchers who were identifying essential cell division genes in *E. coli* using plasmid-based complementation studies. In these studies, the ftsZ gene was present in over 10 copies per cell. The presence of multiple gene copies of ftsZ was demonstrated to produce minicells and extremely long filamented cells. Ultimately, this transition into the irreversible filamentous phenotype negatively impacts minicell yields from strains overexpressing ftsZ from multi-copy plasmids, although the number of minicells produced is still higher than that of any mutant strain. It has since been demonstrated that by reducing the number of ftsZ gene copies to a single, chromosomal duplication, the number of minicells produced increases over those strains where ftsZ is located on multi-copy plasmids and that the filamentous phenotype is less profound. Thus, the preferred composition(s) are minicell-producing strains that inducibly overexpress the ftsZ gene from a duplicate, chromosomally integrated copy of ftsZ. The duplicate ftsZ gene used can be derived directly from the species of bacteria in which the minicell-production phenotype is being engineered and can also be derived from the ftsZ gene sequence from other species of bacteria. By way of non-limiting example, overexpression of the ftsZ gene of *Escherichia coli* can be used to generate minicells from *Escherichia coli* and *Salmonella typhimurium*. Resulting strains are comprised of the wild type ftsZ gene and a separate, duplicative, and inducible copy of the ftsZ gene on the chromosome and the inducible genetic suicide mechanism(s) described in U.S. patent publication No. 2010/0112670, which is incorporated herein by its entirety. By way of non-limiting example, division genes that can be over-expressed to produce minicells in the family Enterobacteriaceae include but are not limited to ftsZ, minE, sulA, ccdB, and sfiC. The preferred composition is to have a duplicate copy(s) of a cell division gene(s) under the control of an inducible promoter that is stably integrated into the chromosome of a given eubacterial strain. It is easily recognized by one skilled in the art that this same strategy could be imparted if the inducible cell division gene cassette were present on a plasmid, cosmid, bacterial artificial chromosome (BAC), recombinant bacteriophage or other episomal DNA molecule present in the cell.

This inducible phenotype approach to minicell production has several distinct advantages over the mutant systems. The first is that because there are no constitutive genetic mutations in these strains, there exists no selective pressure during normal growth and the cells of the culture maintain a very stable and normal physiology until the minicell phenotype is induced. The end result is that inducible minicell producing strains are healthier and more stable, which ultimately results in higher yields of minicells. Another distinct advantage of using the inducible phenotype approach to minicell production is in cases where minicells are to be used to deliver biologically active molecules such as proteins, therapeutic RNAs, plasmid DNAs, and other bioactive catabolites that can be made by the minicell-producing parent cells such that the minicells that are produced encapsulate those biologically active molecules. In these cases, the preferred method is to induce the formation of the biologically active molecule(s) within the parental cells prior to inducing the minicell phenotype, so that all of the minicells produced will contain the desired amount of the biologically active molecule(s). Alternatively, the minicells themselves are capable of producing the bioactive molecule after being separated from the parental cells. This includes but is not limited to forming the bioactive molecule from an episomal nucleic acid or RNA encoding for the bioactive molecule located within the minicell or by preexisting protein constituents of minicells after being separated from the parental cells. Any of these expression strategies can be employed to express and display binding moieties on the surfaces of minicells. These advantages, when used in combination, result in a higher quality and quantity of minicells. In addition, these minicells can further comprise small molecule drugs that can be loaded into minicells as described in more detail below.

2. Minicell Purification

Because minicells are derived from some bacteria that are pathogenic or opportunistically pathogenic, it is of the utmost importance that any contaminating parental cells be functionally eliminated from a given population before administration. Conventionally, live parental cells have been eliminated through either physical means or biological means or both.

Physical means include the use of centrifugation-based separation procedures, filtration methodologies, chromatography methodologies, or any combination thereof.

Biological elimination is achieved by but not limited to the preferential lysis of parental cells, the use of auxotrophic parental strains, treatment with antibiotics, treatment with UV radiation, diaminopimelic acid (DAP) deprivation, selective adsorption of parental cells, treatment with other DNA damaging agents, and induction of a suicide gene.

Preferential lysis of parental cells is typically mediated by inducing the lytic cycle of a lysogenic prophage. In the case of minicell producing strains, it is most useful to use a prophage that is lysis competent but defective at re-infection, such that minicells are not subsequently infected and lysed during activation of the lytic phenotype. Alternatively and by way of non-limiting example, individual genes such as those classified as members of the holin gene family, can be expressed to achieve similar levels of lysis without the concerns over re-infection inherent to the use of lysogenic prophages. Both approaches are limited by the fact that the lysis event, regardless of the method used to achieve it, expels unacceptable amounts of free endotoxin into the media. Removal of such large amounts of free endotoxin is time consuming, suffers from lot to lot variability, and is ultimately cost prohibitive.

The use of auxotrophic strains raises concerns over reversion and as such can only be used in cases where minicells are to be produced from commensal or non-pathogenic strains of bacteria. Thus, their application is limited with respect to being used as a method for elimination of live non-pathogenic parental cells used in minicell production.

Treatment with UV irradiation can be useful in the elimination of live parental cells on a minicell production run with the exception of the fact that UV irradiation is random with respect to its effects on nucleic acids and results are highly variable from lot to lot. In addition, this method is not preferred when using minicells to deliver therapeutic or prophylactic nucleic acids as UV irradiation randomly damages all nucleic acids. For instance, plasmid DNA would also be highly susceptible to DNA damage by UV irradiation and may be rendered ineffective although still effectively delivered by minicells.

Diaminopimelic acid (DAP) deprivation can be useful in the elimination of live parental cells with the exception that this approach is limited by the number of species it can be used for. In other words, not all parent cell species capable of producing minicells require DAP for survival. DAP mutants in *E. coli* minicell-producing strains are of great advantage and in some cases preferred over the wild type. The advantage of using DAP is that this compound (diaminopimelic acid, an *E. coli* cell wall constituent) is critical for the growth of *E. coli* and is not present in or produced by animals. Thus, should a "viable" *E. coli* minicell-producing parental cell be administered along with targeted minicells, the parental cell will be unable to grow and will thereby be inert to the animal and with respect to minicell activity. A similar approach can be used with *Salmonella* spp. based minicell-producing parental strains except in that case the aro genes, preferably aroB are removed.

Selective adsorption methodologies have yet to be explored with respect to purifying minicells from viable parental cells. Selective adsorption is defined as any process by which parental cells or minicells are preferentially adsorbed to a substrate by virtue of their affinity for the substrate. By way of non-limiting example, high affinity protein-protein interactions could be exploited for this use. By way of non-limiting example, the novel minicell outer membrane protein Lpp-OmpA::Protein A has a high affinity for the Fc region of most antibodies. The gene encoding for Lpp-OmpA::Protein A is under the control an inducible promoter could easily be introduced on to the chromosome of an immunomodulatory minicell producing strain. Immunomodulatory minicells could be produced from this strain prior to the activation of expression of the invasin gene such that the minicells produced do not express or display Lpp-OmpA::Protein A on their cell surface. Once the desired quantity of immunomodulatory minicells is produced from the strain, the viable cells within the culture could be given the signal to produce the Lpp-OmpA::Protein A protein such that Lpp-OmpA::Protein A is only expressed and displayed upon viable cells. Once Lpp-OmpA::Protein A is preferentially expressed on the surface of viable parental cells, they can be easily adsorbed to a substrate coated with antibodies or other Fc-region containing proteins. Once absorbed, minicells can be selectively purified away from viable parental cells by a number of different means dependent upon the substrate type used. Substrates include but are not limited to solid-phase chromatographic columns used in gravity filtration applications, magnetic beads, ion exchange columns, or HPLC columns.

In some embodiments, minicells are substantially separated from the minicell-producing parent cells in a composition comprising minicells. For example, after separation, the composition comprising the minicells is more than about 99.9%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 65%, 60%, 55%, 50%, 45%, 40%, 35% or 30% free of minicell-producing parent cells. In some embodiments, the composition contains less than about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% minicell-producing parent cells.

Preferably, the final composition contains few enough contaminating parental cells, viable or otherwise, so as not to be too toxic or interfere with the activity of targeted minicells when administered in vivo for therapeutic purposes.

A preferred method of sufficiently eliminating contaminating viable parental bacterial cells or preventing their survival in vivo is through the incorporation of an inducible genetic suicide mechanism, including but not limited to the activation and expression of a homing endonuclease or functional equivalent thereof as described in U.S. Patent Publication No. 20100112670.

3. Targeting Minicells to Specific Cells, Tissues, and Organs

Following production and subsequent purification, VAX-IP, VAX-IPT, VAX-IPP, VAX-IPD, VAX-IPG, VAX-IPPA, and VAX-IPR minicells can be used as targeted delivery vehicles to target specific cell types that have elevated expression and/or activity of beta1-integrins and are involved in disease in vivo to preferentially and more efficiently deliver their protein toxin payloads to the targeted tissue, organ, and cell type. The targeted VAX-IP, VAX-IPT, VAX-IPP, VAX-IPD, VAX-IPG, VAX-IPPA, and VAX-IPR minicells disclosed herein can be targeted to eukaryotic cancer cell-specific surface antigens that include but are not limited to integrin $\alpha3\beta1$, integrin $\alpha4\beta1$, integrin $\alpha5\beta1$, integrin $\alpha6\beta1$, integrin $\alpha_v\beta1$, and integrin $\beta1$. As described in more detail below, expression and/or activity levels of these beta1 integrin family members are found in many solid tumor types as well as in the tumor vasculature as compared to low level, unactivated, and/or ligand occupied beta1 integrins in normal tissues and vasculature.

4. Loading Payloads into Minicells

Eubacterial minicells are capable of encapsulating and delivering several classes of biologically active compounds that have therapeutic, prophylactic, or diagnostic benefit to an animal. Types of the biologically active compounds (payloads) that can be delivered by minicells include but are not limited to small molecules (including small molecule drugs), nucleic acids, polypeptides, radioisotope, lipids, lipopolysaccharides, and any combination thereof.

Proteins are comprised of polypeptides and are encoded by DNA. Proteins can be biologically functional, such as enzymes, toxins, or signaling proteins. Proteins can be structural, such as is the case for actin and the like. Proteins can bind tightly to other proteins, such as with antibodies and antibody mimetics, and be used to disrupt functions requiring protein/protein interactions. Proteins can provide localization signals by being fluorescent or bioluminescent. Proteins can serve as immunogens or serve other therapeutic purposes (such as supplying or restoring enzyme in a target cell, tissue, organ, or animal). Proteins can aid in the post-endocytosis intracellular transfer of other payload types. For example, proteins such as listeriolysin O from *Listeria monocytogenes* can be employed to facilitate the transfer of the minicell payload(s) from the endocytotic compartment(s) of a target cell to the cytosol of a target cell. Proteins can also be pro-drug converting enzymes. One non-limiting preferred recombinantly expressed/produced protein toxin is perfringolysin O. Other recombinantly expressed/produced therapeutic polypeptides to be delivered by targeted minicells include but are not limited to protein toxins, cholesterol-dependent cytolysins, functional enzymes, antibody mimetics, protein/protein interaction disrupters, activated caspases, pro-caspases, cytokines, chemokines, cell-penetrating peptides, and any combination of the proceeding. Recombinant expression of a therapeutic polypeptide(s) can be the result of expression from any of the various episomal recombinant prokaryotic expression vectors known in the art including but not limited to plasmids, cosmids, phagemids, and bacterial artificial chromosomes (BACs), and any combination of the preceding. In similar fashion, recombinant expression can be achieved by a chromosomally located prokaryotic expression cassette present in one or more copies of the minicell-producing parent cell chromosome. The recombinant production of various immunomodulatory minicell protein components (including but not limited to perfringolysin O and invasin) can be facilitated by any combination of recombinant expression methods known to the skilled artisan. By way of non-limiting example, recombinant expression can be facilitated from a chromosomally located operably linked open reading frame coding for a particular protein component, such as invasin. Recombinant expression of protein components of immunomodulatory minicells can be facilitated by the use of one or more episomal prokaryotic expression constructs such as plasmids, cosmids, phagemids, and bacterial artificial chromosomes (BACs). Operably linked prokaryotic open reading frames coding for the individual desired protein components of the final immunomodulatory minicell product can be present on the same episomal expression construct or on separate and distinct episomal expression constructs. The production of the desired protein components can be placed under inducible prokaryotic promoter control or alternatively may be placed under the control of a constitutively active prokaryotic promoter system. One of ordinary skill in the art will readily recognize the prokaryotic promoter systems available for use. Examples of promoter systems include but are not limited to the IPTG inducible Lac system and its myriad derivatives, the L-rhamnose inducible pRHA system, the L-arabinose inducible pBAD system, the T7 polymerase system, the CI857ts system, and the like. By way of non-limiting example, the specific methods of generating VAX-IP minicell-producing strains and VAX-IP minicells there from, is included as Example 6 and FIG. 8.

Examples of protein toxins include but are not limited to perfringolysin O, gelonin, diphtheria toxin fragment A, diphtheria toxin fragment A/B, tetanus toxin, *E. coli* heat labile toxin (LTI and/or LTII), cholera toxin, *C. perfringes* iota toxin, *Pseudomonas* exotoxin A, shiga toxin, anthrax toxin, MTX (*B. sphaericus* mosquilicidal toxin), streptolysin, barley toxin, mellitin, anthrax toxins LF and EF, adenylate cyclase toxin, botulinolysin B, botulinolysin E3, botulinolysin C, botulinum toxin A, cholera toxin, *Clostridium* toxins A, B, and alpha, ricin, shiga A toxin, shiga-like A toxin, cholera A toxin, pertussis S1 toxin, *E. coli* heat labile toxin (LTB), pH stable variants of listeriolysin O (pH-independent; amino acid substitution L461T), thermostable variants of listeriolysin O (amino acid substitutions E247M, D320K), pH and thermostable variants of listeriolysin O (amino acid substitutions E247M, D320K, and L461T), streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin. Protein toxins may be localized to different sub-cellular compartments of the minicell at the discretion of the artisan. When targeted minicells disclosed herein are derived from a Gram-negative parental minicell-producing strain, recombinantly expressed therapeutic polypeptides produced therefrom can be localized to the cytosol, the inner leaflet of the inner membrane, the outer leaflet of the inner membrane, the periplasm, the inner leaflet of the outer membrane, the outer membrane of minicells, and any combination of the proceeding. When targeted minicells disclosed herein are derived from a Gram-positive parental minicell-producing strain, recombinantly expressed therapeutic polypeptides produced therefrom can be localized to the cytosol, the cell wall, the inner leaflet of the membrane, the membrane of minicells, and any combination of the proceeding.

5. Pharmaceutical Compositions

The present application also relates to compositions, including but not limited to pharmaceutical compositions. The term "composition" used herein refers to a mixture comprising at least one carrier, preferably a physiologically acceptable carrier, and one or more minicell compositions. The term "carrier" used herein refers to a chemical compound that does not inhibit or prevent the incorporation of the biologically active peptide(s) into cells or tissues. A carrier typically is an inert substance that allows an active ingredient to be formulated or compounded into a suitable dosage form (e.g., a pill, a capsule, a gel, a film, a tablet, a microparticle (e.g., a microsphere), a solution; an ointment; a paste, an aerosol, a droplet, a colloid or an emulsion etc.). A "physiologically acceptable carrier" is a carrier suitable for use under physiological conditions that does not abrogate (reduce, inhibit, or prevent) the biological activity and properties of the compound. For example, dimethyl sulfoxide (DMSO) is a carrier as it facilitates the uptake of many organic compounds into the cells or tissues of an organism. Preferably, the carrier is a physiologically acceptable carrier, preferably a pharmaceutically or veterinarily acceptable carrier, in which the minicell composition is disposed.

A "pharmaceutical composition" refers to a composition wherein the carrier is a pharmaceutically acceptable carrier, while a "veterinary composition" is one wherein the carrier is a veterinarily acceptable carrier. The term "pharmaceutically acceptable carrier" or "veterinarily acceptable carrier" used herein includes any medium or material that is not biologically or otherwise undesirable, i.e., the carrier may be administered to an organism along with a minicell composition without causing any undesirable biological effects or interacting in a deleterious manner with the complex or any of its components or the organism. Examples of pharmaceutically acceptable reagents are provided in The United States Pharmacopeia, The National Formulary, United States Pharmacopeial Convention, Inc., Rockville, Md. 1990, hereby incorporated by reference herein into the present application. The terms "therapeutically effective amount" and "pharmaceutically effective amount" refer to an amount sufficient to induce or effectuate a measurable response in the target cell, tissue, or body of an organism. What constitutes a therapeutically effective amount will depend on a variety of factors, which the knowledgeable practitioner will take into account in arriving at the desired dosage regimen.

The compositions can also comprise other chemical components, such as diluents and excipients. A "diluent" is a chemical compound diluted in a solvent, preferably an aqueous solvent, that facilitates dissolution of the composition in the solvent, and it may also serve to stabilize the biologically active form of the composition or one or more of its components. Salts dissolved in buffered solutions are utilized as diluents in the art. For example, preferred diluents are buffered solutions containing one or more different salts. An unlimiting example of preferred buffered solution is phosphate buffered saline (particularly in conjunction with compositions intended for pharmaceutical administration), as it mimics the salt conditions of human blood. Since buffer salts can control the pH of a solution at low concentrations, a buffered diluent rarely modifies the biological activity of a given compound or pharmaceutical composition.

An "excipient" is any more or less inert substance that can be added to a composition in order to confer a suitable property, for example, a suitable consistency or to produce a drug formulation. Suitable excipients and carriers include, in particular, fillers such as sugars, including lactose, sucrose, mannitol, or sorbitol cellulose preparations such as, for example, maize starch, wheat starch, rice starch, agar, pectin, xanthan gum, guar gum, locust bean gum, hyaluronic acid, casein potato starch, gelatin, gum tragacanth, methyl cellulose, hydroxypropylmethyl-cellulose, polyacrylate, sodium carboxymethylcellulose, and/or polyvinylpyrrolidone (PVP). If desired, disintegrating agents can also be included, such as cross-linked polyvinyl pyrrolidone, agar, or alginic acid or a salt thereof such as sodium alginate. Other suitable excipients and carriers include hydrogels, gellable hydrocolloids, and chitosan. Chitosan microspheres and microcapsules can be used as carriers. See e.g., WO 98/52547 (which describes microsphere formulations for targeting compounds to the stomach, the formulations comprising an inner core (optionally including a gelled hydrocolloid) containing one or more active ingredients, a membrane comprised of a water insoluble polymer (e.g., ethylcellulose) to control the release rate of the active ingredient(s), and an outer layer comprised of a bioadhesive cationic polymer, for example, a cationic polysaccharide, a cationic protein, and/or a synthetic cationic polymer; U.S. Pat. No. 4,895,724. Typically, chitosan is cross-linked using a suitable agent, for example, glutaraldehyde, glyoxal, epichlorohydrin, and succinaldehyde. Compositions employing chitosan as a carrier can be formulated into a variety of dosage forms, including pills, tablets, microparticles, and microspheres, including those providing for controlled release of the active ingredient(s). Other suitable bioadhesive cationic polymers include acidic gelatin, polygalactosamine, polyamino acids such as polylysine, polyhistidine, polyornithine, polyquaternary compounds, prolamine, polyimine, diethylaminoethyldextran (DEAE), DEAE-imine, DEAE-methacrylate, DEAE-acrylamide, DEAE-dextran, DEAE-cellulose, poly-p-aminostyrene, polyoxethane, copolymethacrylates, polyamidoamines, cationic starches, polyvinylpyridine, and polythiodiethylaminomethylethylene.

The compositions can be formulated in any suitable manner. Minicell compositions may be uniformly (homogeneously) or non-uniformly (heterogeneously) dispersed in the carrier. Suitable formulations include dry and liquid formulations. Dry formulations include freeze dried and lyophilized powders, which are particularly well suited for aerosol delivery to the sinuses or lung, or for long term storage followed by reconstitution in a suitable diluent prior to administration. Other preferred dry formulations include those wherein a composition disclosed herein is compressed into tablet or pill form suitable for oral administration or compounded into a sustained release formulation. When the composition is intended for oral administration to be delivered to epithelium in the intestines, it is preferred that the formulation be encapsulated with an enteric coating to protect the formulation and prevent premature release of the minicell compositions included therein. As those in the art will appreciate, the compositions disclosed herein can be placed into any suitable dosage form. Pills and tablets represent some of such dosage forms. The compositions can also be encapsulated into any suitable capsule or other coating material, for example, by compression, dipping, pan coating, spray drying, etc. Suitable capsules include those made from gelatin and starch. In turn, such capsules can be coated with one or more additional materials, for example, and enteric coating, if desired. Liquid formulations include aqueous formulations, gels, and emulsions.

Some embodiments provide compositions that comprise a bioadhesive, preferably a mucoadhesive, coating. A "bioadhesive coating" is a coating that allows a substance (e.g., a minicell composition) to adhere to a biological surface or substance better than occurs absent the coating. A "mucoadhesive coating" is a preferred bioadhesive coating that allows a substance, for example, a composition to adhere better to mucosa occurs absent the coating. For example, minicells can be coated with a mucoadhesive. The coated particles can then be assembled into a dosage form suitable for delivery to an organism. Preferably, and depending upon the location where the cell surface transport moiety to be targeted is expressed, the dosage form is then coated with another coating to protect the formulation until it reaches the desired location, where the mucoadhesive enables the formulation to be retained while the composition interacts with the target cell surface transport moiety.

Compositions disclosed herein can be administered to any organism, for example an animal, preferably a mammal, bird, fish, insect, or arachnid. Preferred mammals include bovine, canine, equine, feline, ovine, and porcine animals, and non-human primates. Humans are particularly preferred. Multiple techniques of administering or delivering a compound exist in the art including, but not limited to, oral, rectal (e.g. an enema or suppository) aerosol (e.g., for nasal or pulmonary delivery), parenteral, and topical administration. Preferably, sufficient quantities of the biologically active peptide are delivered to achieve the intended effect. The particular amount of composition to be delivered will depend on many factors, including the effect to be achieved, the type of organism to which the composition is delivered, delivery route, dosage regimen, and the age, health, and sex of the organism. As such, the particular dosage of a composition incorporated into a given formulation is left to the ordinarily skilled artisan's discretion.

Those skilled in the art will appreciate that when the compositions disclosed herein are administered as agents to achieve a particular desired biological result, which may include a therapeutic, diagnostic, or protective effect(s) (including vaccination), it may be possible to combine the minicell composition with a suitable pharmaceutical carrier. The choice of pharmaceutical carrier and the preparation of the minicells as a therapeutic or protective agent will depend on the intended use and mode of administration. Suitable formulations and methods of administration of therapeutic agents include those for oral, pulmonary, nasal, buccal, ocular, dermal, rectal, intravenous, or vaginal delivery.

Depending on the mode of delivery employed, the context-dependent functional entity can be delivered in a variety of pharmaceutically acceptable forms. For example, the context-dependent functional entity can be delivered in the form of a solid, solution, emulsion, dispersion, and the like, incorporated into a pill, capsule, tablet, suppository, aerosol, droplet, or spray. Pills, tablets, suppositories, aerosols, powders, droplets, and sprays may have complex, multilayer structures and have a large range of sizes. Aerosols, powders, droplets, and sprays may range from small (1 micron) to large (200 micron) in size.

Pharmaceutical compositions disclosed herein can be used in the form of a solid, a lyophilized powder, a solution, an emulsion, a dispersion, and the like, wherein the resulting composition contains one or more of the compounds disclosed herein, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Examples of a stabilizing dry agent include triulose, preferably at concentrations of 0.1% or greater (See, e.g., U.S. Pat. No. 5,314,695). The active compound is included in the pharmaceutical composition in an amount sufficient to produce the desired effect upon the process or condition of diseases.

6. Therapeutic Indications

The present disclosure relates to minicell-mediated immunotherapy against cancer(s) including but not limited to solid tumors, metastatic tumors, and liquid tumors. Solid and metastatic tumors include those of epithelial, fibroblast, muscle and bone origin and include but are not limited to breast, lung, pancreatic, prostatic, testicular, ovarian, gastric, intestinal, mouth, tongue, pharynx, hepatic, anal, rectal, colonic, esophageal, urinary bladder, gall bladder, skin, uterine, vaginal, penal, and renal cancers. Other solid cancer types that may be treated with the immunomodulatory minicells disclosed herein include but are not limited to adenocarcinomas, sarcomas, fibrosarcomas, and cancers of the eye, brain, and bone. Liquid tumors that can be treated by the immunomodulatory minicells disclosed herein include but are not limited to non-Hodgkin's lymphoma, myeloma, Hodgkin's lymphoma, acute lymphocytic leukemia, chronic lymphocytic leukemia, acute myeloid leukemia, chronic myeloid leukemia, and other leukemias.

Immunomodulatory activities of VAX-P, VAX-IP, and VAX-IPD minicells in vivo is shown in FIGS. 3-6 and as further described in Examples 2-4. The first in vivo evidence that immunomodulatory effects are contributing to the anti-tumor properties of perfringolysin O containing minicell formulations such as VAX-P, VAX-IP, and VAX-IPD minicells was unexpected. In performing control experiments in the development and in vivo characterization of VAX-IP, it was unexpectedly discovered that the removal of the targeting moiety invasin had little to no effect on in vivo efficacy (see FIG. 3). However, the removal of the perfringolysin O component had a marked effect on the ability of minicells to prevent tumor growth. It was also unexpectedly discovered that minicells could have profound anti-tumor effects against tumors that had colonized the ovaries of female mice, even though minicells were undetectable (i.e. did not localize) in ovaries (see FIGS. 4 & 5). In those same mice, tumors that had colonized the lung were also significantly prevented from growing and demonstrated ample minicell co-localization. Taken together, these disparate results indicate that tumor localization may not be critical for an anti-tumor effect and there is likely another global factor, likely to be some aspect of the immune system at play. In addition, it was demonstrated that minicells containing perfringolysin O had no effect on tumors grown in severely immune compromised NIH-III mice (lack NK cell function in addition to T-cell function) (see FIG. 6).

Figure 7:
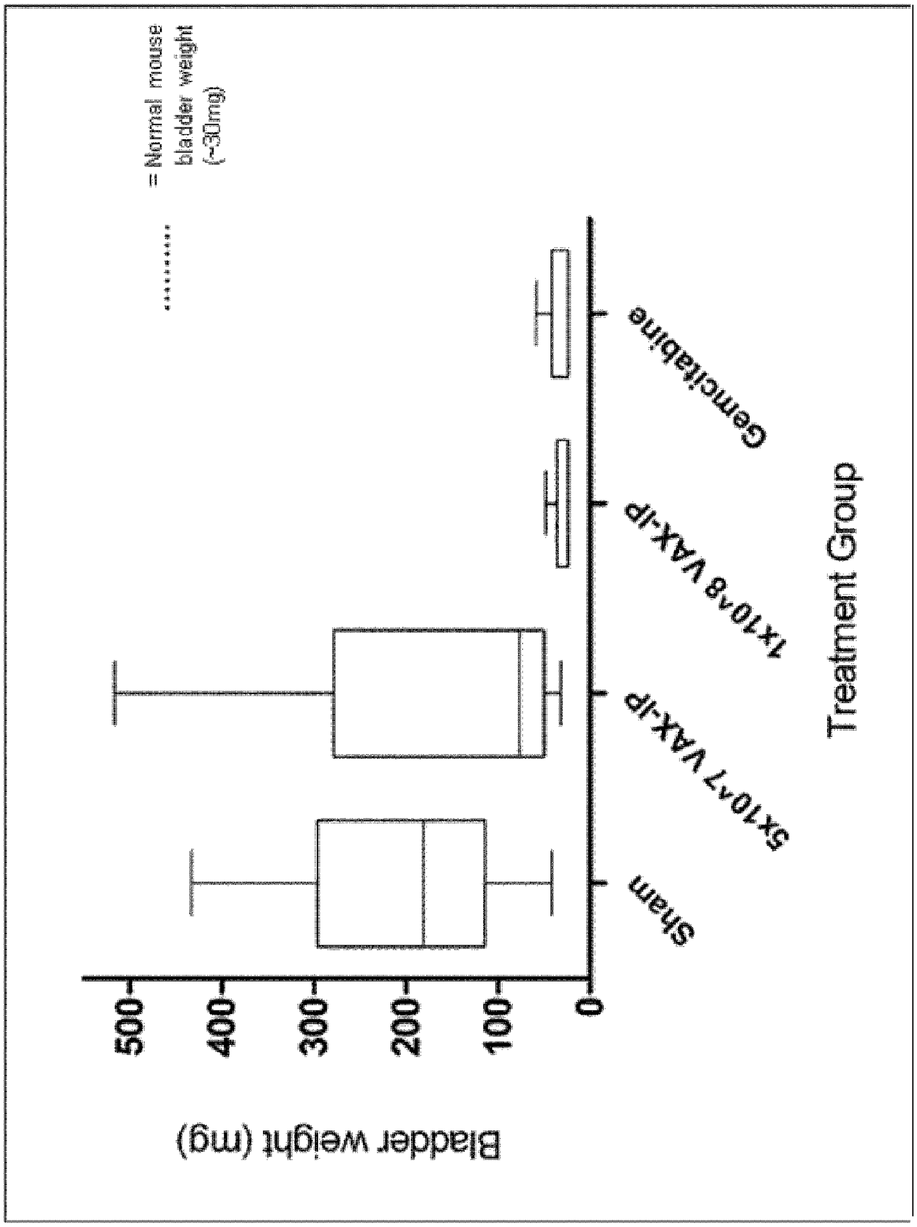
FIG. 7 is a plot showing VAX-IP minicells are highly effective in the MB49 murine model of established non-muscle invasive bladder cancer.

As a result of the immunomodulatory effect of minicells formulated as described herein, one non-limiting yet preferred therapeutic application of the immunomodulatory minicells of the present invention is in the intravesical administration and treatment of non-muscle invasive bladder cancer. As shown in FIG. 7 and described in Example 5, immunodulatory minicells have already demonstrated efficacy in a mouse model of non-muscle invasive bladder cancer.

7. Minicell Preparations

Some embodiments relate to creating an optimized strain and preparing immunomodulatory minicells from, but not limited to, the bacterial family Enterobacteriaceae.

In some embodiments, the level of minicell producing viable parental cell contamination is less than 1 in $10^5$ minicells. In some embodiments, the level of minicell producing viable parental cell contamination is less than 1 in $10^6$ minicells.

In some embodiments, the level of minicell-producing viable parental cell contamination is less than 1 in $10^7$ minicells.

In some embodiments, the level of minicell-producing viable parental cell contamination is less than 1 in $10^8$ minicells.

In some embodiments, the level of minicell-producing viable parental cell contamination is less than 1 in $10^9$ minicells.

In some embodiments, the level of minicell-producing viable parental cell contamination is less than 1 in $10^{10}$ minicells.

In some embodiments, the level of minicell-producing viable parental cell contamination is less than 1 in $10^{11}$ minicells.

In some embodiments, the level of minicell-producing viable parental cell contamination is less than 1 in $10^{12}$ minicells.

In some embodiments, the level of minicell-producing viable parental cell contamination is less than 1 in $10^{13}$ minicells.

In some embodiments, the level of minicell-producing viable parental cell contamination is less than 1 in $10^{14}$ minicells.

In some embodiments, the level of minicell-producing viable parental cell contamination is less than 1 in $10^{15}$ minicells.

In some embodiments, the level of minicell-producing viable parental cell contamination is less than 1 in $10^{16}$ minicells.

Unless defined otherwise, all technical and scientific terms used herein have the same meaning as commonly understood by one of ordinary skill in the art. Although the present application has been described with reference to embodiments and examples, it should be understood that various modifications can be made without departing from the spirit of the invention. All references cited herein are expressly incorporated herein by reference in their entirety.

Embodiments of the present application are disclosed in further detail in the following examples, which are not in any way intended to limit the scope of the present application.

EXAMPLES

Example 1

Figure 2:
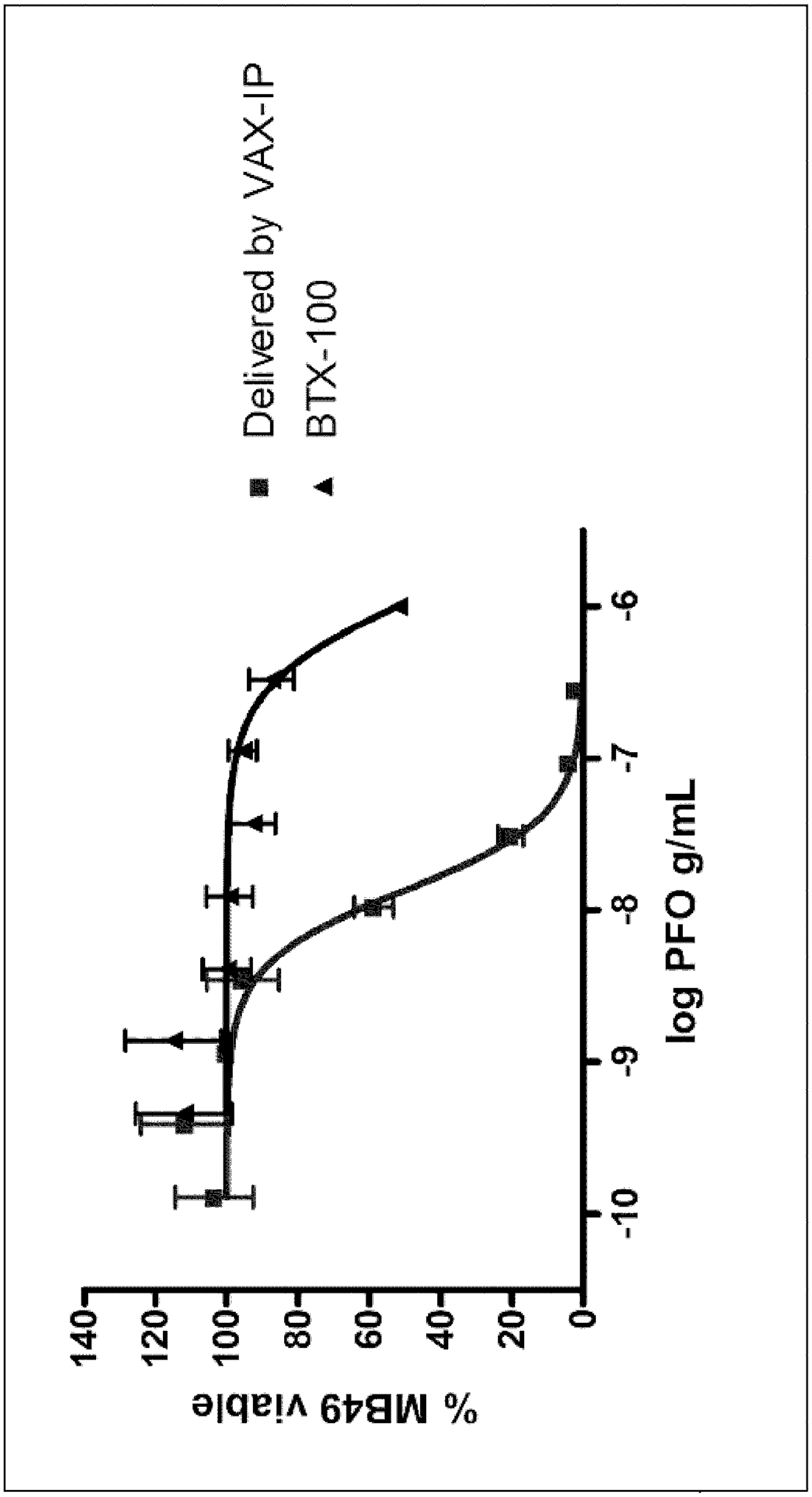
FIG. 2 is a plot showing in vitro cytotoxicity of purified recombinant perfringolysin O (BTX-100) versus equivalent amounts of perfringolysin O (PFO) delivered by minicells.
Figure 3:
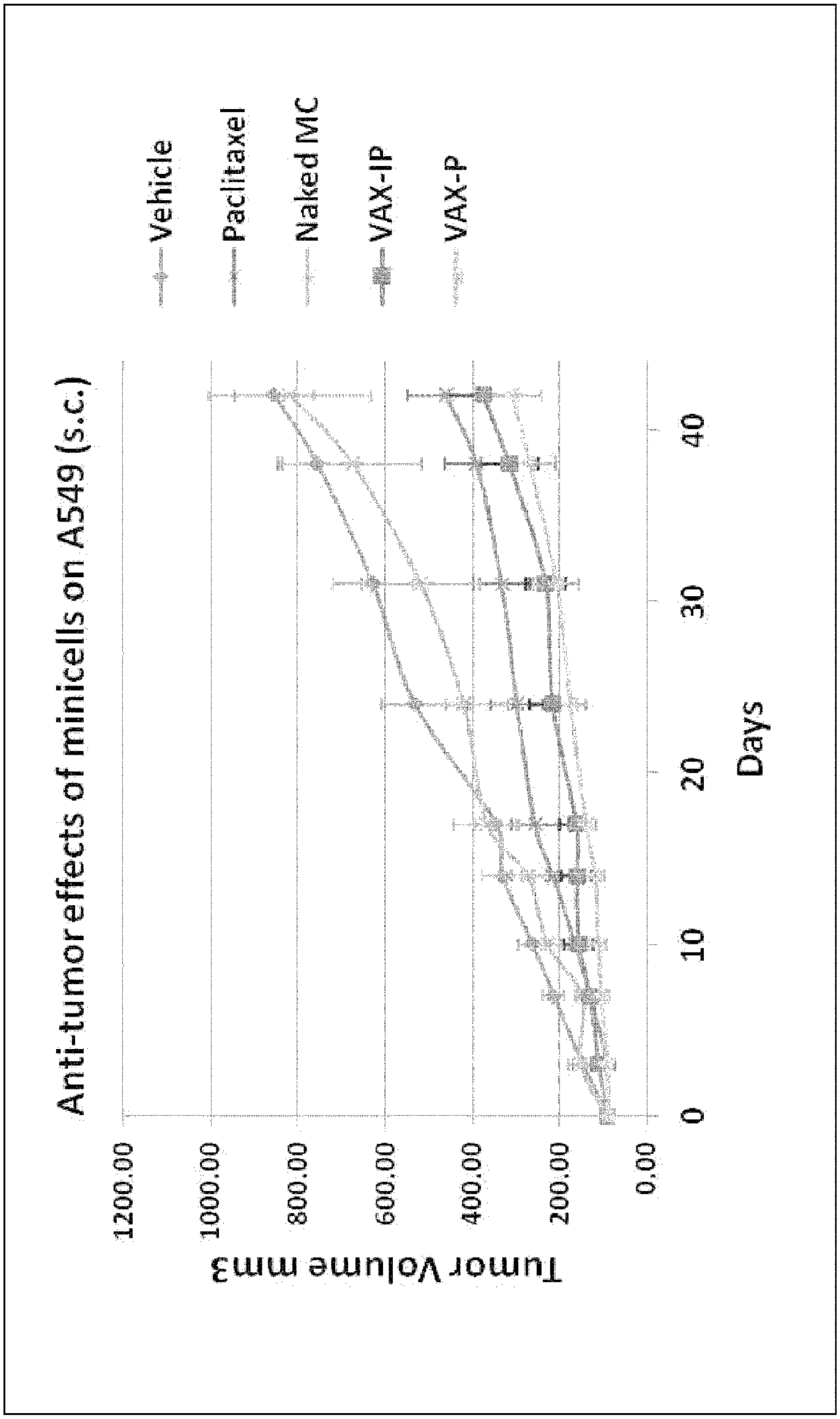
FIG. 3 is a plot showing removal of the targeting moiety invasin had no effect on anti-tumor activity of minicells containing PFO.
Figure 4:
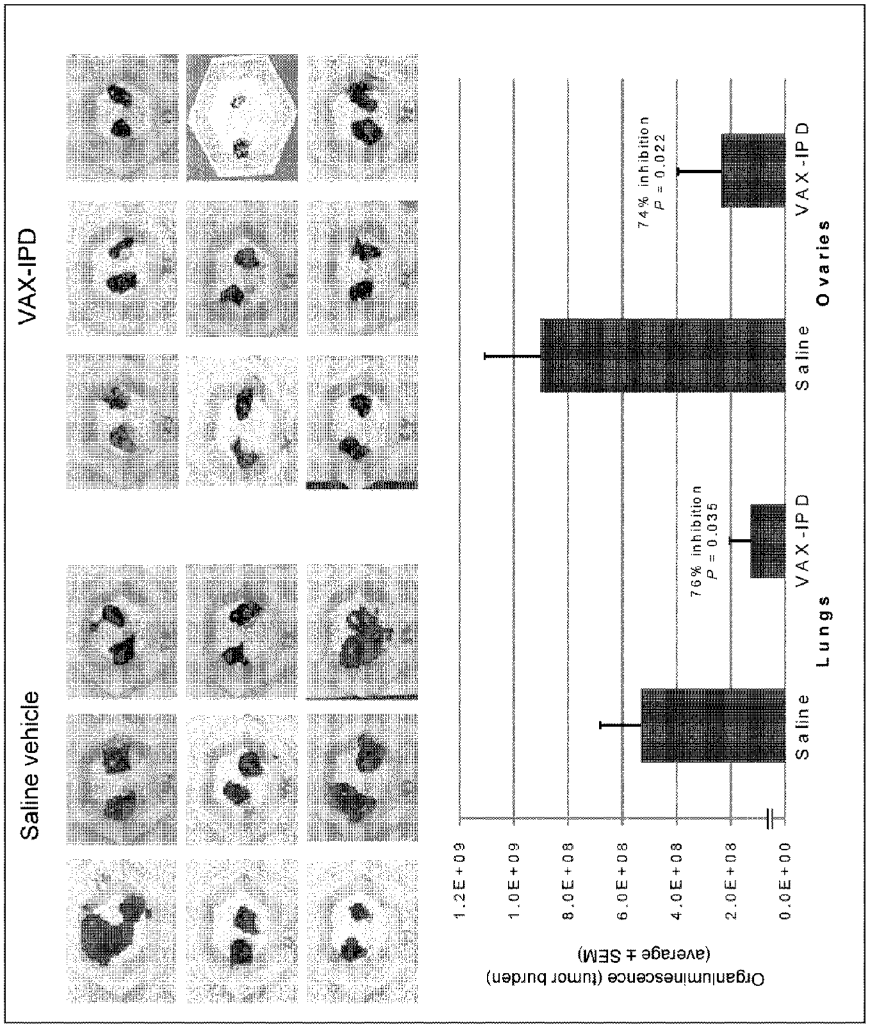
FIG. 4 depicts photographs and a chart showing similar anti-tumor effects of VAX-IPD minicells in lung and ovarian metastases.
Figure 5:
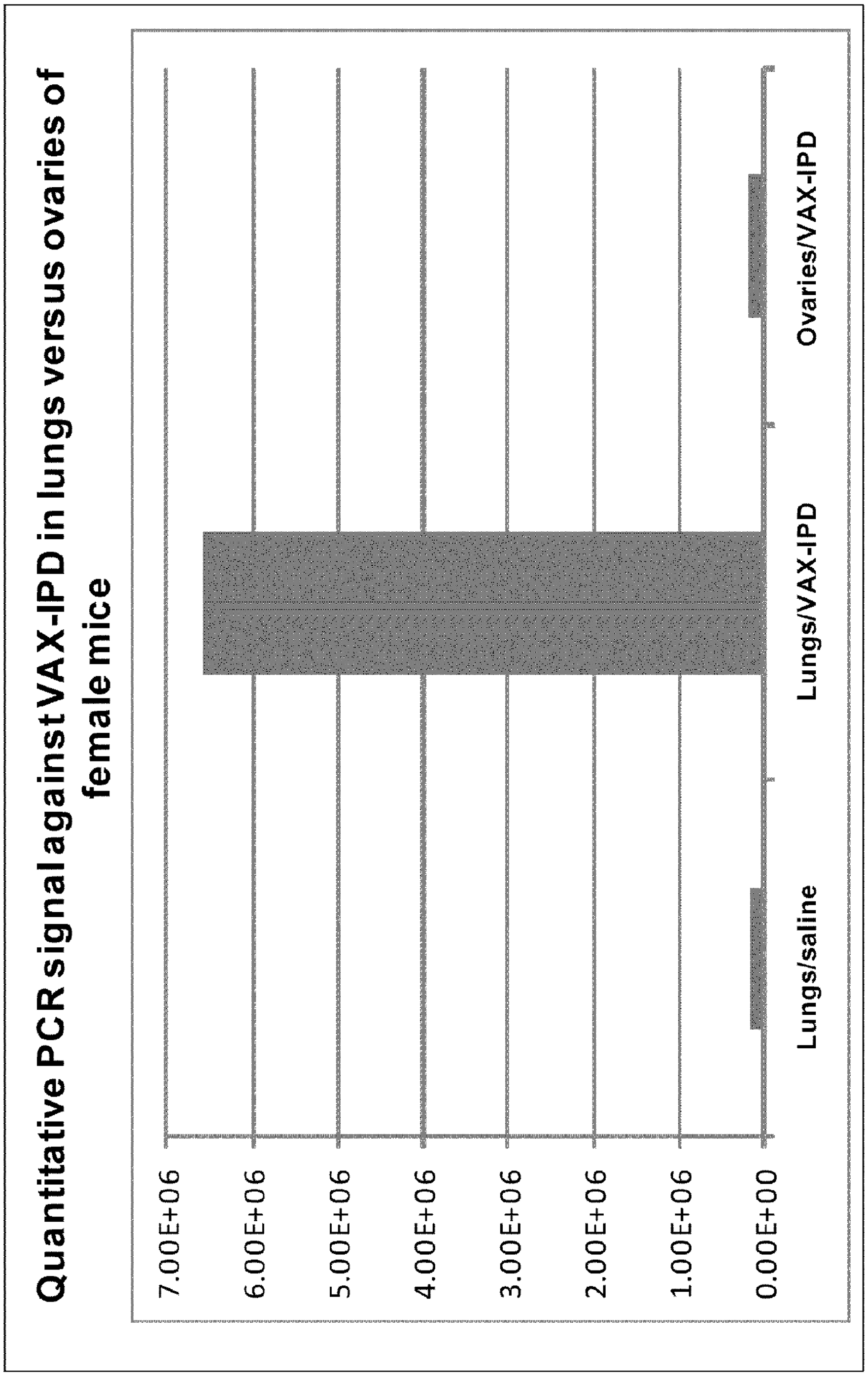
FIG. 5 is a histogram showing VAX-IPD minicells are detectable in the lungs but not the ovaries of mice following intravenous administration.
Figure 6:
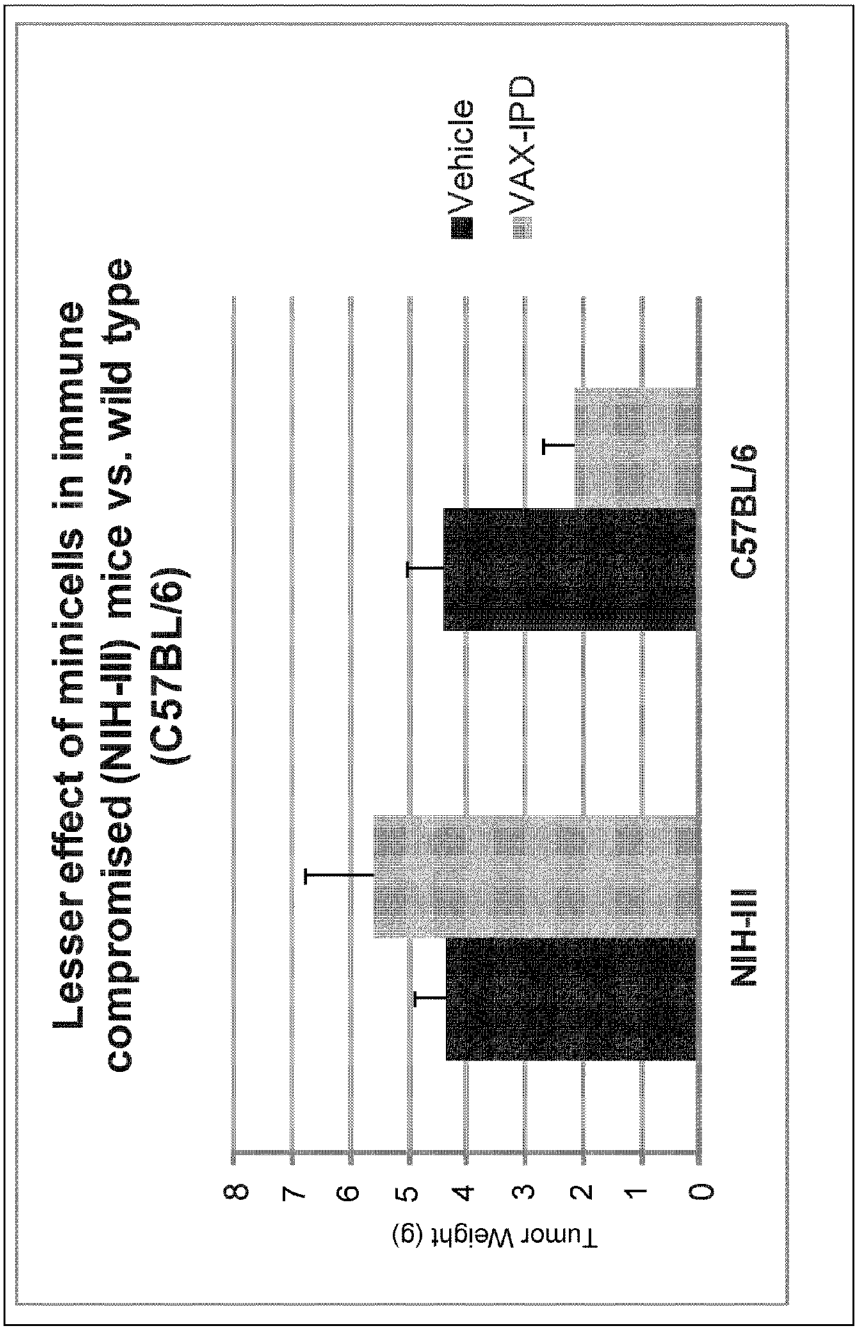
FIG. 6 is a histogram showing VAX-IPD minicells have little anti-tumor effect in severely immune compromised NIH-III mice.

Perfringolysin O is cytotoxic in vitro when targeted and delivered by VAX-IP minicells as demonstrated in Table 1 and FIG. 2. In vitro experiments were performed by seeding 96-well plates with 25,000 murine transitional cell carcinoma cell line MB49 in RPMI-1640 containing 10% fetal bovine serum, penicillin, and streptomycin. The following day, VAX-IP, VAX-I (containing no perfringolysin O), or recombinant perfringolysin O (BTX-100, purchased from ATCC) was added to cells at a ratio of VAX-IP and VAX-I minicells added per plated mammalian (the MOI) of 1,000:1. The concentration of BTX-100 added was equivalent to the amount of perfringolysin O being delivered by VAX-IP. Initially, lactate dehydrogenase (LDH) activity assays were used as a surrogate readout of cytotoxicity, primarily because LDH activity is a well known indicator of mammalian cell membrane leakage, a mechanism by which perfringolysin O has been reported to act. As expected and as shown in FIG. 1, murine lactate dehydrogenase (LDH), was released from MB49 cells almost immediately after exposure to BTX-100. MB49 cells treated with VAX-IP at an MOI of 1,000:1 also demonstrated LDH activity although the onset of release was slower, likely due to the requirement for VAX-IP minicell internalization, initiation of endosomal degradation, and eventual release of perfringolysin O into the target cell by way of endosomal membrane break down, mediated by perfringolysin O. VAX-I minicells, used as a control, demonstrated no significant release of LDH. Surprisingly, it was subsequently discovered that cells treated with BTX-100 had recovered by the 24 hr time point and were perfectly viable and adherent. On the other hand, those MB49 cells treated with VAX-IP minicells were detached from the plate and seemingly dead. To confirm this result, the same experiment was repeated comparing a range of VAX-IP minicells against a range of concentrations of BTX-100 but in this instance a standard MTT cell viability assay was performed at the 24 hr time point. The results of these experiments, shown in FIG. 2, clearly demonstrate that the intracellular delivery of a normally non-toxic concentration of perfringolysin O can be quite potent when delivered by minicells.

TABLE 1

| | mc/mL at 50% RBC lysis | PFO g/mL at 50% RBC lysis | PFO g/mc based on hemolytic assay | % LDH activity released from MB49 cells 2 hr after mc addition | PFO g/mL for LDH activity | mc to MB49 MOI at 50% MB49 viable | PFO g/mL at 50% MB49 viable |
|---|---|---|---|---|---|---|---|
| BTX-100 | NA | $1.75 \times 10^{-9}$ | NA | 87.8 | $5 \times 10^{-7}$ | NA | $1.07 \times 10^{-6}$ |
| VAX-I | No lysis | NA | 0 | 1.8 | 0 | No toxicity | NA |
| VAX-IP | $1.91 \times 10^{6}$ | NA | $9.16 \times 10^{-16}$ | 94.0 | $2.29 \times 10^{-7}$ | 307.2 | $1.41 \times 10^{-8}$ |

Example 2

The first line of evidence that minicells containing perfringolysin O stimulate anti-tumor immunomodulatory activity in vivo came from human xenograft studies performed in athymic Nude mice (Nude mice are partially immune compromised and lack a full complement of T-cell activity). The anti-tumor efficacy of VAX-IP minicells when given intravenously on a q3d schedule for a total of 6 doses was demonstrated in a subcutaneous xenograft study using the human pancreatic carcinoma cell line BxPC3 (see FIG. 3). In this model, tumor cells were implanted subcutaneously in Nude mice and allowed to reach a size of 100 $mm^3$ before being randomized into treatment groups. Tumor bearing mice were treated intravenously on a q3d schedule for 6 total doses with either saline vehicle, paclitaxel, $3.0\times10^8$ "naked" minicells (*E. coli* minicells containing no invasin or perfringolysin O), $3.0\times10^8$ VAX-P minicells (containing no invasin protein on the minicell surface), or $3.0\times10^8$ VAX-IP minicells. Surprisingly, the non-targeted control group, VAX-P minicells (containing no invasin protein on the minicell surface), was equally effective as VAX-IP minicells at preventing tumor growth in this model while "naked" minicells were ineffective. Anti-tumor activity in the absence of a tumor targeting moiety on the surface of the minicell vehicle was completely unexpected.

Example 3

The second line of evidence that minicells containing perfringolysin O stimulate anti-tumor immunomodulatory activity in vivo came from a syngeneic murine model of pulmonary and ovarian metastasis using the B16F10 murine melanoma cell line. In this model, B16F10 murine melanoma cells that constitutively express firefly luciferase were injected intravenously by tail vein into female Nude mice. Mice were injected once every 3 days with luciferin and animals imaged by whole mouse imaging for the presence of established metastases in the lungs of mice. Once tumor establishment was verified, mice were randomized into control groups and received either saline vehicle or $3.0\times10^8$ VAX-IPD minicells intravenously on a qd3 dosing schedule for a total of 6 doses. Significant anti-tumor activity against lung and ovarian metastases was observed in VAX-IPD minicells treated mice (see FIG. 4). In a second and parallel quantitative VAX-IPD plasmid specific PCR-based biodistribution study using the same model and dosing schedule, we determined that VAX-IPD localized to the lungs and lung tumors in mice. Surprisingly, at no time point tested, was VAX-IPD minicells localized to the ovaries or ovary tumors (see FIG. 5). From the combination of these two results, it was concluded that some global factor, likely to be one or more immune factors, must be contributing to anti-tumor activity if VAX-IPD minicells was not localizing to ovarian tissue or tumor but having a profound tumor suppressive effects at that organ site.

Example 4

Based on the observations of the in vivo experiments performed in Examples 2 and 3, above, a third study was performed using an established subcutaneous tumor variation of the syngeneic B16F10 murine melanoma model comparing anti-tumor efficacy of VAX-IPD minicells in fully immune competent C57/BL6 mice to anti-tumor activity in severely immune deficient NIH-III mice (same genetic background as C57/BL6 but lacking both T-cell and Natural Killer cell activity). After tumors had grown to a size of 100 $mm^3$, mice were randomized into treatment groups and treated with either saline or $3.0\times10^8$ VAX-IPD minicells intravenously on a q3d schedule for a total of 6 doses. Following the final dose, mice were euthanized, tumors surgically extracted, weighed, and scored for tumor burden. The results, shown in FIG. 6, demonstrate that VAX-IPD minicells is ineffective in severely immune compromised mice.

Example 5

The ability of VAX-IP minicells to work in a mouse model of non-muscle invasive bladder cancer is demonstrated in FIG. 7. In this experiment, immune competent female C57/BL6 mice were anesthetized, subjected to catheterization of the urinary bladder and their urinary bladder walls cauterized at two distinct sites using an electrosurgical device (Bovie 940, set at 5 W) attached to a platinum guide wire and inserted through the catheter. Following cauterization, bladders were rinsed with 50 uL of PBS and then 100,000 MB49 murine transitional cell carcinoma tumor cells were instilled through the catheter. The catheter was locked in place for 2 hr to ensure tumor adherence to the bladder wall. Catheters were removed and animals were allowed to recover from anesthesia. Animals were monitored daily by bladder palpation until tumors could be detected, at which time they were randomized into treatment groups. Mice then received an intravesical administration of either saline, $5\times10^7$ VAX-IP minicells, or $1\times10^8$ VAX-IP minicells through a urinary catheter on a q3d schedule for a total of 5 doses. Animals were then euthanized, and bladders excised, weighed and scored for tumor burden. The results demonstrate a strong dose-dependent anti-tumor effect of VAX-IP minicells against established MB49 urinary bladder carcinoma in this model.

Example 6

Figure 9:
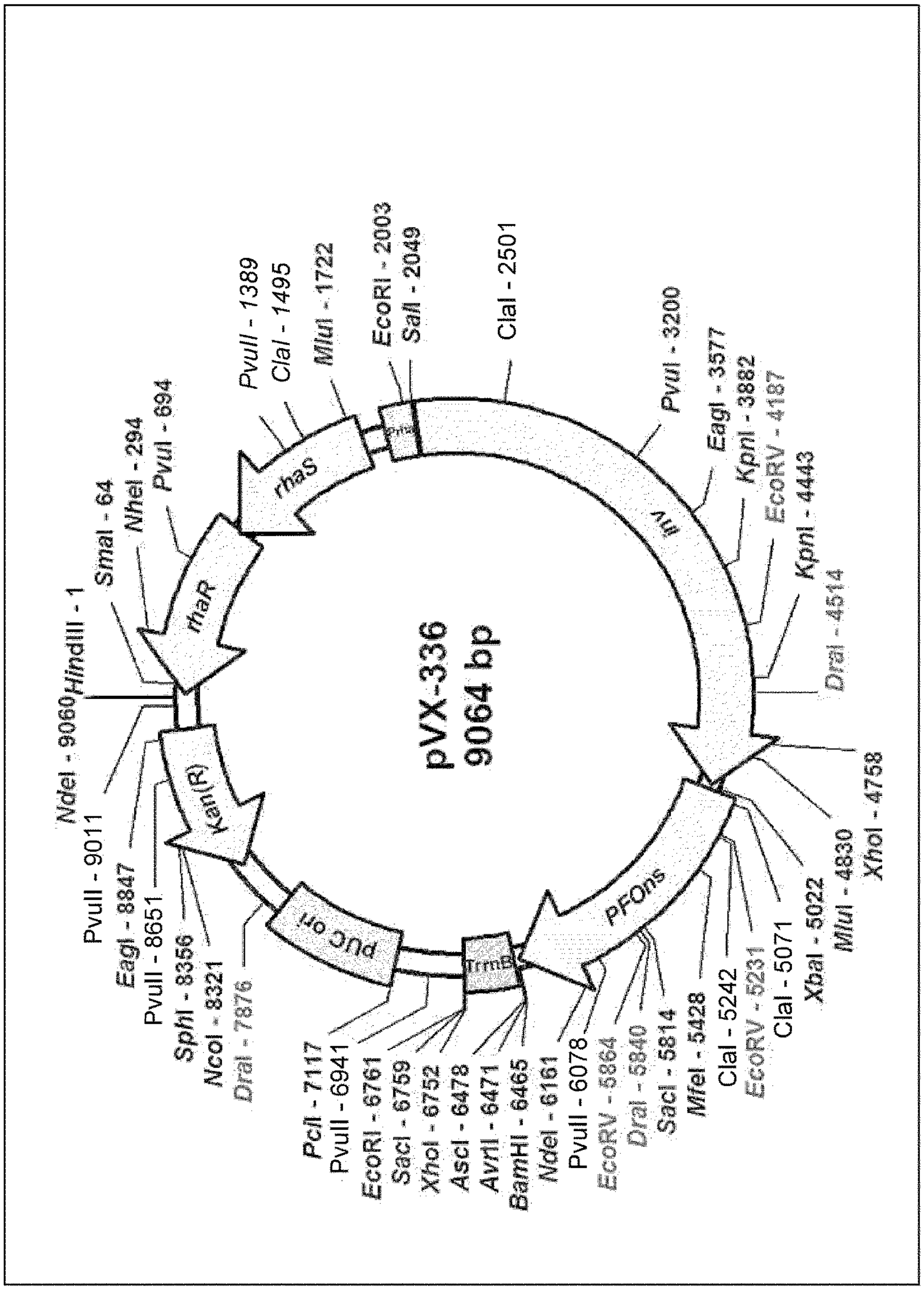
FIG. 9 is a plasmid map of pVX-336.
Figure 10:
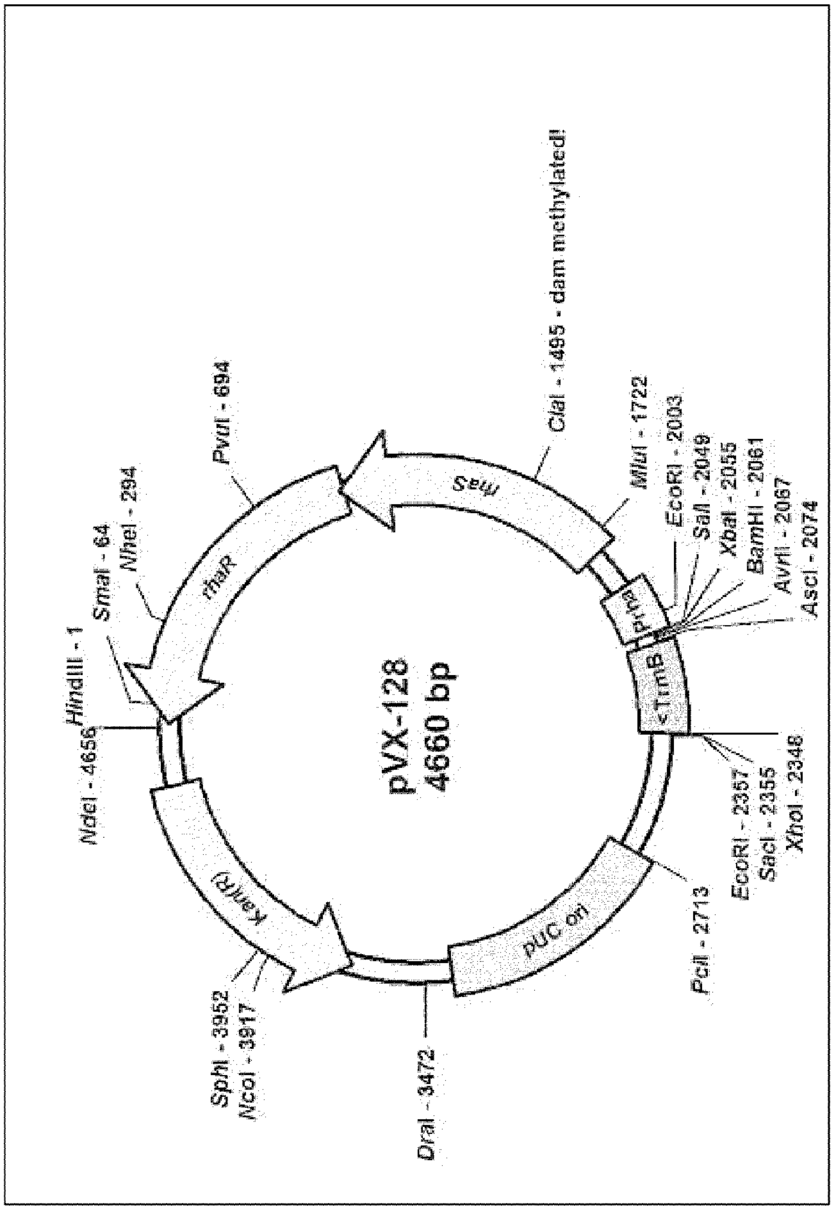
FIG. 10 is a plasmid map of pVX-128.
Figure 11:
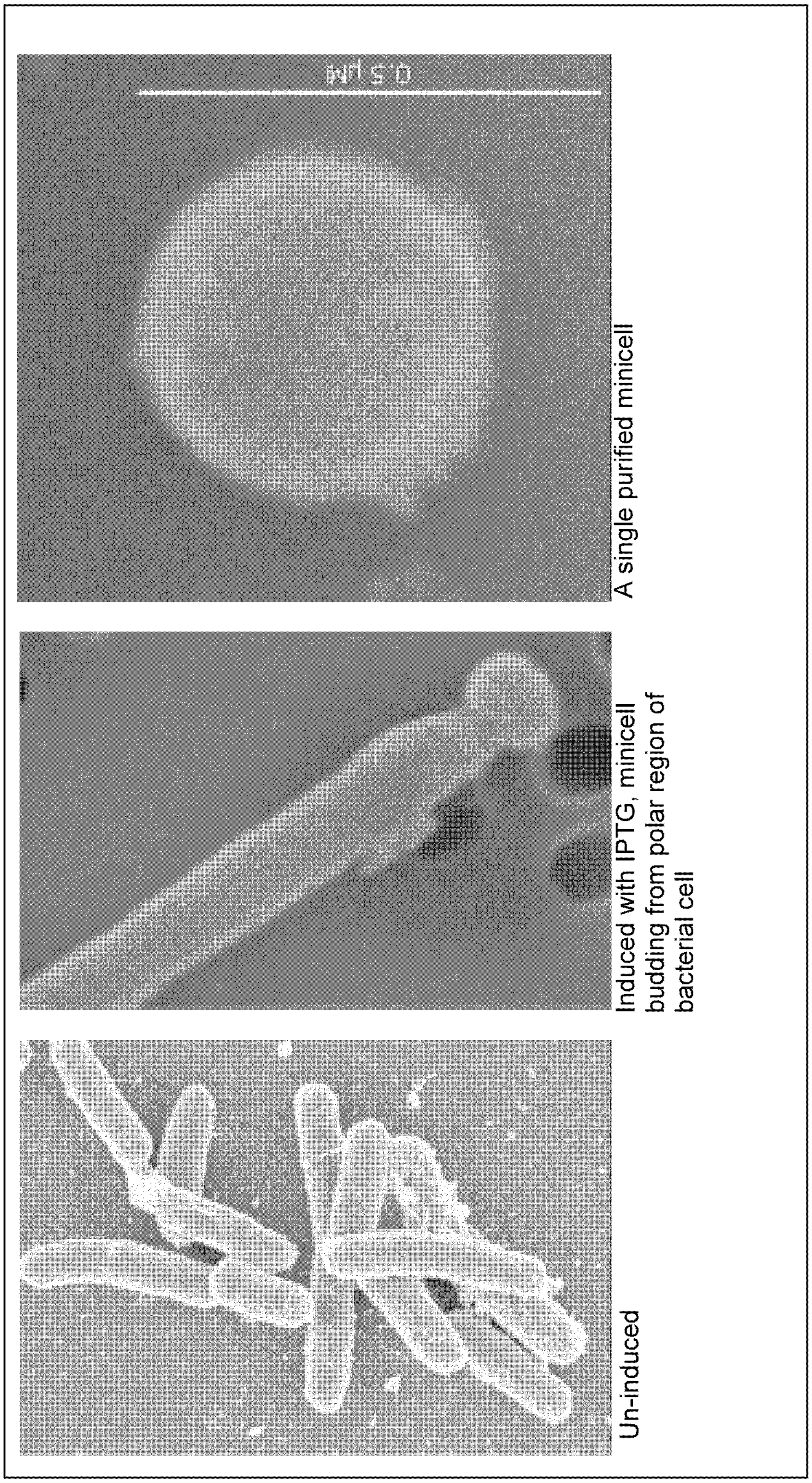
FIG. 11 shows scanning electron micrographs of inducible minicell formation.
Figure 12:
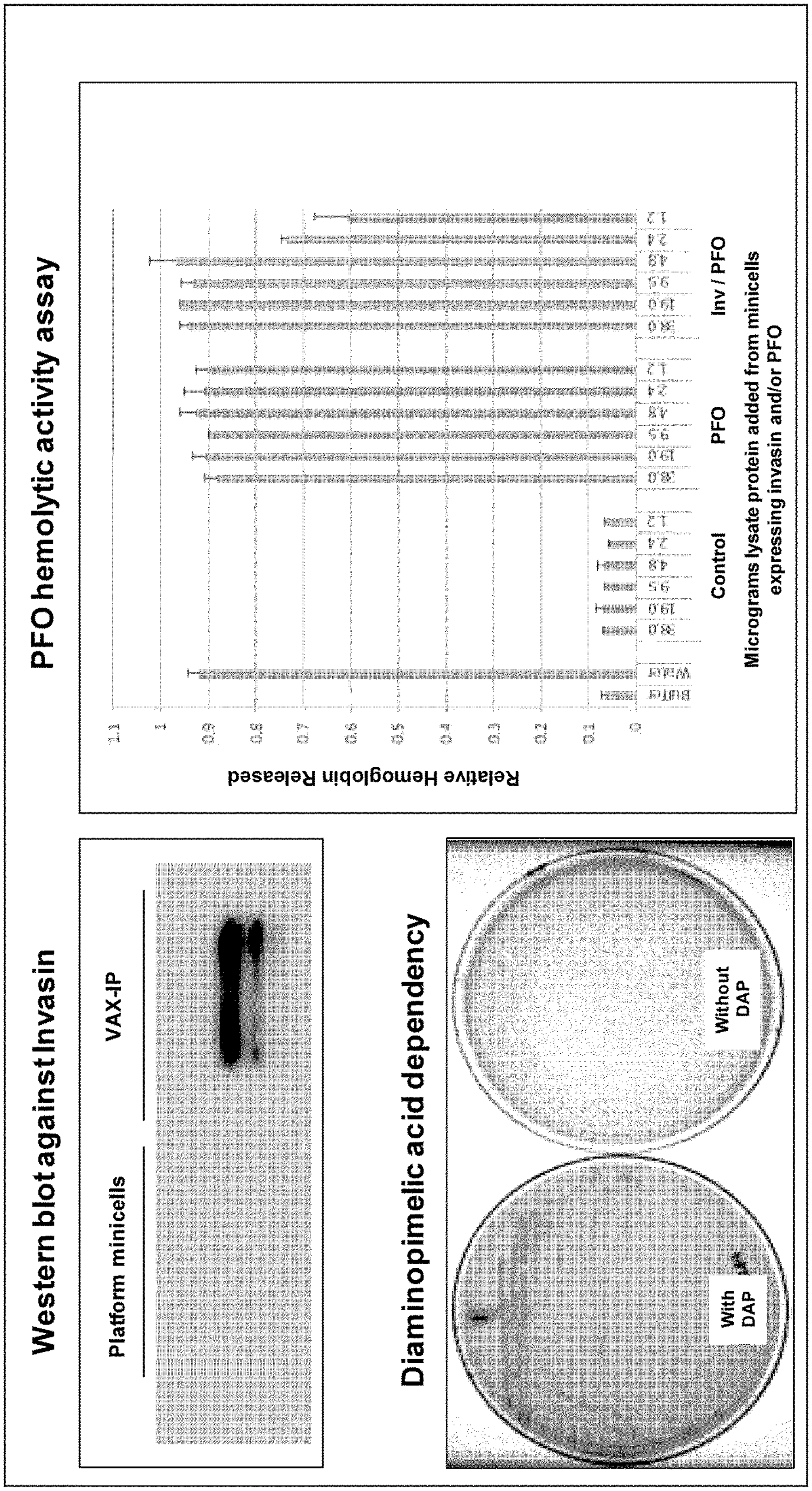
FIG. 12 depicts photographs and a chart demonstrating expression of invasin and perfringolysin O in VAX-IP minicells.

The production of VAX-IP minicells begins with the cloning of plasmid pVX-336 (SEQ ID NO. 3). pVX-336 (plasmid map shown in FIG. 9) was constructed by directionally subcloning invasin into the SalI and XbaI site of the L-rhamnose inducible plasmid pVX-128 (SEQ ID NO. 4, plasmid map shown in FIG. 10). After the identification of positive clones, a subsequent directional subcloning of perfringolysin O into the unique XbaI and BamHI sites was conducted to create a transcriptional fusion between invasin and perfringolysin O (a single prokaryotic message RNA coding for two proteins, invasin and perfringolysin O). Following positive sequence identification of pVX-336, the plasmid was introduced into an IPTG-inducible minicell-producing strain of *E. coli* (see Step 1 of schematic in FIG. 8 and actual strain producing minicells upon induction with IPTG in FIG. 11). The strain also contains a chromosomal copy of a thermo-inducible I-ceuI suicide gene, a deletion in the dapA gene (rendering parental strain unable to grow outside of the laboratory or in mammals), and a deletion in the lpxM gene (attenuates Lipid A component of lipopolysaccharide). After introduction of the plasmid and selection on LB agar containing 10 ug/mL diaminopimelic acid and 50 ug/mL kanamycin, a single colony is used to start an overnight culture grown at 30° C. in liquid LB media containing the same. The following day, the starter culture is diluted 1/100 into 3L of fresh LB media containing 10 ug/mL diaminopimelic acid and 50 ug/mL kanamycin and grown at 30° C. while shaking. Culture turbidity is monitored by Optical Density 600 (OD 600). At an OD 600 of 0.1, the culture is induced to express invasin and perfringolysin O from pVX-336 by the addition of L-rhamnose to a final concentration of 90 uM. At an OD 600 of 1.0, the culture is induced for VAX-IP minicell formation by the addition of IPTG to a final concentration of 100 uM. The culture is allowed to grow into stationary phase overnight and the following day VAX-IP minicells are purified using a combination of differential centrifugation steps followed by density gradient purification as is standard in the art. Once purified, minicells are tested for PFO content and activity by way of red blood cell hemolysis assay as well as for the presence of invasin by Western blot (see FIG. 12 for hemolysis assay and Western blot), the primary detection antibody for which is a mouse monoclonal IgG2b (mAb3A2) specific for invasion. The red blood cell hemolytic assay is performed by lysing VAX-IP minicells with a combination of 2 mM EDTA, 10 ug/mL lysozyme, an 5 mM cysteine, followed by and osmotic shock with ice cold distilled water. Once lysed, lysates are quantified for protein content and the appropriate amounts added to 100,000 sheep red blood cells in a 96 well plate. Plates are incubated at 37° C. with vigorous shaking for 1 hr. Following the 1 hr incubation time, red blood cells are centrifuged down at 1,000×G for 5 min, and the supernatants moved to a new 96 well plate for analysis of hemoglobin release as a measure of hemolytic activity at a wavelength of 541 nm.

What is claimed is:

1. A bacterial minicell, comprising perfringolysin O and invasin, wherein the invasin is displayed on the surface of the bacterial minicell.

2. The bacterial minicell of claim 1, wherein the invasin is from *Yersinia pseudotuberculosis*.

3. The bacterial minicell of claim 1, further comprising an exogenous polypeptide that is not a protein toxin.

4. The bacterial minicell of claim 1, further comprising a protein toxin.

5. The bacterial minicell of claim 4, wherein the protein toxin is a catalytic fragment of diphtheria toxin, gelonin, *Pseudomonas* exotoxin A, or ricin A.

6. The bacterial minicell of claim 1, wherein the minicell is a Th1 immunomodulatory minicell.

7. The bacterial minicell of claim 1, wherein the bacterial minicell is produced from a minicell-producing parental bacterial cell with an inactivated lpxM gene.

8. The bacterial minicell of claim 7, wherein the minicell is produced from a minicell-producing strain of *Salmonella* spp., *Listeria* spp., Mycobacterium spp., *Shigella* spp., *Yersinia* spp., or *Escherichia coli*.

9. The bacterial minicell of claim 8, further comprising one or more Th1 cytokines, one or more pore forming cytolysin proteins, one or more phospholipases, or one or more immunomodulatory nucleic acids.

10. The bacterial minicell of claim 9, wherein at least one of the one or more Th1 cytokines is IL-2, GMCSF, IL-12p40, IL-12p70, IL-18, TNF-α, or IFN-γ.

11. A method of treating bladder cancer, comprising administering to a patient in need thereof a bacterial minicell, wherein the bacterial minicell comprises perfringolysin O and invasin, wherein the invasin is displayed on the surface of the bacterial minicell.

12. The method of claim 11, wherein the bladder cancer is non-muscle invasive bladder cancer.

* * * * *

UNITED STATES PATENT AND TRADEMARK OFFICE

CERTIFICATE OF CORRECTION

PATENT NO. : 9,566,321 B2
APPLICATION NO. : 15/044403
DATED : February 14, 2017
INVENTOR(S) : Matthew J. Giacalone It is certified that error appears in the above-identified patent and that said Letters Patent is hereby corrected as shown below:

In the Specification

In Column 1 at Line 56, Change "pyrogenes," to --pyrogen,--.

In Column 1 at Line 57, Change "choleraesius," to --choleraesuis,--.

In Column 6 at Line 34, After "phagocyctic" insert --eukaryotic cell without stimulating appreciable endocytosis of said minicells.--.

In Column 6 at Lines 35-36, After "used" delete "eukaryotic cell without stimulating appreciable endocytosis of said minicells.".

In Column 6 at Line 42, Change "Betal" to --Beta1--.

In Column 6 at Line 48, Change "Betal" to --Beta1--.

In Column 6 at Line 54, Change "Betal" to --Beta1--.

In Column 6 at Line 60, Change "Betal" to --Beta1--.

In Column 6 at Line 66, Change "Betal" to --Beta1--.

In Column 7 at Line 5 (approx.), Change "Betal" to --Beta1--.

In Column 7 at Line 8 (approx.), Change "O(PFO)" to --O (PFO)--.

In Column 7 at Line 12 (approx.), Change "Betal" to --Beta1--.

Signed and Sealed this
Twenty-seventh Day of June, 2017

Joseph Matal

*Performing the Functions and Duties of the*
*Under Secretary of Commerce for Intellectual Property and*
*Director of the United States Patent and Trademark Office*

In Column 8 at Line 64, Change “Richettsia,” to --Rickettsia,--.

In Column 8 at Lines 66-67, Change “Richettsia,” to --Rickettsia,--.

In Column 9 at Line 17 (approx.), Change “synonomous” to --synonymous--.

In Column 12 at Line 42, Change “T is” to --Tis--.

In Column 12 at Line 43, Change “lamnia” to --lamina--.

In Column 12 at Line 49, Change “transuretheral” to --transurethral--.

In Column 12 at Line 60, Change “mytomycin” to --mitomycin--.

In Column 14 at Line 6, Change “mytomycin” to --mitomycin--.

In Column 14 at Line 10, Change “cytokin,” to --cytokine,--.

In Column 18 at Line 56, Change “Franciscella” to --Francisella--.

In Column 18 at Line 57, Change “pneumophilia,” to --pneumophila,--.

In Column 18 at Line 57, Change “Kliebsella,” to --Klebsiella,--.

In Column 20 at Line 36, Change “and and” to --and--.

In Column 24 at Lines 63-64, Change “Franciscella” to --Francisella--.

In Column 24 at Line 64, Change “pneumophilia,” to --pneumophila,--.

In Column 24 at Line 65, Change “Kliebsella,” to --Klebsiella,--.

In Column 25 at Lines 61-62, Change “Franciscella” to --Francisella--.

In Column 25 at Line 62, Change “pneumophilia,” to --pneumophila,--.

In Column 25 at Line 63, Change “Kliebsella,” to --Klebsiella,--.

In Column 26 at Line 62, Change “pneumophilia,” to --pneumophila,--.

In Column 26 at Line 63, Change “kliebsella,” to --Klebsiella,--.

In Column 27 at Line 64, Change “prlG” to --prlC--.

In Column 28 at Line 11, Change “mc” to --rnc--.

In Column 30 at Line 49, Change “Enterobacteriacea.” to --Enterobacteriaceae.--.

In Column 30 at Line 62, Change “Enterobacteriacea” to --Enterobacteriaceae--.

In Column 30 at Line 67, Change “Enterobacteriacea.” to --Enterobacteriaceae.--.

In Column 31 at Lines 1-2, Change “Enterobacteriacea” to --Enterobacteriaceae--.

In Column 31 at Line 3, Change “Enterobacteriacea” to --Enterobacteriaceae--.

In Column 35 at Line 63, Change “perfringes” to --perfringens--.

In Column 35 at Line 65, Change “mosquilicidal” to --mosquitocidal--.

In Column 35 at Line 66, Change “mellitin,” to --melittin,--.

In Column 37 at Lines 59-60, Change “prolamine,” to --prolamin,--.

In Column 37 at Line 63, Change “polyoxethane,” to --polyoxyethane,--.

In Column 40 at Line 26, Change “polyoxethane,” to --polyoxyethane,--.

In Column 42 at Line 52, Change “immunomnodulatory” to --immunomodulatory--.

In Column 44 at Line 46, Change “invasion.” to --invasin.--.

In the Claims

In Column 58 at Line 31, In Claim 9, change “Thl” to --Th1--.

SEQUENCE LISTING

```
<160> NUMBER OF SEQ ID NOS: 4

<210> SEQ ID NO 1
<211> LENGTH: 11
<212> TYPE: PRT
<213> ORGANISM: Artificial Sequence
```

<220> FEATURE:
<223> OTHER INFORMATION: Conserved Sequence Motif

<400> SEQUENCE: 1

Glu Cys Thr Gly Leu Ala Trp Glu Trp Trp Arg
 1               5                   10

<210> SEQ ID NO 2
<211> LENGTH: 6
<212> TYPE: PRT
<213> ORGANISM: Artificial Sequence
<220> FEATURE:
<223> OTHER INFORMATION: Conserved Sequence Motif

<400> SEQUENCE: 2

Trp Glu Trp Trp Arg Thr
 1               5

<210> SEQ ID NO 3
<211> LENGTH: 9064
<212> TYPE: DNA
<213> ORGANISM: Artificial Sequence
<220> FEATURE:
<223> OTHER INFORMATION: pVX-336

<400> SEQUENCE: 3
aagcttaatt aatctttctg cgaattgaga tgacgccact ggctgggcgt catcccggtt 60
tcccgggtaa acaccaccga aaaatagtta ctatcttcaa agccacattc ggtcgaaata 120
tcactgatta acaggcggct atgctggaga agatattgcg catgacacac tctgacctgt 180
cgcagatatt gattgatggt cattccagtc tgctggcgaa attgctgacg caaaacgcgc 240
tcactgcacg atgcctcatc acaaaattta tccagcgcaa agggactttt caggctagcc 300
gccagccggg taatcagctt atccagcaac gtttcgctgg atgttggcgg caacgaatca 360
ctggtgtaac gatggcgatt cagcaacatc accaactgcc cgaacagcaa ctcagccatt 420
tcgttagcaa acggcacatg ctgactactt tcatgctcaa gctgaccgat aacctgccgc 480
gcctgcgcca tccccatgct acctaagcgc cagtgtggtt gccctgcgct ggcgttaaat 540
cccggaatcg ccccctgcca gtcaagattc agcttcagac gctccgggca ataaataata 600
ttctgcaaaa ccagatcgtt aacggaagcg taggagtgtt tatcgtcagc atgaatgtaa 660
aagagatcgc cacgggtaat gcgataaggg cgatcgttga gtacatgcag gccattaccg 720
cgccagacaa tcaccagctc acaaaaatca tgtgtatgtt cagcaaagac atcttgcgga 780
taacggtcag ccacagcgac tgcctgctgg tcgctggcaa aaaaatcatc tttgagaagt 840
tttaactgat gcgccaccgt ggctacctcg gccagagaac gaagttgatt attcgcaata 900
tggcgtacaa atacgttgag aagattcgcg ttattgcaga aagccatccc gtccctggcg 960
aatatcacgc ggtgaccagt taaactctcg gcgaaaaagc gtcgaaaagt ggttactgtc 1020
gctgaatcca cagcgatagg cgatgtcagt aacgctggcc tcgctgtggc gtagcagatg 1080
tcgggctttc atcagtcgca ggcggttcag gtatcgctga ggcgtcagtc ccgtttgctg 1140
cttaagctgc cgatgtagcg tacgcagtga aagagaaaat tgatccgcca cggcatccca 1200
attcacctca tcggcaaaat ggtcctccag ccaggccaga agcaagttga gacgtgatgc 1260
gctgttttcc aggttctcct gcaaactgct tttacgcagc aagagcagta attgcataaa 1320
caagatctcg cgactggcgg tcgagggtaa atcattttcc ccttcctgct gttccatctg 1380
tgcaaccagc tgtcgcacct gctgcaatac gctgtggtta acgcgccagt gagacggata 1440

-continued ctgcccatcc agctcttgtg gcagcaactg attcagcccg gcgagaaact gaaatcgatc 1500
cggcgagcga tacagcacat tggtcagaca cagattatcg gtatgttcat acagatgccg 1560
atcatgatcg cgtacgaaac agaccgtgcc accggtgatg gtatagggct gcccattaaa 1620
cacatgaata cccgtgccat gttcgacaat cacaatttca tgaaaatcat gatgatgttc 1680
aggaaaatcc gcctgcggga gccggggttc tatcgccacg gacgcgttac cagacggaaa 1740
aaaatccaca ctatgtaata cggtcatact ggcctcctga tgtcgtcaac acggcgaaat 1800
agtaatcacg aggtcaggtt cttaccttaa attttcgacg gaaaaccacg taaaaaacgt 1860
cgatttttca agatacagcg tgaattttca ggaaatgcgg tgagcatcac atcaccacaa 1920
ttcagcaaat tgtgaacatc atcacgttca tctttccctg gttgccaatg gcccattttc 1980
ctgtcagtaa cgagaaggtc gcgaattcag gcgcttttta gactggtcgt aatgaaattc 2040
aggaggtggt cgacattatg atggttttcc agccaatcag tgagtttctc ttgataagga 2100
atgcgggaat gtctatgtat tttaataaaa taatttcatt taatattatt tcacgaatag 2160
ttatttgtat ctttttgata tgtggaatgt tcatggctgg ggcttcagaa aaatatgatg 2220
ctaacgcacc gcaacaggtc cagccttatt ctgtctcttc atctgcattt gaaaatctcc 2280
atcctaataa tgaaatggag agttcaatca atccctttc cgcatcggat acagaaagaa 2340
atgctgcaat aatagatcgc gccaataagg agcaggagac tgaagcggtg aataagatga 2400
taagcaccgg ggccaggtta gctgcatcag gcagggcatc tgatgttgct cactcaatgg 2460
tgggcgatgc ggttaatcaa gaaatcaaac agtggttaaa tcgattcggt acggctcaag 2520
ttaatctgaa ttttgacaaa aatttttcgc taaaagaaag ctctcttgat tggctggctc 2580
cttggtatga ctctgcttca ttcctctttt ttagtcagtt aggtattcgc aataaagaca 2640
gccgcaacac acttaacctt ggcgtcggga tacgtacatt ggagaacggt tggctgtacg 2700
gacttaatac tttttatgat aatgatttga ccggccacaa ccaccgtatc ggtcttggtg 2760
ccgaggcctg gaccgattat ttacagttgg ctgccaatgg gtattttcgc ctcaatggat 2820
ggcactcgtc gcgtgatttc tccgactata aagagcgccc agccactggg ggggatttgc 2880
gcgcgaatgc ttatttacct gcactcccac aactgggggg gaagttgatg tatgagcaat 2940
acaccggtga gcgtgttgct ttatttggta aagataatct gcaacgcaac ccttatgccg 3000
tgactgccgg gatcaattac acccccgtgc ctctactcac tgtcggggta gatcagcgta 3060
tggggaaaag cagtaagcat gaaacacagt ggaacctcca aatgaactat cgcctgggcg 3120
agagttttca gtcgcaactt agcccttcag cggtggcagg aacacgtcta ctggcggaga 3180
gccgctataa ccttgtcgat cgtaacaata atatcgtgtt ggagtatcag aaacagcagg 3240
tggttaaact gacattatcg ccagcaacta tctccggcct gccgggtcag gtttatcagg 3300
tgaacgcaca agtacaaggg gcatctgctg taagggaaat tgtctggagt gatgccgaac 3360
tgattgccgc tggcggcaca ttaacaccac tgagtaccac acaattcaac ttggttttac 3420
cgccttataa acgcacagca caagtgagtc gggtaacgga cgacctgaca gccaactttt 3480
attcgcttag tgcgctcgcg gttgatcacc aaggaaaccg atctaactca ttcacattga 3540
gcgtcaccgt tcagcagcct cagttgacat taacggcggc cgtcattggt gatggcgcac 3600
cggctaatgg gaaaactgca atcaccgttg agttcaccgt tgctgatttt gaggggaaac 3660
ccttagccgg gcaggaggtg gtgataacca ccaataatgg tgcgctaccg aataaaatca 3720
cggaaaagac agatgccaac ggcgtcgcgc gcattgcatt aaccaatacg acagatggcg 3780
tgacggtagt cacagcagaa gtggaggggc aacggcaaag tgttgatacc cactttgtta 3840

-continued agggtactat cgcggcggat aaatccactc tggctgcggt accgacatct atcatcgctg 3900
atggtctaat ggcttcaacc atcacgttgg agttgaagga tacctatggg gacccgcagg 3960
ctggcgcgaa tgtggctttt gacacaacct taggcaatat gggcgttatc acggatcaca 4020
atgacggcac ttatagcgca ccattgacca gtaccacgtt gggggtagca acagtaacgg 4080
tgaaagtgga tggggctgcg ttcagtgtgc cgagtgtgac ggttaatttc acggcagatc 4140
ctattccaga tgctggccgc tccagtttca ccgtctccac accggatatc ttggctgatg 4200
gcacgatgag ttccacatta tcctttgtcc ctgtcgataa gaatggccat tttatcagtg 4260
ggatgcaggg cttgagtttt actcaaaacg gtgtgccggt gagtattagc cccattaccg 4320
agcagccaga tagctatacc gcgacggtgg ttgggaatag tgtcggtgat gtcacaatca 4380
cgccgcaggt tgataccctg atactgagta cattgcagaa aaaaatatcc ctattcccgg 4440
tacctacgct gaccggtatt ctggttaacg ggcaaaattt cgctacggat aaagggttcc 4500
cgaaaacgat ctttaaaaac gccacattcc agttacagat ggataacgat gttgctaata 4560
atactcagta tgagtggtcg tcgtcattca cacccaatgt atcggttaac gatcagggtc 4620
aggtgacgat tacctaccaa acctatagcg aagtggctgt gacggcgaaa agtaaaaaat 4680
tcccaagtta ttcggtgagt tatcggttct acccaaatcg gtggatatac gatggcggca 4740
cttcgctggt atcgagtctc gaggccagca gacaatgcca aggttcagat atgtctgcgg 4800
ttcttgaatc ctcacgtgca accaacggaa cgcgtgcgcc tgacgggaca ttgtggggcg 4860
agtgggggag cttgaccgcg tatagttctg attggcaatc tggtgaatat tgggtcaaaa 4920
agaccagcac ggattttgaa accatgaata tggacacagg cgcactgcaa ccagggcctg 4980
catacttggc gttcccgctc tgtgcgctgt caatataata atctagaagg aggaacaata 5040
tgaaagatat taccgacaaa aatcagtcca tcgattcagg cattagctct ctgtcttata 5100
accgtaatga agtgctggcg tccaatggtg acaaaatcga atcatttgtt ccgaaagaag 5160
gcaaaaaagc cggtaacaaa ttcattgtgg ttgaacgtca gaaacgctct ctgaccacga 5220
gtccggttga tatctccatt atcgattcag tcaatgaccg tacctatccg ggtgcactgc 5280
aactggcaga caaagcattt gtggaaaacc gtccgacgat tctgatggtt aaacgcaaac 5340
cgattaacat caatattgat ctgccgggcc tgaaaggtga aaatagtatc aaagtggatg 5400
acccgaccta tggcaaagtt tcgggtgcaa ttgatgaact ggtcagcaaa tggaacgaaa 5460
aatacagttc cacccatacg ctgccggcgc gtacccagta ttcggaaagc atggtgtact 5520
ctaaaagtca aatctcatcg gcgctgaacg ttaatgccaa agtcctggaa aactctctgg 5580
gtgtggattt taatgcggtt gccaacaatg agaaaaaagt gatgatcctg gcatataaac 5640
agattttcta caccgttagt gctgatctgc cgaaaaaccc gtctgacctg tttgatgaca 5700
gtgtcacgtt caacgatctg aaacaaaaag gcgtgtctaa tgaagcgccg ccgctgatgg 5760
tgtctaacgt tgcctatggt cgtaccattt acgttaaact ggaaaccacg agctctagta 5820
aagatgtcca ggcggccttt aaagccctga tcaaaaacac cgatatcaaa aatagccagc 5880
aatacaaaga catctacgaa aattcctcat tcaccgcagt cgtgctgggc ggtgatgctc 5940
aggaacacaa caaagttgtc acgaaagatt ttgacgaaat ccgcaaagtg attaaagata 6000
acgcaacctt ctcgacgaaa aatccggctt atccgatttc gtacaccagc gtttttctga 6060
aagataacag cgtcgcagct gtgcataata aaaccgacta tatcgaaacc accagcaccg 6120
aatacagcaa aggcaaaatt aatctggatc actccggtgc atatgtcgct cagttcgaag 6180

-continued

```
tggcctggga tgaagtttca tacgacaaag aaggcaatga agtgctgacc cataaaacgt   6240
gggatggtaa ctatcaagac aaaaccgcac actactccac ggttattccg ctggaagcaa   6300
acgctcgtaa tatccgcatt aaagcgcgtg aatgcaccgg tctggcatgg gaatggtggc   6360
gtgatgtcat cagcgaatat gacgtgccgc tgacgaacaa tatcaatgtg tcaatctggg   6420
gcaccacgct gtatccgggt agttccatca cctataatta ataaggatcc cctaggggcg   6480
cgcctggtag tgtggggtct ccccatgcga gagtagggaa ctgccaggca tcaaataaaa   6540
cgaaaggctc agtcgaaaga ctgggccttt cgttttatct gttgtttgtc ggtgaacgct   6600
ctcctgagta ggacaaatcc gccgggagcg gatttgaacg ttgcgaagca acggcccgga   6660
gggtggcggg caggacgccc gccataaact gccaggcatc aaattaagca gaaggccatc   6720
ctgacggatg gcctttttgc gtttctacaa actcgagctc gaattcgtaa tcatggtcat   6780
agctgtttcc tgtgtgaaat tgttatccgc tcacaattcc acacaacata cgagccggaa   6840
gcataaagtg taaagcctgg ggtgcctaat gagtgagcta actcacatta attgcgttgc   6900
gctcactgcc cgctttccag tcgggaaacc tgtcgtgcca gctgcattaa tgaatcggcc   6960
aacgcgcggg gagaggcggt ttgcgtattg ggcgctcttc cgcttcctcg ctcactgact   7020
cgctgcgctc ggtcgttcgg ctgcggcgag cggtatcagc tcactcaaag gcggtaatac   7080
ggttatccac agaatcaggg gataacgcag gaaagaacat gtgagcaaaa ggccagcaaa   7140
agcccaggaa ccgtaaaaag gccgcgttgc tggcgttttt ccataggctc cgcccccctg   7200
acgagcatca caaaaatcga cgctcaagtc agaggtggcg aaacccgaca ggactataaa   7260
gataccaggc gtttccccct ggaagctccc tcgtgcgctc tcctgttccg accctgccgc   7320
ttaccggata cctgtccgcc tttctccctt cgggaagcgt ggcgctttct catagctcac   7380
gctgtaggta tctcagttcg gtgtaggtcg ttcgctccaa gctgggctgt gtgcacgaac   7440
cccccgttca gcccgaccgc tgcgccttat ccggtaacta tcgtcttgag tccaacccgg   7500
taagacacga cttatcgcca ctggcagcag ccactggtaa caggattagc agagcgaggt   7560
atgtaggcgg tgctacagag ttcttgaagt ggtggcctaa ctacggctac actagaagga   7620
cagtatttgg tatctgcgct ctgctgaagc cagttacctt cggaaaaaga gttggtagct   7680
cttgatccgg caaacaaacc accgctggta gcggtggttt ttttgtttgc aagcagcaga   7740
ttacgcgcag aaaaaaagga tctcaagaag atcctttgat cttttctacg gggtctgacg   7800
ctcagtggaa cgaaaactca cgttaaggga ttttggtcat gagattatca aaaaggatct   7860
tcacctagat ccttttaaat taaaaatgaa gttttagcac gtgctattat tgaagcattt   7920
atcagggtta ttgtctcatg agcggataca tatttgaatg tatttagaaa aataaacaaa   7980
taggggttcc gcgcacattt ccccgaaaag tgccacctgt atgcggtgtg aaataccgca   8040
cagatgcgta aggagaaaat accgcatcag gaaattgtaa gcgttaataa ttcagaagaa   8100
ctcgtcaaga aggcgataga aggcgatgcg ctgcgaatcg ggagcggcga taccgtaaag   8160
cacgaggaag cggtcagccc attcgccgcc aagctcttca gcaatatcac gggtagccaa   8220
cgctatgtcc tgatagcggt ccgccacacc cagccggcca cagtcgatga atccagaaaa   8280
gcggccattt tccaccatga tattcggcaa gcaggcatcg ccatgggtca cgacgagatc   8340
ctcgccgtcg ggcatgctcg ccttgagcct ggcgaacagt tcggctggcg cgagcccctg   8400
atgctcttcg tccagatcat cctgatcgac aagaccggct tccatccgag tacgtgctcg   8460
ctcgatgcga tgtttcgctt ggtggtcgaa tgggcaggta gccggatcaa gcgtatgcag   8520
ccgccgcatt gcatcagcca tgatggatac tttctcggca ggagcaaggt gagatgacag   8580
```

```
gagatcctgc cccggcactt cgcccaatag cagccagtcc cttcccgctt cagtgacaac   8640

gtcgagcaca gctgcgcaag gaacgcccgt cgtggccagc cacgatagcc gcgctgcctc   8700

gtcttgcagt tcattcaggg caccggacag gtcggtcttg acaaaaagaa ccgggcgccc   8760

ctgcgctgac agccggaaca cggcggcatc agagcagccg attgtctgtt gtgcccagtc   8820

atagccgaat agcctctcca cccaagcggc cggagaacct gcgtgcaatc catcttgttc   8880

aatcatgcga aacgatcctc atcctgtctc ttgatcagag cttgatcccc tgcgccatca   8940

gatccttggc ggcgagaaag ccatccagtt tactttgcag ggcttcccaa ccttaccaga   9000

gggcgcccca gctggcaatt ccggttcgct tgctgtccat aaaaccgccc agtagaagca   9060

tatg                                                                9064


<210> SEQ ID NO 4
<211> LENGTH: 4660
<212> TYPE: DNA
<213> ORGANISM: Artificial Sequence
<220> FEATURE:
<223> OTHER INFORMATION: pVX-128

<400> SEQUENCE: 4

aagcttaatt aatctttctg cgaattgaga tgacgccact ggctgggcgt catcccggtt     60

tcccgggtaa acaccaccga aaaatagtta ctatcttcaa agccacattc ggtcgaaata    120

tcactgatta acaggcggct atgctggaga agatattgcg catgacacac tctgacctgt    180

cgcagatatt gattgatggt cattccagtc tgctggcgaa attgctgacg caaaacgcgc    240

tcactgcacg atgcctcatc acaaaattta tccagcgcaa agggactttt caggctagcc    300

gccagccggg taatcagctt atccagcaac gtttcgctgg atgttggcgg caacgaatca    360

ctggtgtaac gatggcgatt cagcaacatc accaactgcc cgaacagcaa ctcagccatt    420

tcgttagcaa acggcacatg ctgactactt tcatgctcaa gctgaccgat aacctgccgc    480

gcctgcgcca tccccatgct acctaagcgc cagtgtggtt gccctgcgct ggcgttaaat    540

cccggaatcg ccccctgcca gtcaagattc agcttcagac gctccgggca ataaataata    600

ttctgcaaaa ccagatcgtt aacggaagcg taggagtgtt tatcgtcagc atgaatgtaa    660

aagagatcgc cacgggtaat gcgataaggg cgatcgttga gtacatgcag gccattaccg    720

cgccagacaa tcaccagctc acaaaaatca tgtgtatgtt cagcaaagac atcttgcgga    780

taacggtcag ccacagcgac tgcctgctgg tcgctggcaa aaaaatcatc tttgagaagt    840

tttaactgat gcgccaccgt ggctacctcg gccagagaac gaagttgatt attcgcaata    900

tggcgtacaa atacgttgag aagattcgcg ttattgcaga aagccatccc gtccctggcg    960

aatatcacgc ggtgaccagt taaactctcg gcgaaaaagc gtcgaaaagt ggttactgtc   1020

gctgaatcca cagcgatagg cgatgtcagt aacgctggcc tcgctgtggc gtagcagatg   1080

tcgggctttc atcagtcgca ggcggttcag gtatcgctga ggcgtcagtc ccgtttgctg   1140

cttaagctgc cgatgtagcg tacgcagtga aagagaaaat tgatccgcca cggcatccca   1200

attcacctca tcggcaaaat ggtcctccag ccaggccaga agcaagttga gacgtgatgc   1260

gctgttttcc aggttctcct gcaaactgct tttacgcagc aagagcagta attgcataaa   1320

caagatctcg cgactggcgg tcgagggtaa atcattttcc ccttcctgct gttccatctg   1380

tgcaaccagc tgtcgcacct gctgcaatac gctgtggtta acgcgccagt gagacggata   1440

ctgcccatcc agctcttgtg gcagcaactg attcagcccg gcgagaaact gaaatcgatc   1500
```

-continued

```
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggtggt cgactctaga ggatccccta ggggcgcgcc tggtagtgtg gggtctcccc   2100
atgcgagagt agggaactgc caggcatcaa ataaaacgaa aggctcagtc gaaagactgg   2160
gcctttcgtt ttatctgttg tttgtcggtg aacgctctcc tgagtaggac aaatccgccg   2220
ggagcggatt tgaacgttgc gaagcaacgg cccggagggt ggcgggcagg acgcccgcca   2280
taaactgcca ggcatcaaat taagcagaag gccatcctga cggatggcct tttgcgtttt   2340
ctacaaactc gagctcgaat tcgtaatcat ggtcatagct gtttcctgtg tgaaattgtt   2400
atccgctcac aattccacac aacatacgag ccggaagcat aaagtgtaaa gcctggggtg   2460
cctaatgagt gagctaactc acattaattg cgttgcgctc actgcccgct ttccagtcgg   2520
gaaacctgtc gtgccagctg cattaatgaa tcggccaacg cgcggggaga ggcggtttgc   2580
gtattgggcg ctcttccgct tcctcgctca ctgactcgct gcgctcggtc gttcggctgc   2640
ggcgagcggt atcagctcac tcaaaggcgg taatacggtt atccacagaa tcaggggata   2700
acgcaggaaa gaacatgtga gcaaaaggcc agcaaaagcc caggaaccgt aaaaaggccg   2760
cgttgctggc gtttttccat aggctccgcc cccctgacga gcatcacaaa aatcgacgct   2820
caagtcagag gtggcgaaac ccgacaggac tataaagata ccaggcgttt ccccctggaa   2880
gctccctcgt gcgctctcct gttccgaccc tgccgcttac cggatacctg tccgcctttc   2940
tcccttcggg aagcgtggcg ctttctcata gctcacgctg taggtatctc agttcggtgt   3000
aggtcgttcg ctccaagctg ggctgtgtgc acgaaccccc cgttcagccc gaccgctgcg   3060
ccttatccgg taactatcgt cttgagtcca acccggtaag acacgactta tcgccactgg   3120
cagcagccac tggtaacagg attagcagag cgaggtatgt aggcggtgct acagagttct   3180
tgaagtggtg gcctaactac ggctacacta gaaggacagt atttggtatc tgcgctctgc   3240
tgaagccagt taccttcgga aaaagagttg gtagctcttg atccggcaaa caaaccaccg   3300
ctggtagcgg tggttttttt gtttgcaagc agcagattac gcgcagaaaa aaaggatctc   3360
aagaagatcc tttgatcttt tctacggggt ctgacgctca gtggaacgaa aactcacgtt   3420
aagggatttt ggtcatgaga ttatcaaaaa ggatcttcac ctagatcctt ttaaattaaa   3480
aatgaagttt tagcacgtgc tattattgaa gcatttatca gggttattgt ctcatgagcg   3540
gatacatatt tgaatgtatt tagaaaaata aacaaatagg ggttccgcgc acatttcccc   3600
gaaaagtgcc acctgtatgc ggtgtgaaat accgcacaga tgcgtaagga gaaaataccg   3660
catcaggaaa ttgtaagcgt taataattca gaagaactcg tcaagaaggc gatagaaggc   3720
gatgcgctgc gaatcgggag cggcgatacc gtaaagcacg aggaagcggt cagcccattc   3780
gccgccaagc tcttcagcaa tatcacgggt agccaacgct atgtcctgat agcggtccgc   3840
cacacccagc cggccacagt cgatgaatcc agaaaagcgg ccattttcca ccatgatatt   3900
```

-continued

```
cggcaagcag gcatcgccat gggtcacgac gagatcctcg ccgtcgggca tgctcgcctt   3960

gagcctggcg aacagttcgg ctggcgcgag cccctgatgc tcttcgtcca gatcatcctg   4020

atcgacaaga ccggcttcca tccgagtacg tgctcgctcg atgcgatgtt tcgcttggtg   4080

gtcgaatggg caggtagccg gatcaagcgt atgcagccgc cgcattgcat cagccatgat   4140

ggatactttc tcggcaggag caaggtgaga tgacaggaga tcctgccccg gcacttcgcc   4200

caatagcagc cagtcccttc ccgcttcagt gacaacgtcg agcacagctg cgcaaggaac   4260

gcccgtcgtg gccagccacg atagccgcgc tgcctcgtct tgcagttcat tcagggcacc   4320

ggacaggtcg gtcttgacaa aaagaaccgg gcgcccctgc gctgacagcc ggaacacggc   4380

ggcatcagag cagccgattg tctgttgtgc ccagtcatag ccgaatagcc tctccaccca   4440

agcggccgga gaacctgcgt gcaatccatc ttgttcaatc atgcgaaacg atcctcatcc   4500

tgtctcttga tcagagcttg atcccctgcg ccatcagatc cttggcggcg agaaagccat   4560

ccagtttact ttgcagggct tcccaacctt accagagggc gccccagctg gcaattccgg   4620

ttcgcttgct gtccataaaa ccgcccagta gaagcatatg                         4660
```